US006849713B2

(12) United States Patent
Zhang et al.

(10) Patent No.: US 6,849,713 B2
(45) Date of Patent: Feb. 1, 2005

(54) COMPOUNDS POSSESSING ANTIBACTERIAL, ANTIFUNGAL OR ANTITUMOR ACTIVITY

(75) Inventors: Wentao Zhang, Foster City, CA (US); Sebastian Johannes Reinhard Liehr, East Palo Alto, CA (US); Mark Douglas Velligan, Montara, CA (US); Natalia B. Dyatkina, Mountain View, CA (US); Janos Botyanszki, Cupertino, CA (US); Dong-Fang Shi, San Mateo, CA (US); Christopher Don Roberts, Belmont, CA (US); Alexander Khorlin, Mountain View, CA (US); Peter Harold Nelson, Los Altos, CA (US); Joseph Martin Muchowski, Sunnyvale, CA (US)

(73) Assignee: Genelabs Technologies, Inc., Redwood City, CA (US)

( * ) Notice: Subject to any disclaimer, the term of this patent is extended or adjusted under 35 U.S.C. 154(b) by 117 days.

(21) Appl. No.: 09/892,327

(22) Filed: Jun. 26, 2001

(65) Prior Publication Data

US 2002/0037856 A1 Mar. 28, 2002

Related U.S. Application Data

(60) Provisional application No. 60/214,478, filed on Jun. 27, 2000.

(51) Int. Cl.$^7$ ............................................... A61K 38/04
(52) U.S. Cl. ........................................................ 530/330
(58) Field of Search ......................................... 530/330

(56) References Cited

U.S. PATENT DOCUMENTS

| 4,107,288 A | 8/1978 | Oppenheim et al. |
| 4,912,199 A | 3/1990 | Lown et al. |
| 5,145,684 A | 9/1992 | Liversidge et al. |
| 5,502,068 A | 3/1996 | Lown et al. |
| 5,607,915 A | 3/1997 | Patton |
| 5,616,606 A | 4/1997 | Lown et al. |

OTHER PUBLICATIONS

Evans, D.A., et al., "The Asymmetric Synthesis of α–Amino Acids. Electrophilic Azidation of Chiral Imide Enolates, a Practical Approach to the Synthesis of (R)– and (S)–α–Azido Carboxylic Acids", *J. Am. Chem. Soc.*, vol. 112, pp. 4011–4030 (1990).

Gursky, G.V.., et al., "Synthetic Sequence–Specific Ligands", *Cold Springs Harbor Symposia on Quantitative Biology*, vol. XLVII, pp. 367–377 (1983).

March, J., *Advanced Organic Chemistry*, 4$^{th}$ Ed., (Wiley, John P. & Sons, NY:NY), Chapter 4, (1992).

Miller, R., et al., "A Convenient Synthesis of Pyrrole–2, 5–dicarboxaldehyde", *Acta. Chem. Scand. B*, vol. 35, pp. 303–304 (1981).

Pu, Y., et al., "Synthesis and Acylation of Salts of L–Threonine β–Lactone: A Route to β–Lactone Antibiotics", *J. Org. Chem.*, vol. 56, pp. 1280–1283 (1991).

Sandven, P., "Detection of Fluconazole–Resistant *Candida* Strains by a Disc Diffusion Screening Test", *J. of Clin. Microbiol.*, vol. 37, No. 12, pp. 3856–3859 (1999).

Willliams, R.M., et al., "Asymmetric Synthesis of Mono–substituted and α,α–Disubstituted α–Amino Acids via Diastereoselective Glycine Enolate Alkylations", *J. Amer. Chem. Soc.*, vol. 113, pp. 9276–9286 (1991).

International Search Report in related PCT application No. PCT/US01/20334, mailed May 15, 2002.

Bartulewicz, D., et al., "Synthetic Analogues of Netropsin and Distamycin–Synthesis of a New Pyridine and Carbocyclic Analogues of the Pyrrolecarboxamide antitumor antibiotics", *Acta Biochimica Polonica*, vol. 45, No. 1, pp. 41–57 (1998).

Bielawski, K., et al., "Synthetic Analogues of Netropsin and Distamycin III Synthesis of a Pyridine Analgue of the Pyrrolecarboxamide Antitumor Antibiotics", *Roczniki Akademii Medycznej w Bialymstoku*, vol. 41, No. 2, pp. 293–304 (1996).

Chowdhury, AK, et al., "Synthesis and Evaluation of Bix-Dipeptide and Bis–Tripeptide Analogues of Actinomycin D", *Jol. of Medicinal Chem.*, vol. 21, No. 7, pp. 607–612 (1978).

Yavorskaya, NP, et al., "Search for Antitumor Compounds Among Actinocin Derivatives", *Chem Abstract No. XP–002194807* (1997).

Bailly, Christian, et al., *Sequence–Specific DNA Minor Groove Binders. Design and Synthesis of Netropsin and Distamycin Analogues*, Bioconjugate Chemistry, vol. 9, No. 5, (Sep./Oct. 1998), pp. 513–538.

Chen, Yong–Huang, *Optimization of Cross–Linked Lexitropsins*, Journal of Biomolecular Structure & Dynamics, vol. 14, No. 3, (Nov. 3, 1996), pp. 341–355.

(List continued on next page.)

*Primary Examiner*—Kevin E. Weddington
(74) *Attorney, Agent, or Firm*—Foley & Lardner, LLP; Julie Yang

(57) ABSTRACT

The present invention provides novel compounds possessing one or more of the following activities: antibacterial, antifungal and antitumor activity. The compounds are of Formula (I):

$$R^1-Z^1-\overset{O}{\underset{}{\text{C}}}-X^1-\underset{H}{N}-\overset{O}{\underset{}{\text{C}}}-X^2-\overset{O}{\underset{}{\text{C}}}-\underset{H}{N}-X^3-\overset{O}{\underset{}{\text{C}}}-Z^2-R^2$$

Pharmaceutical compositions containing these compounds, methods of making and methods for using these compounds are also provided.

17 Claims, 26 Drawing Sheets

OTHER PUBLICATIONS

Filipowsky, Mark E., et al., *Linked Lexitropsins and the in Vitro Inhibition of HIV–1 Reverse Transcriptase RNA–Directed DNA Polymerization: A Novel Induced–Fit of 3:5 m–Pyridyl Bisdistamycin to Enzyme–Associated Template–Primer*, Biochemistry, (Dec. 3, 1996), 35:40, pp. 15399–15410.

Fishleigh, Robert V. et al., *DNA Binding, Solubility, and Partitioning Characteristics of Extended Lexitropsins*, J. Med. Chem., 43, (2000), pp. 3257–3266.

Kissinger et al., Chem. Res. Toxicol., 3(2), (1990), pp. 162–168.

Lown, J. William et al., *Novel Linked Antiviral and Antitumor Agents Related to Netropsin and Distamycin: Synthesis and Biological Evaluation*, J. Med. Chem, 32:10, (1989), pp. 2368–2375.

Neamati, Nouri et al., *Highly Potent Synthetic Polyamides, Bisdistamycins, and Lexitropsins as Inhibitors of Human Immunodeficiently Virus Type 1 Integrase*, Molecular Pharmacology, 54, (1998), pp. 280–290.

Reddy, B.S. Praveen et al., *Synthetic DNA Minor Groove-Binding Drugs*, Pharmacology & Therapeutics, 84. (1999), pp. 1–111.

Sharma, Sanjay K., *Designs and Synthesis of Novel Thiazole–Containing Cross–Linked Polyamides Related to the Antiviral Antibiotic Distamycin*, J. Org. Chem., 65, (2000), pp. 1102–1107.

Wang, Z., et al., Biochem. Pharmacol., 53, (1997), pp. 309–316.

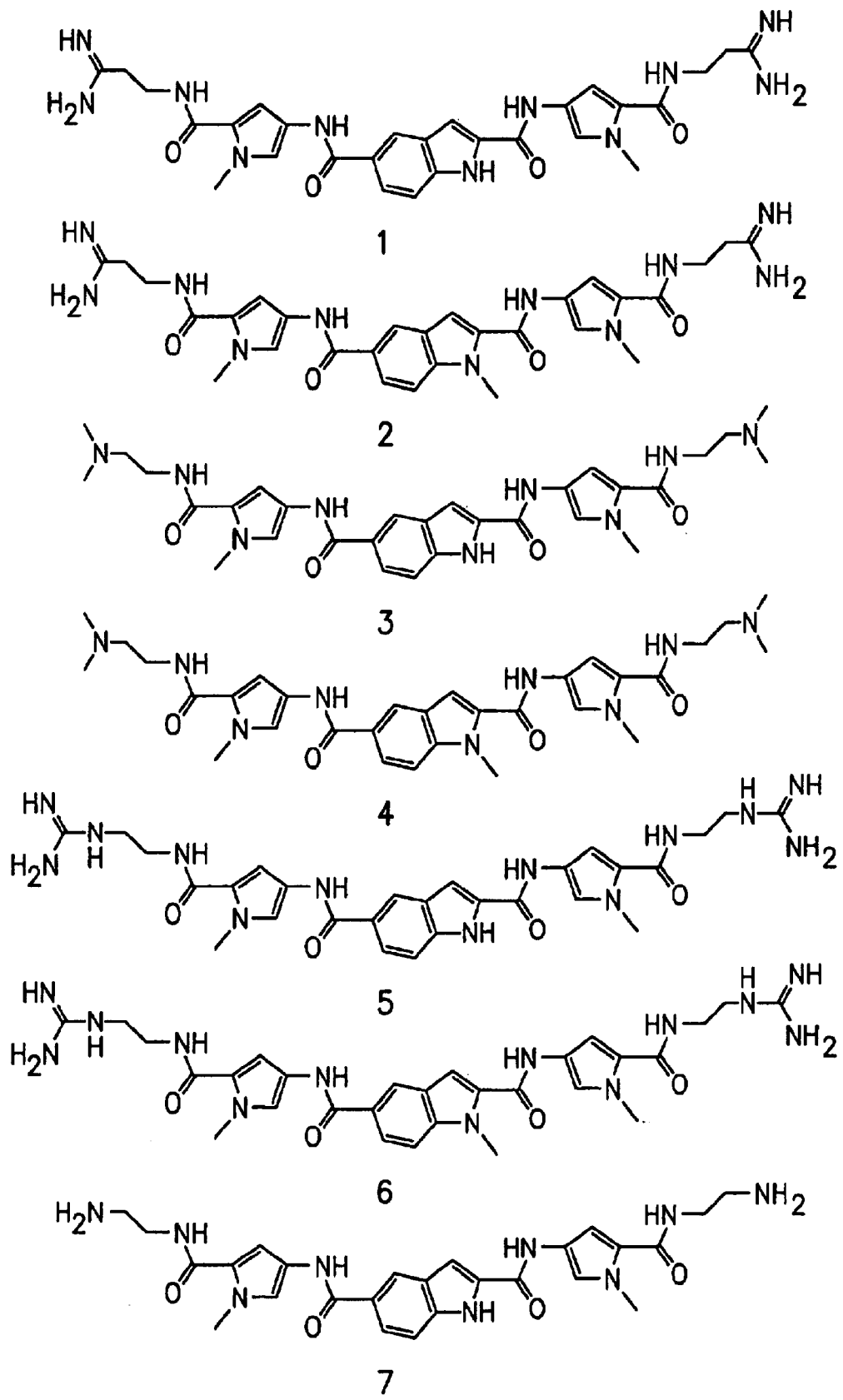
FIG. 1-A

FIG. 1-B
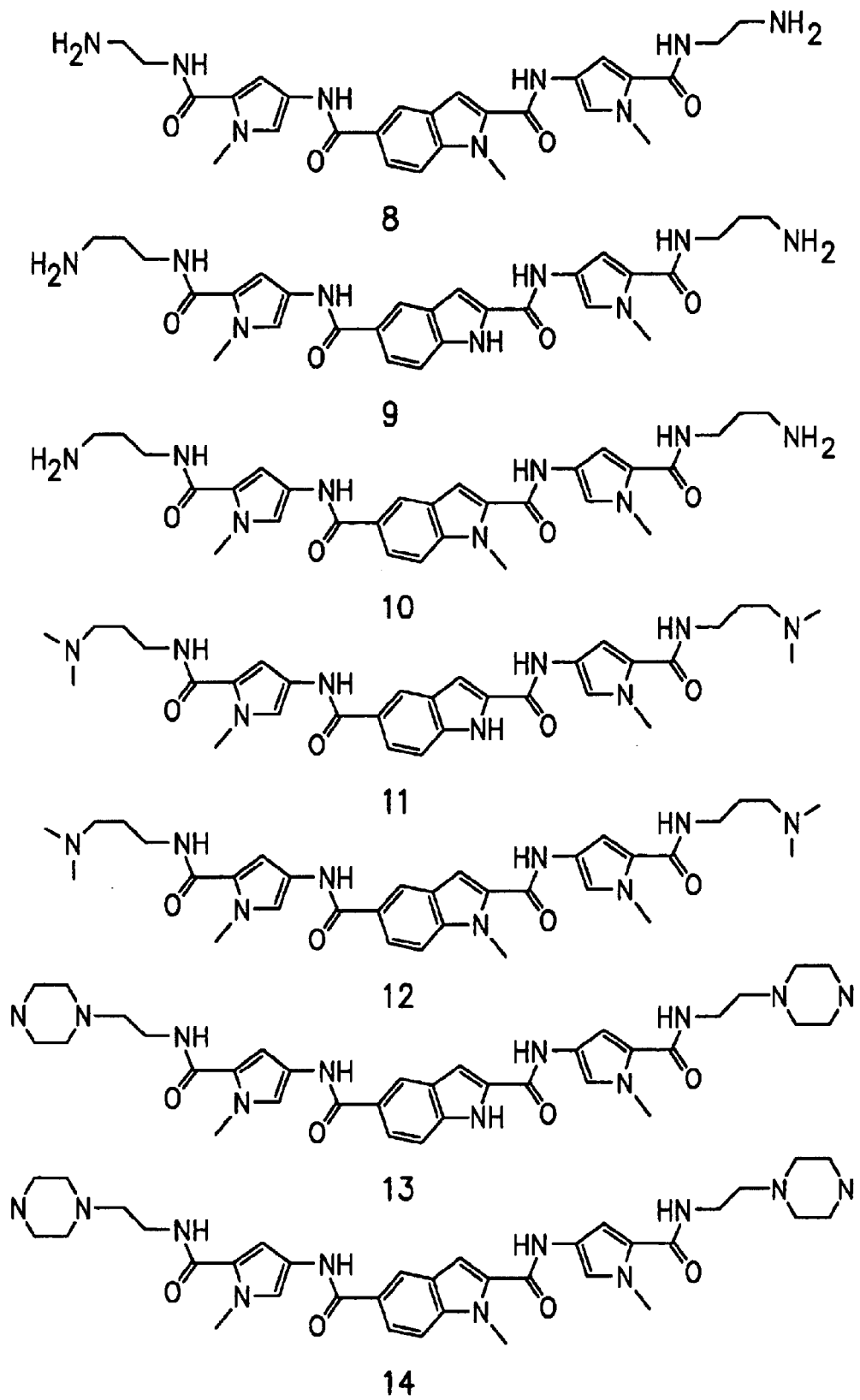

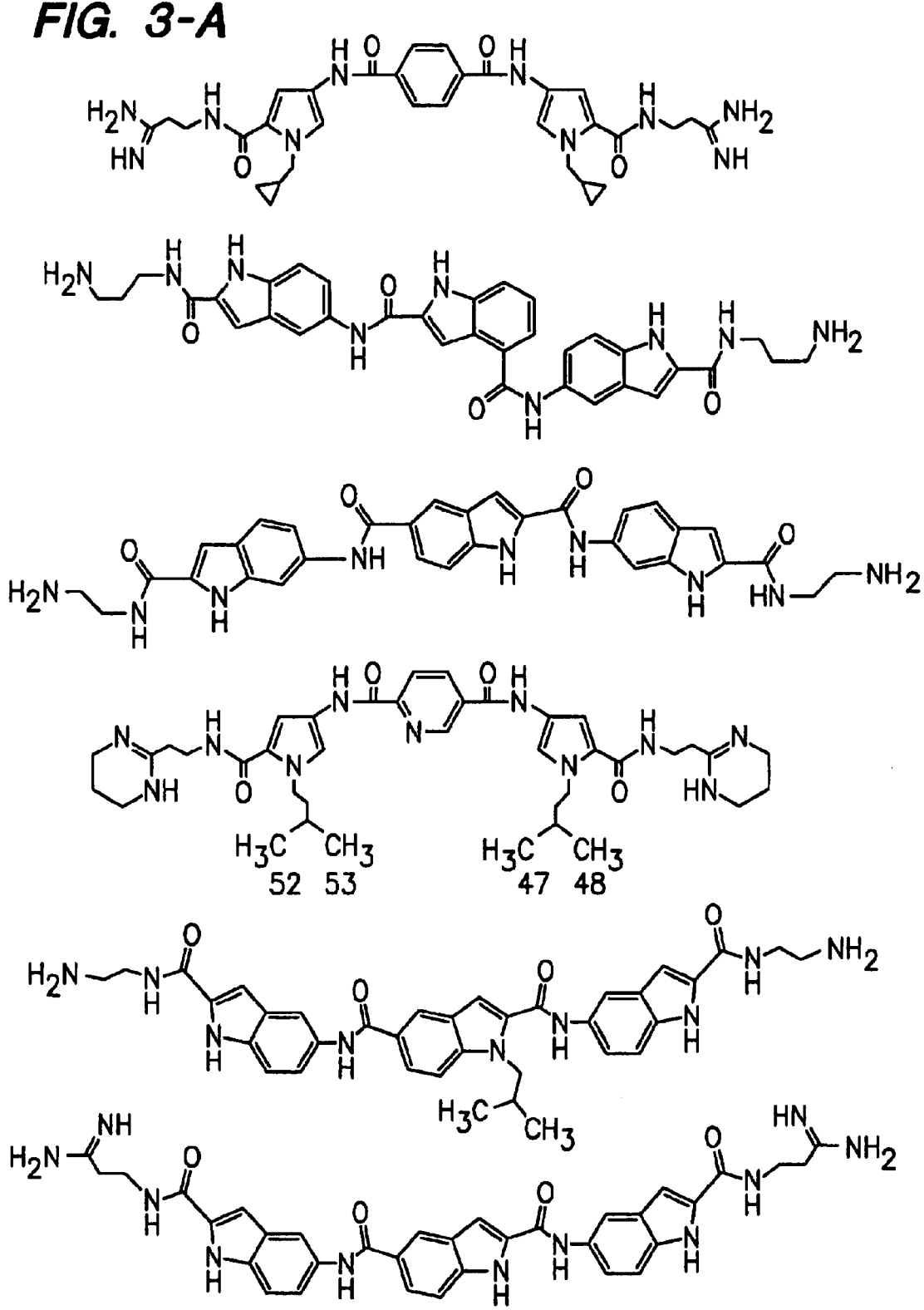
FIG. 3-A

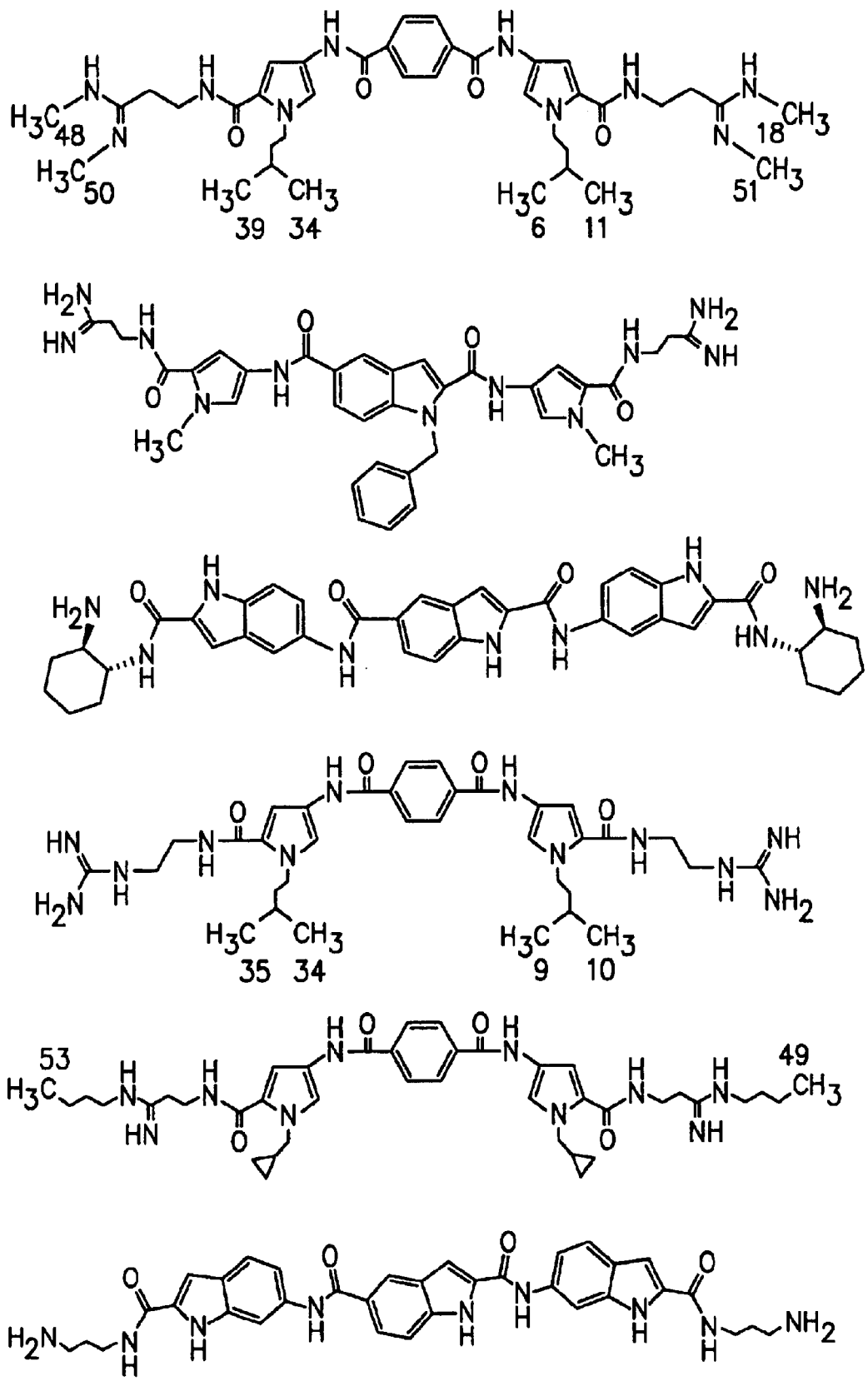
FIG. 3-B

*FIG. 3-C*
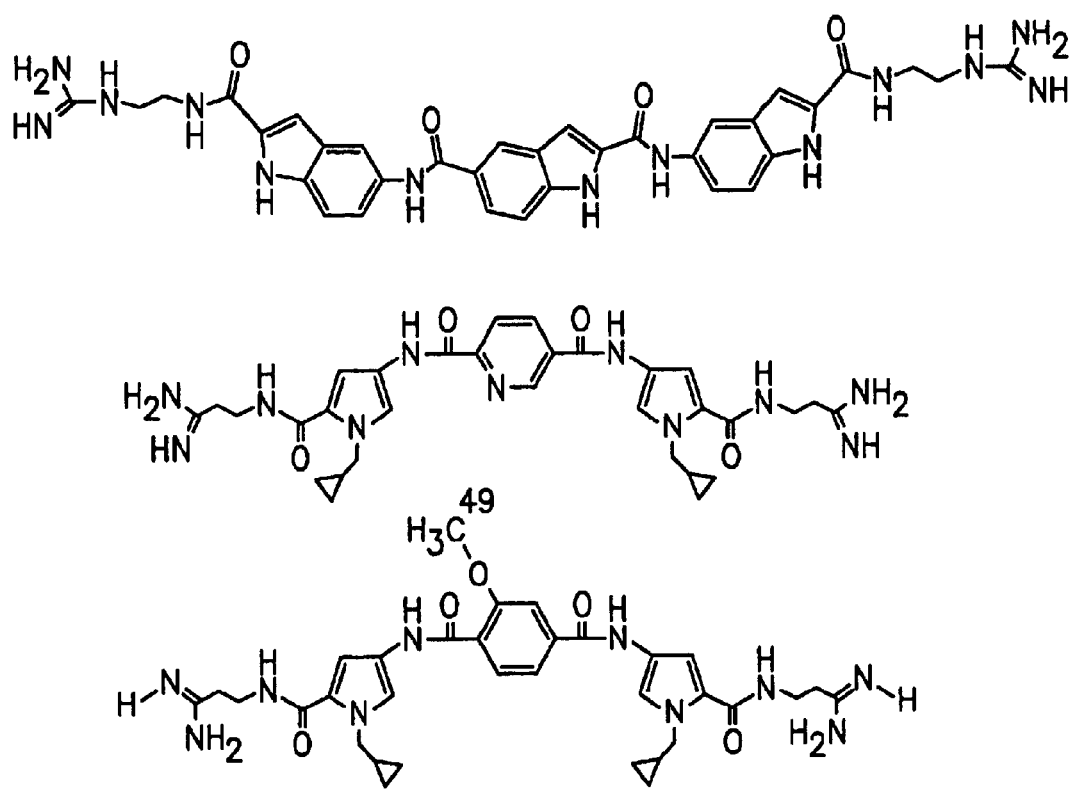

FIG. 4-A
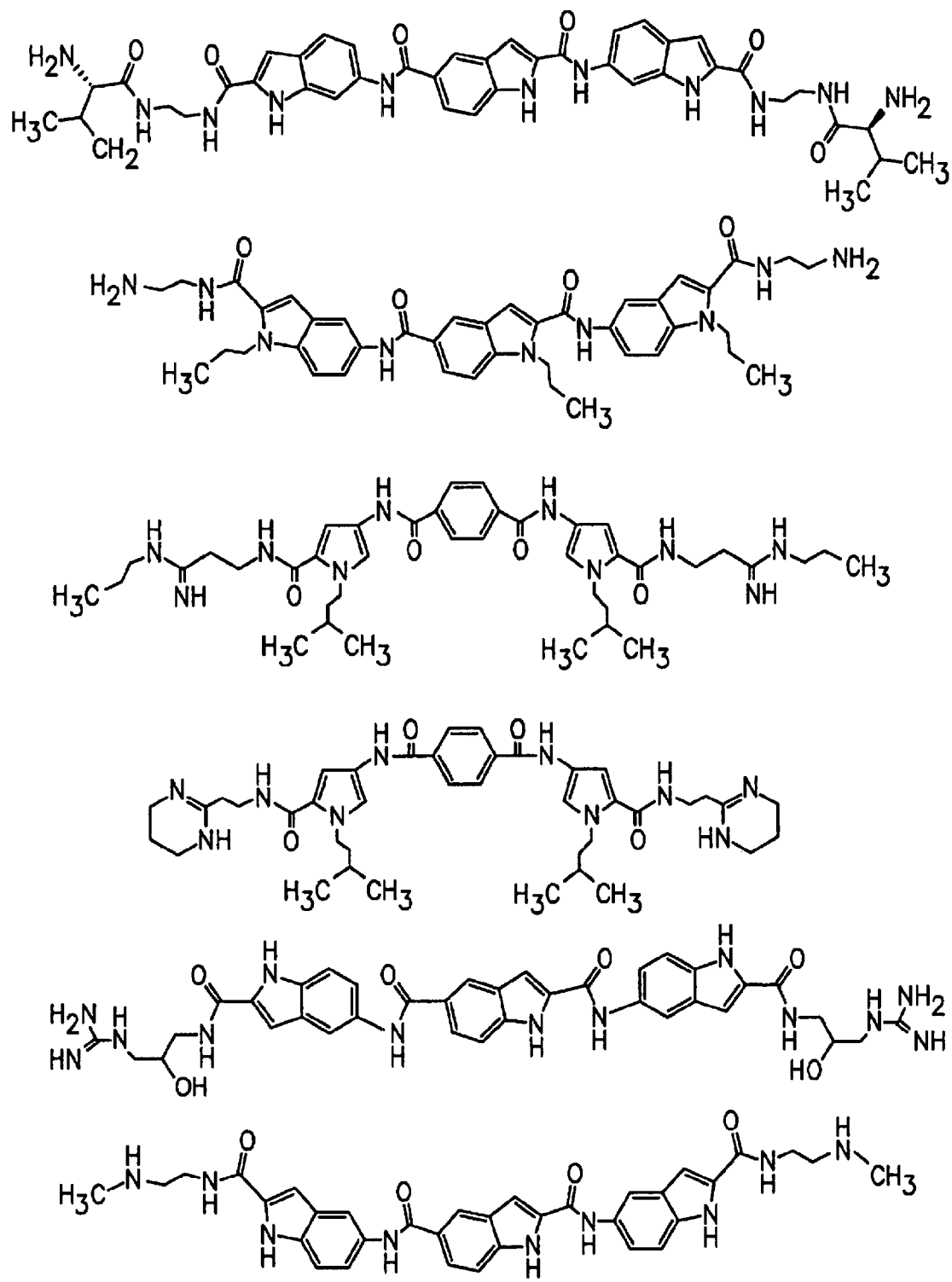

FIG. 4-B
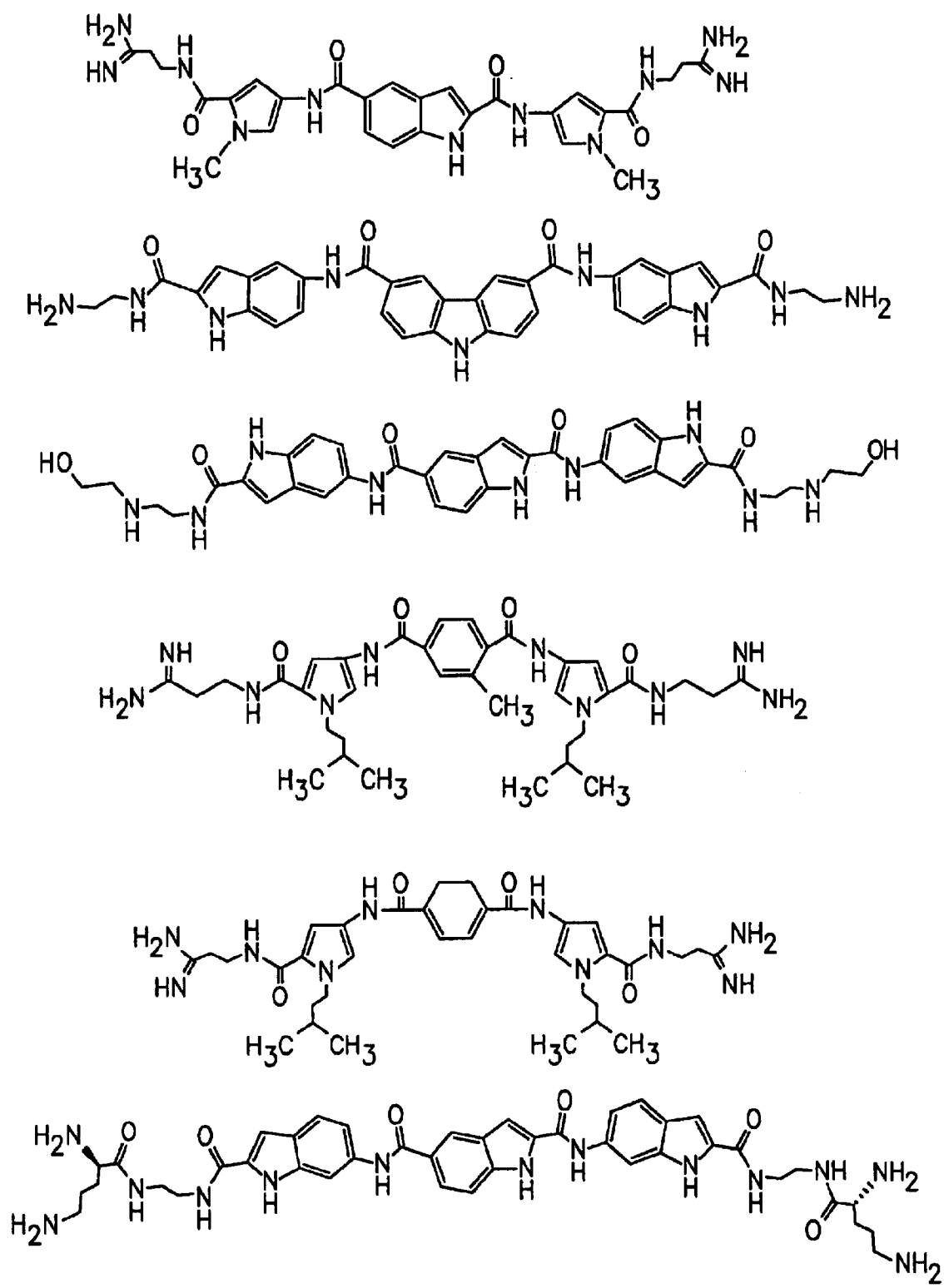

FIG. 5-A
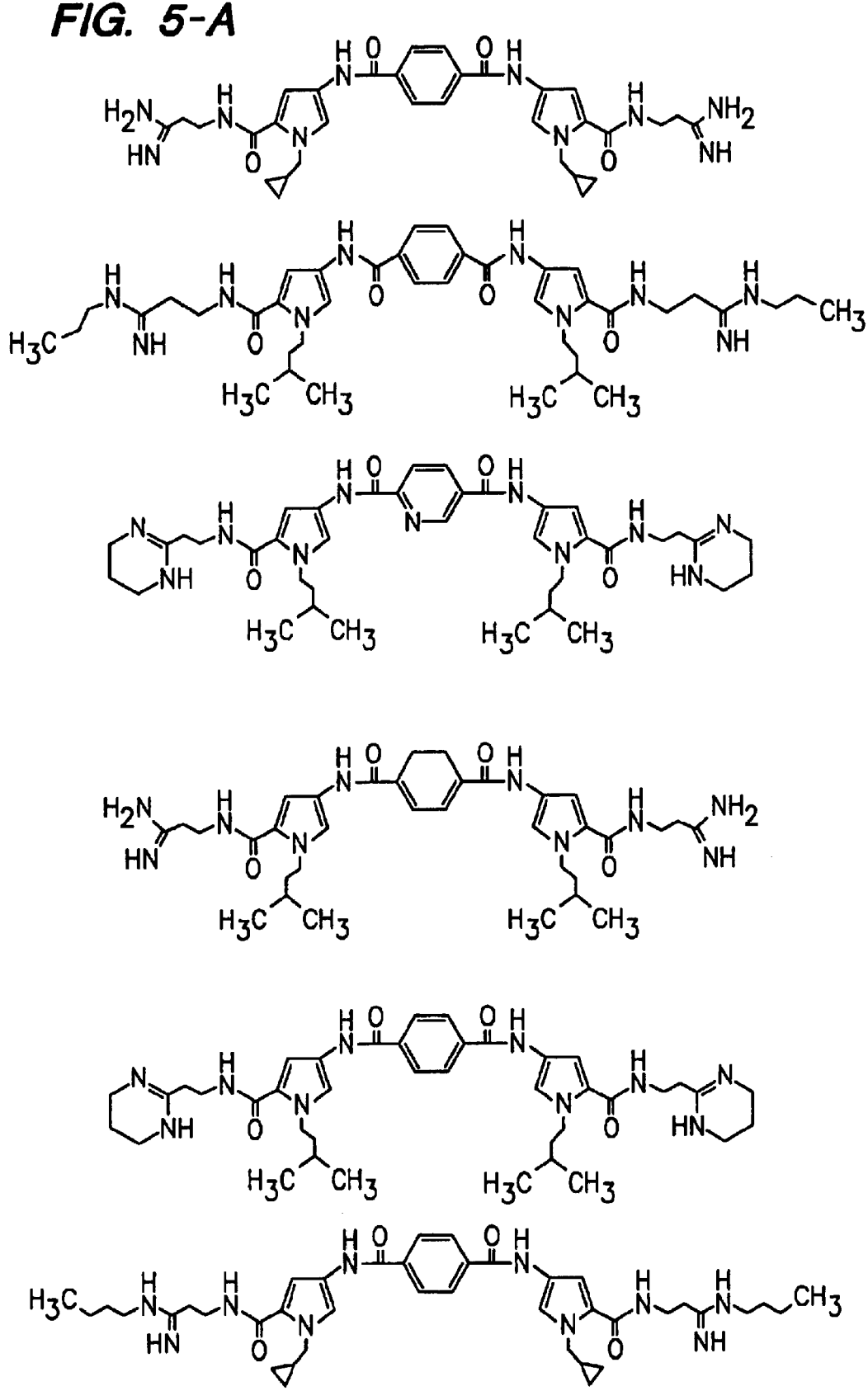

FIG. 5-B
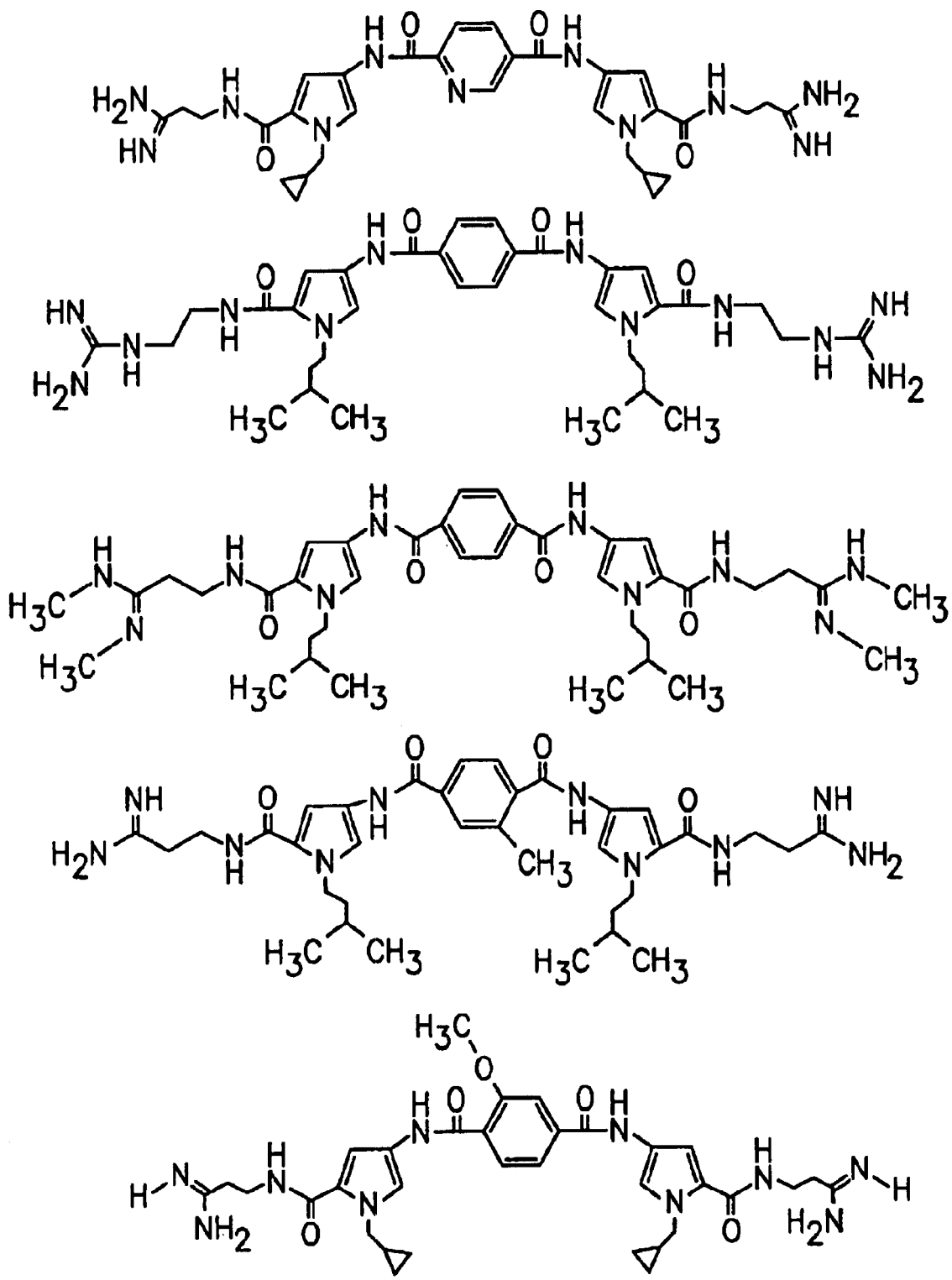

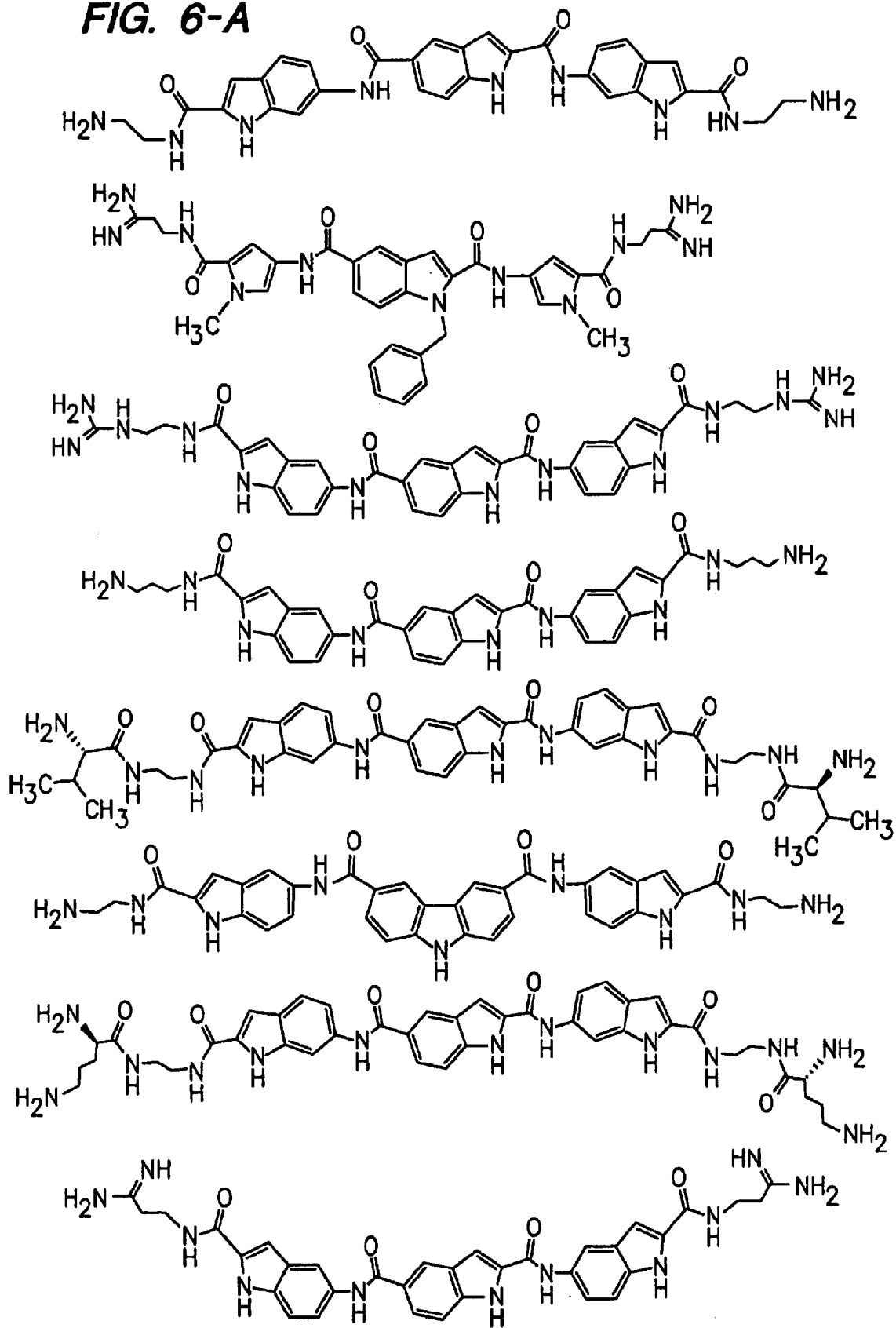
FIG. 6-A

FIG. 6-B
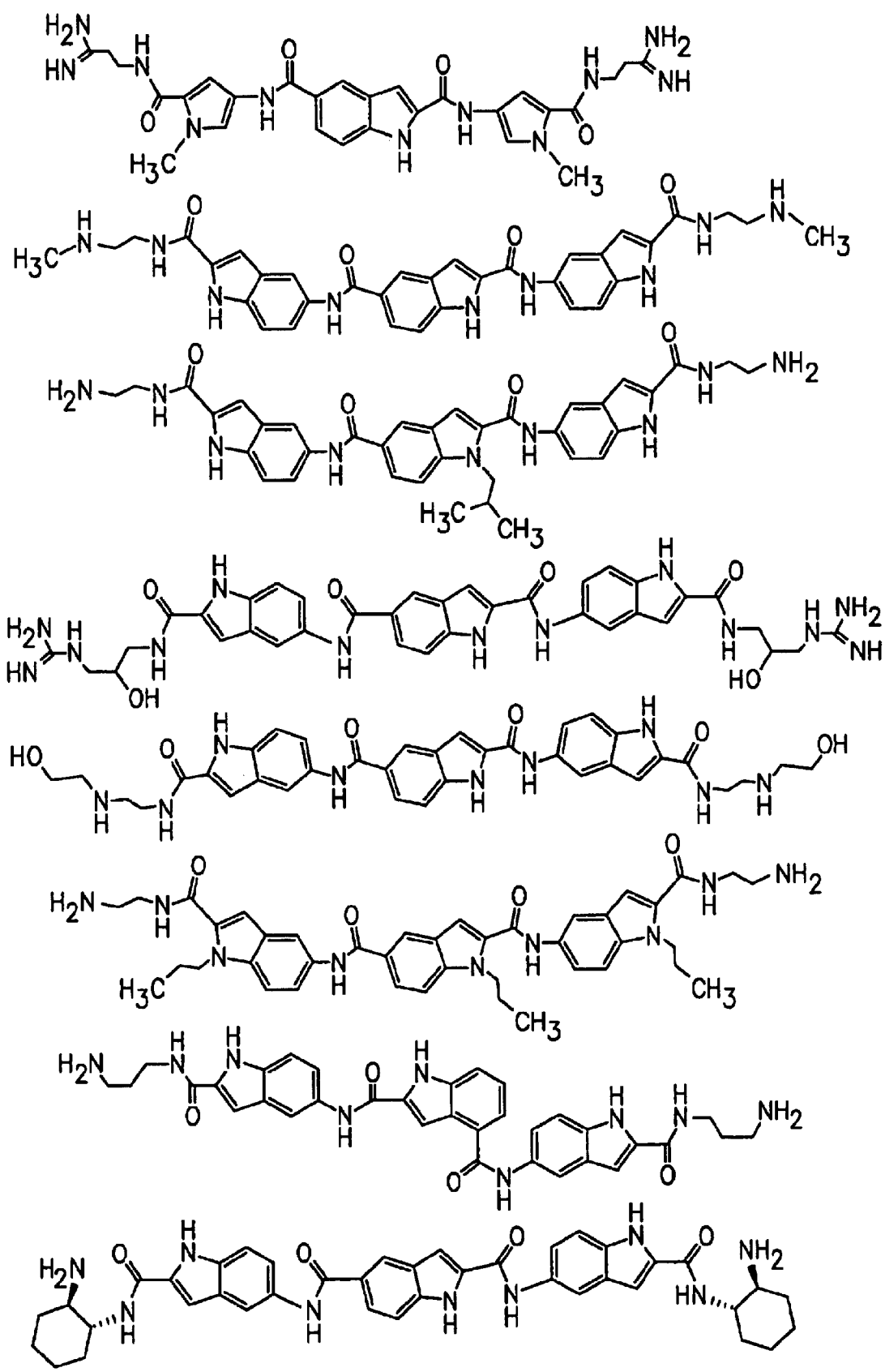

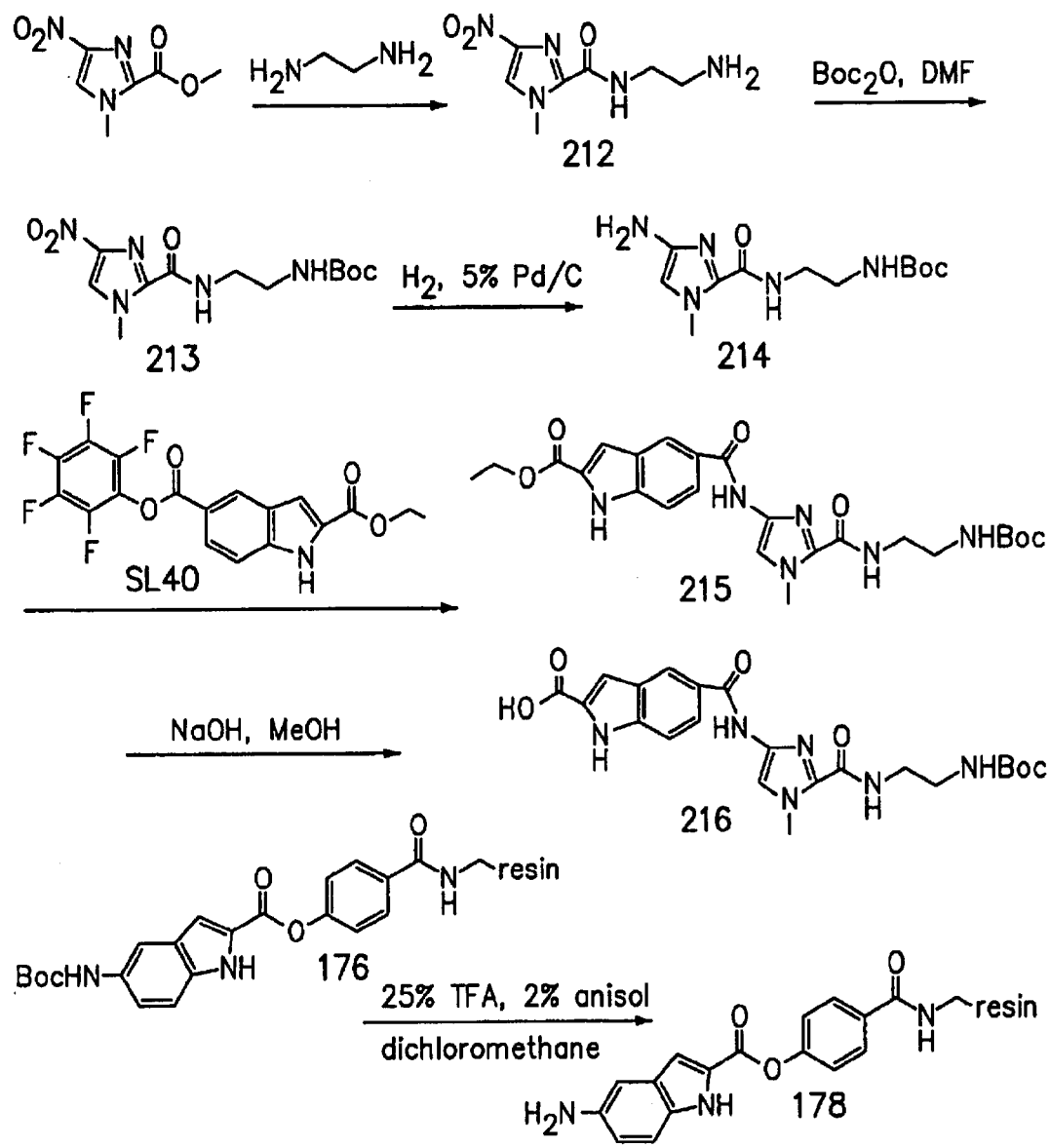
FIG. 16-A

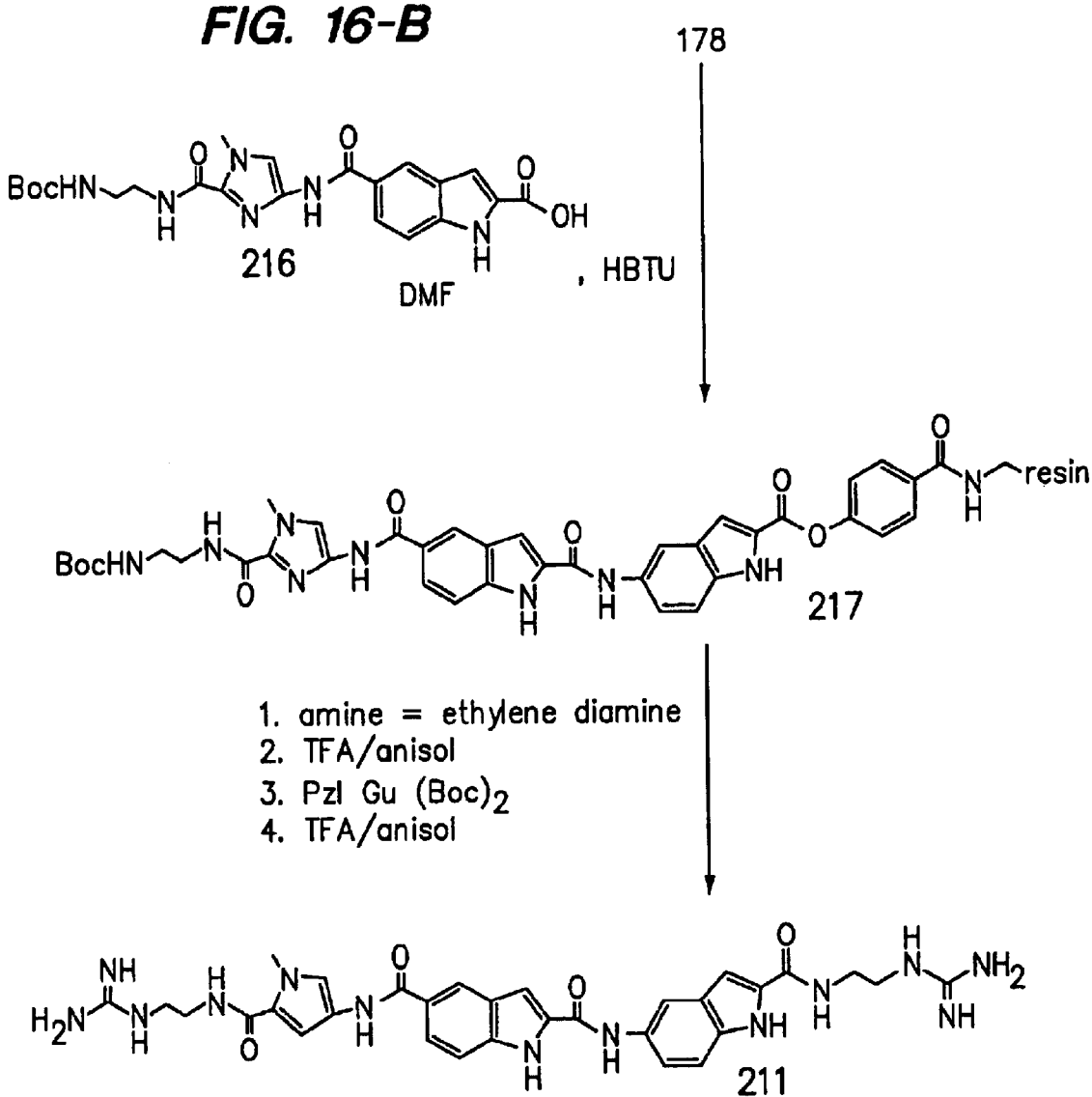
FIG. 16-B

COMPOUNDS POSSESSING ANTIBACTERIAL, ANTIFUNGAL OR ANTITUMOR ACTIVITY

CROSS-REFERENCE TO RELATED APPLICATIONS

This application claims priority under 35 U.S.C. 119(e) to U.S. Provisional Application Serial No. 60/214,478, which was filed on Jun. 27, 2000, the disclosure of which is incorporated herein in its entirety.

BACKGROUND OF THE INVENTION

1. Field of Invention

The present invention provides novel compounds possessing one or more of the following activities: antibacterial, antifungal and antitumor activity. Pharmaceutical compositions containing these compounds, methods of making and methods for using these compounds are also provided.

2. State of the Art

The binding of the antibacterial netropsin and distamycin to AT-rich sequences in the minor groove of double stranded DNA is a well studied phenomenon. Because such binding can be used to regulate DNA expression, e.g., by blocking and/or displacement of regulatory proteins, or by inhibiting the activity of enzymes acting on DNA, such as reverse transcriptase or topoisomerase, optimization of this binding has been the subject of numerous recent studies.

As described in a recent review by Bailly and Chaires (*Bioconj. Chem.* 9(5):513–38, 1998), the pyrrolecarboxamide unit in netropsin and distamycin is actually about 20% longer than required to perfectly match the corresponding base pair sequence in the minor groove. Accordingly, in oligomeric analogs having multiple binding moieties, successive binding moieties can become out of phase with the base pairs of the minor groove. Several studies have therefore been directed to dimers of netropsin or distamycin containing different linkers, in order to improve binding to longer target sequences. In these reports, effectiveness of various netropsin or distamycin dimers was determined, for example, in the inhibition of transcription by HIV-1 reverse transcriptase (M. Filipowsky et al, *Biochemistry* 35:15397–410, 1996), inhibition of mammalian DNA topoisomerase I (Z. Wang et al., *Biochem. Pharmacol.* 53:309–16, 1997), or inhibition of HIV 1 integrase (N. Neamati et al, *Mol. Pharmacol.* 54:280–90, 1998).

Preferred linkers in these studies included p-phenylene, trans-vinyl, cyclopropyl, 3,5-pyridyl, and six- and eight-carbon aliphatic chains. Several of these linkers restrict rotation around the linking group, thus reducing the extent of purely monodentate binding (e.g. by only one netropsin moiety; see Bailly) which can occur with flexible linkers. However, Kissinger et al. (*Chem. Res. Toxicol.* 3(2):162–8, 1990) reported that aryl-linked groups had reduced DNA binding affinity compared to alkyl and alkylene linkers, and Neamati et al. (cited above) reported that the trans-vinyl linked compound was many times more potent (in inhibiting HIV-1 integrase) than the "more rigid" cyclobutanyl and norbornyl linkers. It was suggested in Wang and in Bailly that, for certain applications, the more rigid linkers (cyclopropyl and p-phenylene) may not allow for optimal simultaneous (bidentate) binding of the two netropsin moieties flanking the linker. Therefore, it would be desirable to provide linkers which reduce monodentate binding but which provide suitable geometries for bidentate binding. In light of the increase of antibiotic/antifungal resistant organisms, there is a need to develop new compounds to treat diseases caused by these antibiotic/antifungal resistant organisms. The compounds of the present invention fulfill this need.

SUMMARY OF THE INVENTION

The present invention provides novel compounds which possess one or more of the following activities: antibacterial, antifungal and antitumor activity. Specifically, the compounds of this invention are represented in Formula (I) below:

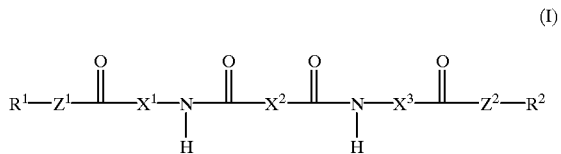

(I)

wherein:

$Z^1$ and $Z^2$ are independently —$NR^3$-(wherein $R^3$ is hydrogen or alkyl) or —O—;

$R^1$ and $R^2$ are independently substituted alkyl, substituted aryl, heteroaryl, or substituted heteroaryl provided that at least one of $R^1$ and $R^2$ is a group that can form a pharmaceutically acceptable acid addition salt;

$R^3$ is hydrogen, alkyl or $R^3$ and $R^1$ or $R^2$ together with the atoms to which they are attached form a heterocyclic ring;

$X^2$ is aryl, substituted aryl, heteroaryl, substituted heteroaryl, alkenyl, alkynyl, cycloalkyl or heterocyclic;

$X^1$ and $X^3$ are independently aryl, substituted aryl, heteroaryl or substituted heteroaryl;

or a pharmaceutically acceptable acid addition salt thereof.

In a second aspect, this invention is directed to a method of treating bacterial and/or fungal infection(s), which method comprises administration of a therapeutically effective amount of a compound of Formula (1) or a pharmaceutically acceptable an acid addition salt thereof.

In a third aspect, this invention is directed to a method of treating cancer through the inhibition of topoisomerase, which method comprises administration of a therapeutically effective amount of a compound of Formula (I) or a pharmaceutically acceptable an acid addition salt thereof.

In a fourth aspect, this invention is directed to pharmaceutical compositions containing a therapeutically effective amount of a compound of Formula (I) or a pharmaceutically acceptable acid addition salt thereof and a pharmaceutically acceptable excipient.

BRIEF DESCRIPTION OF THE DRAWINGS

FIGS. 1A and 1B are collectively referred to as FIG. 1 throughout the specification and each illustrates some representative compounds of this invention.

FIGS. 3A–C are collectively referred to as FIG. 3, and FIGS. 4A–B are collectively referred to as FIG. 4, throughout the specification and each illustrate even further representative compounds of this invention.

FIGS. 5A and 5B are collectively referred to as FIG. 5 throughout the specification and each illustrates examples of compounds possessing antibacterial activity.

FIGS. 6A and 6B are collectively referred to as FIG. 6 throughout the specification and each illustrates examples of compounds possessing antifungal activity.

FIGS. 16A and 16B are collectively referred to as Scheme 10.

DETAILED DESCRIPTION OF THE INVENTION

Figure 2:
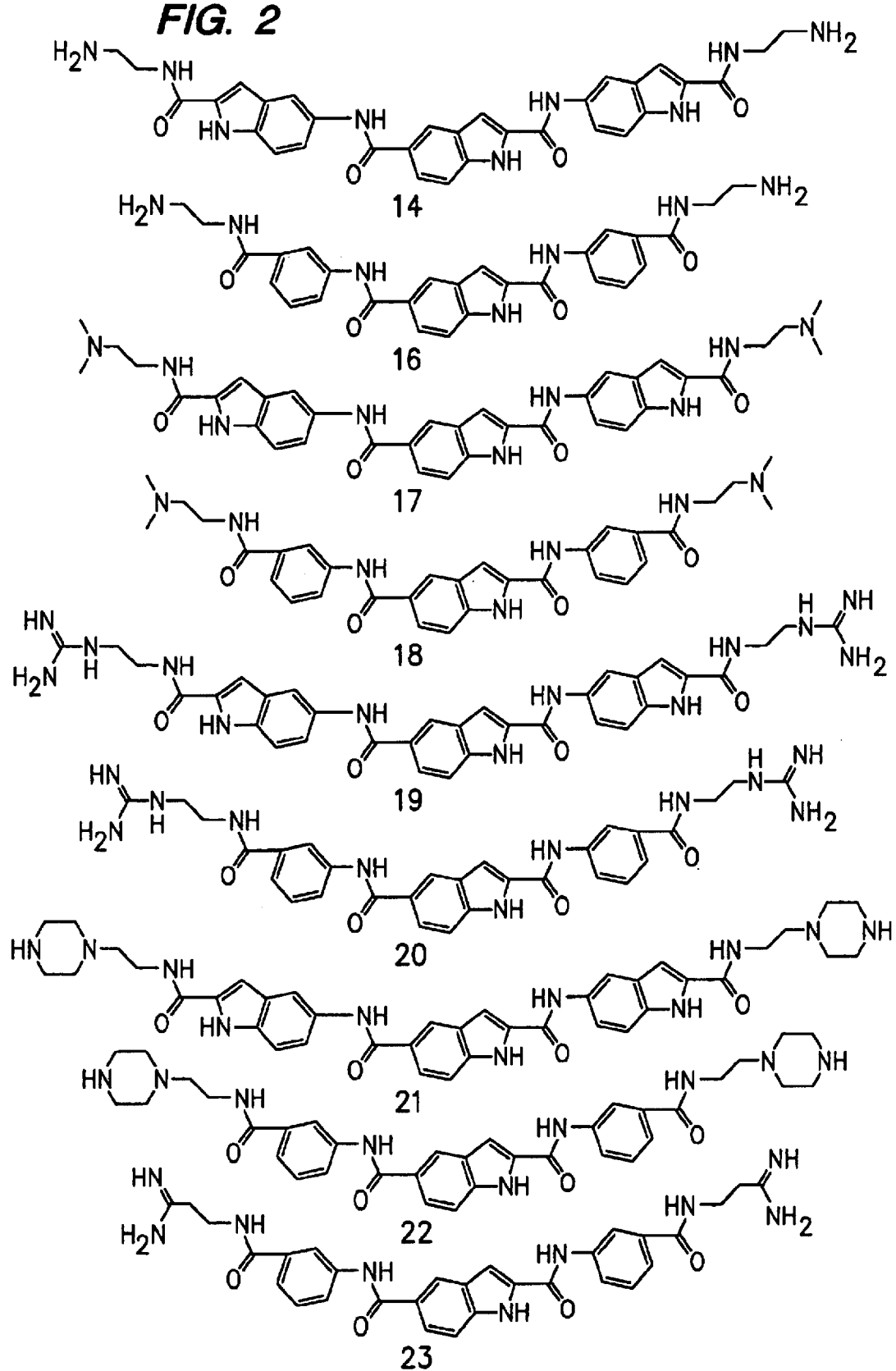
FIG. 2 illustrates further representative compounds of this invention.
Figure 7:
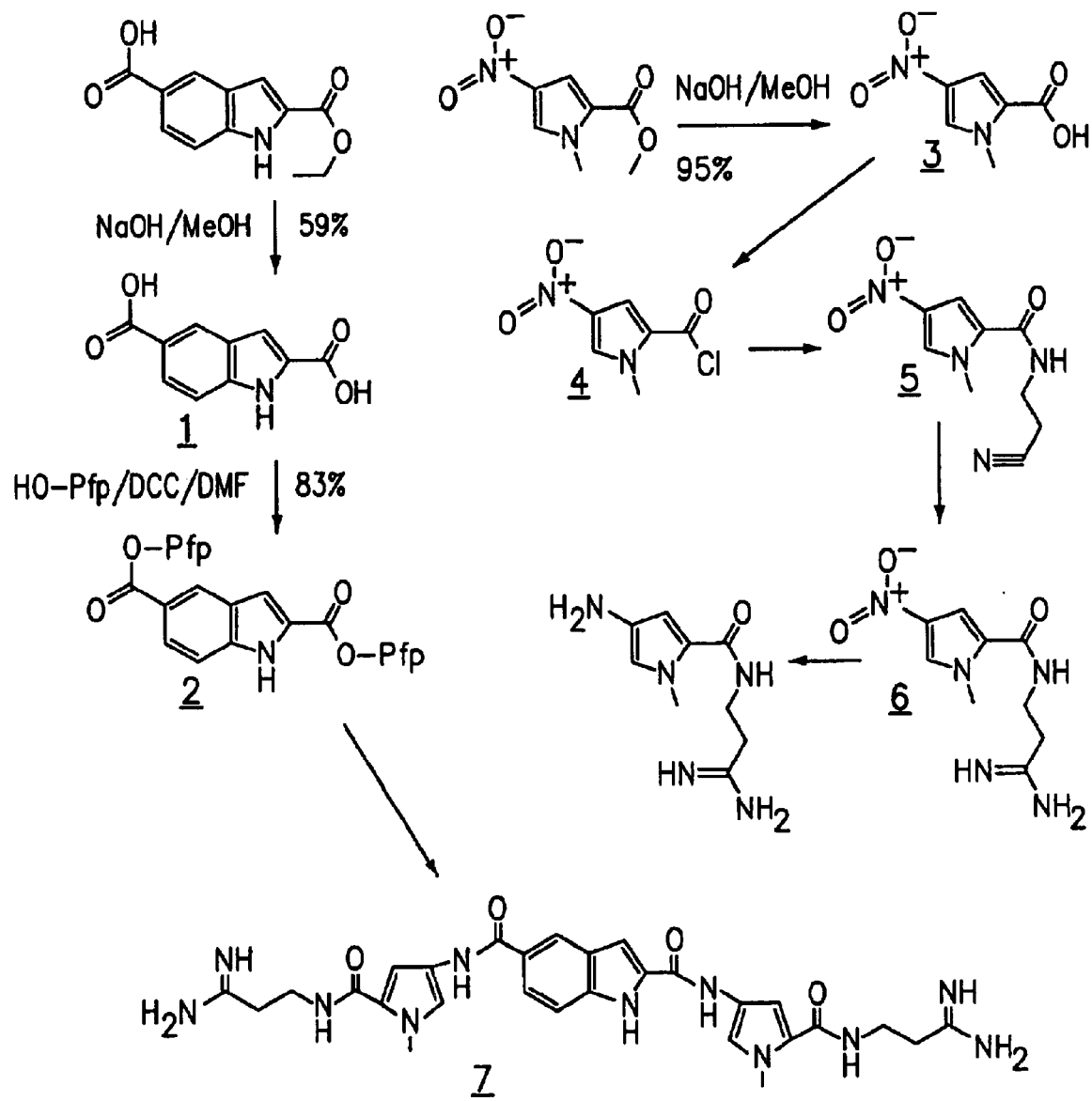
FIGS. 7–11 are referred to as Schemes 1–5, respectively, throughout the specification and each illustrate synthetic routes to compounds 7, 11–15, 20, 22 and 25, which are compounds Formula (I).
Figure 8:
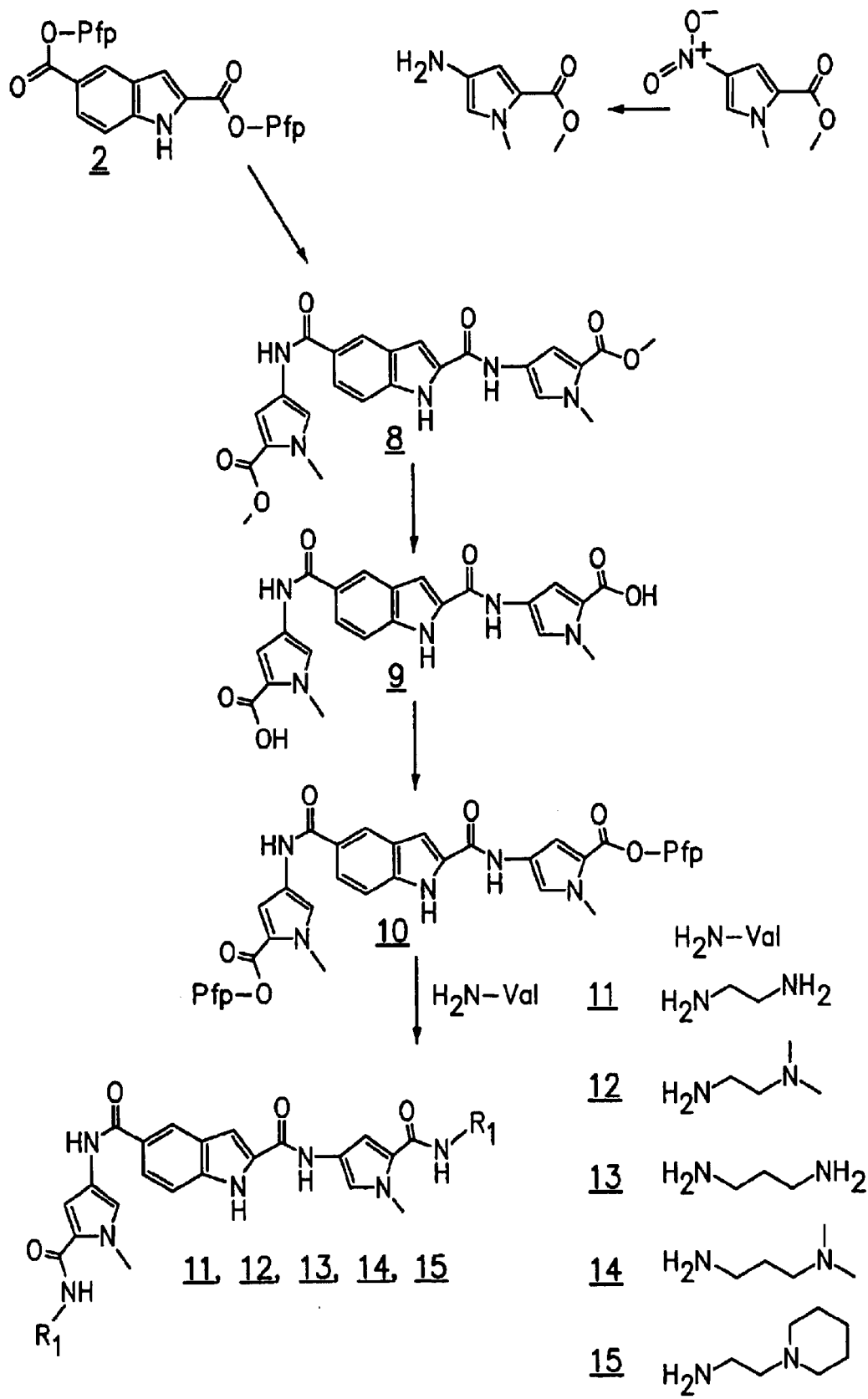
Figure 9:
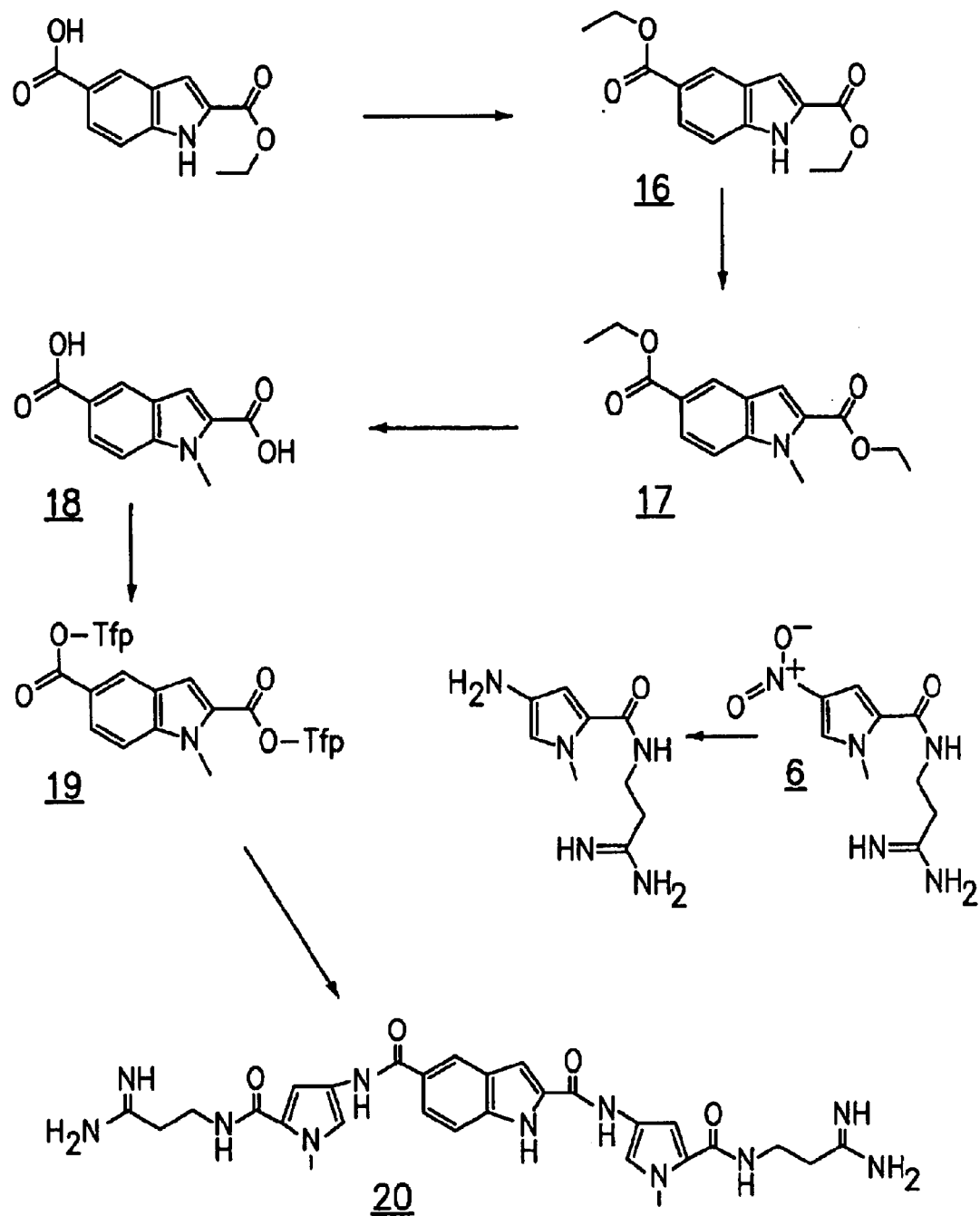
Figure 10:
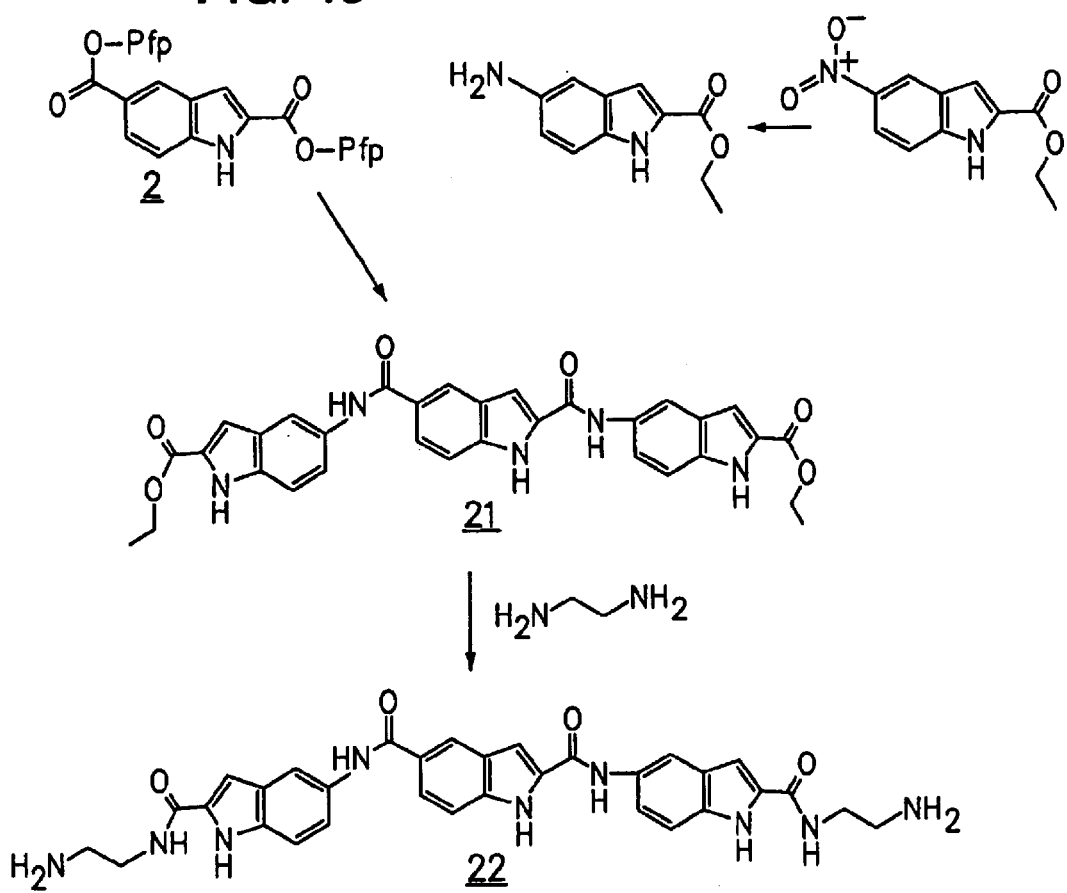
Figure 11:
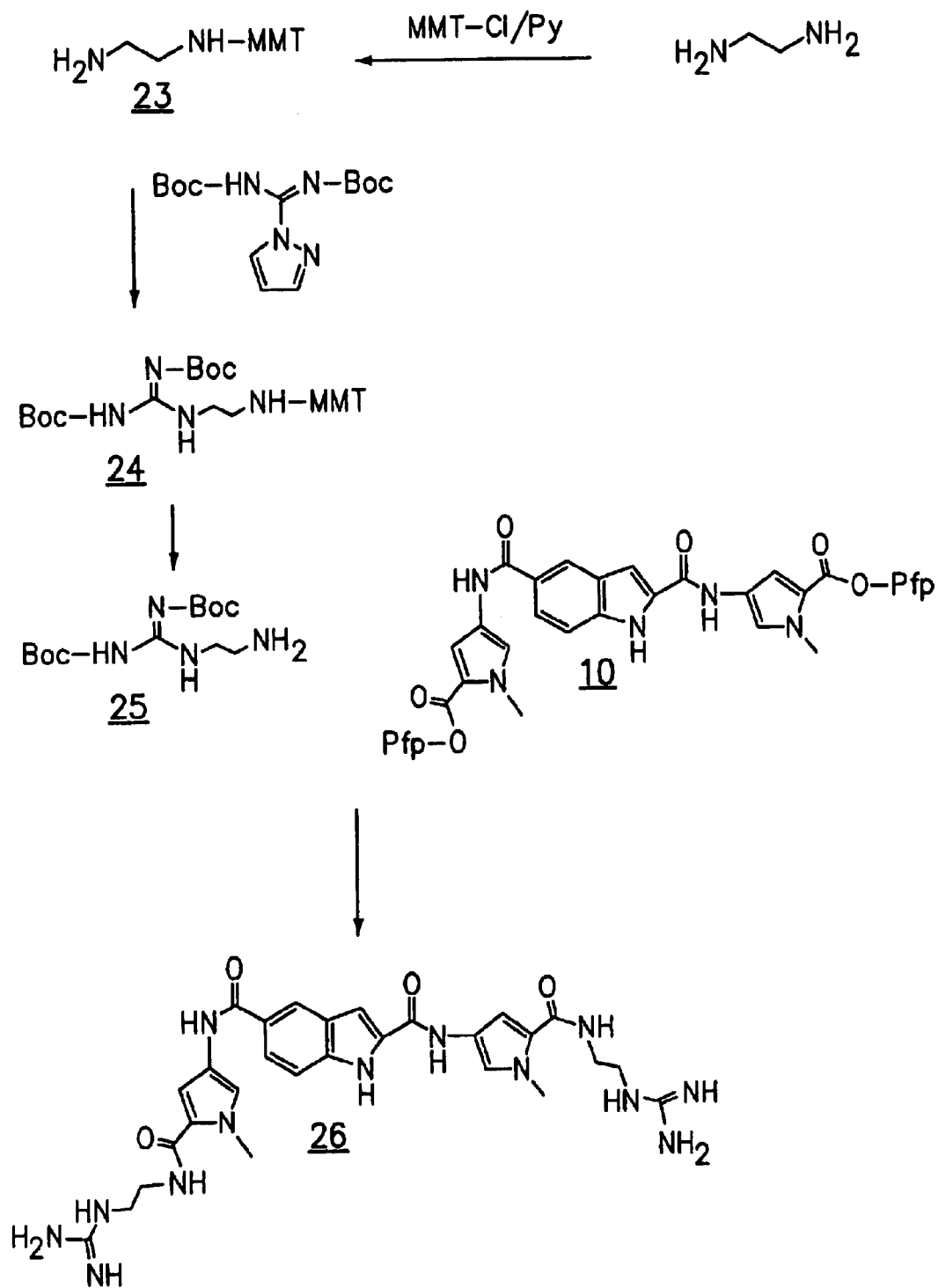
Figure 12:
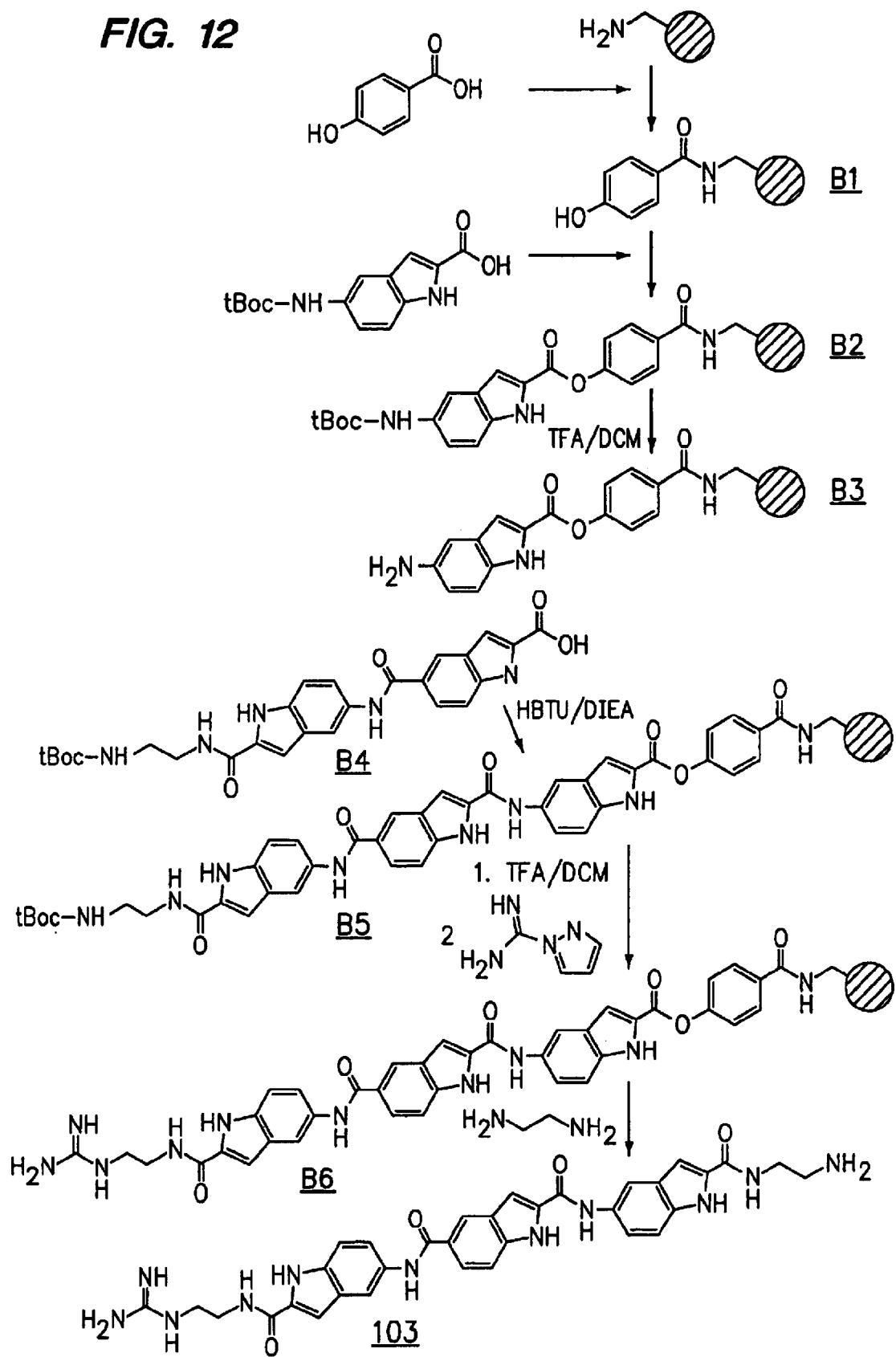
FIGS. 12–15 are referred to as Schemes 6–9, respectively.
Figure 13:
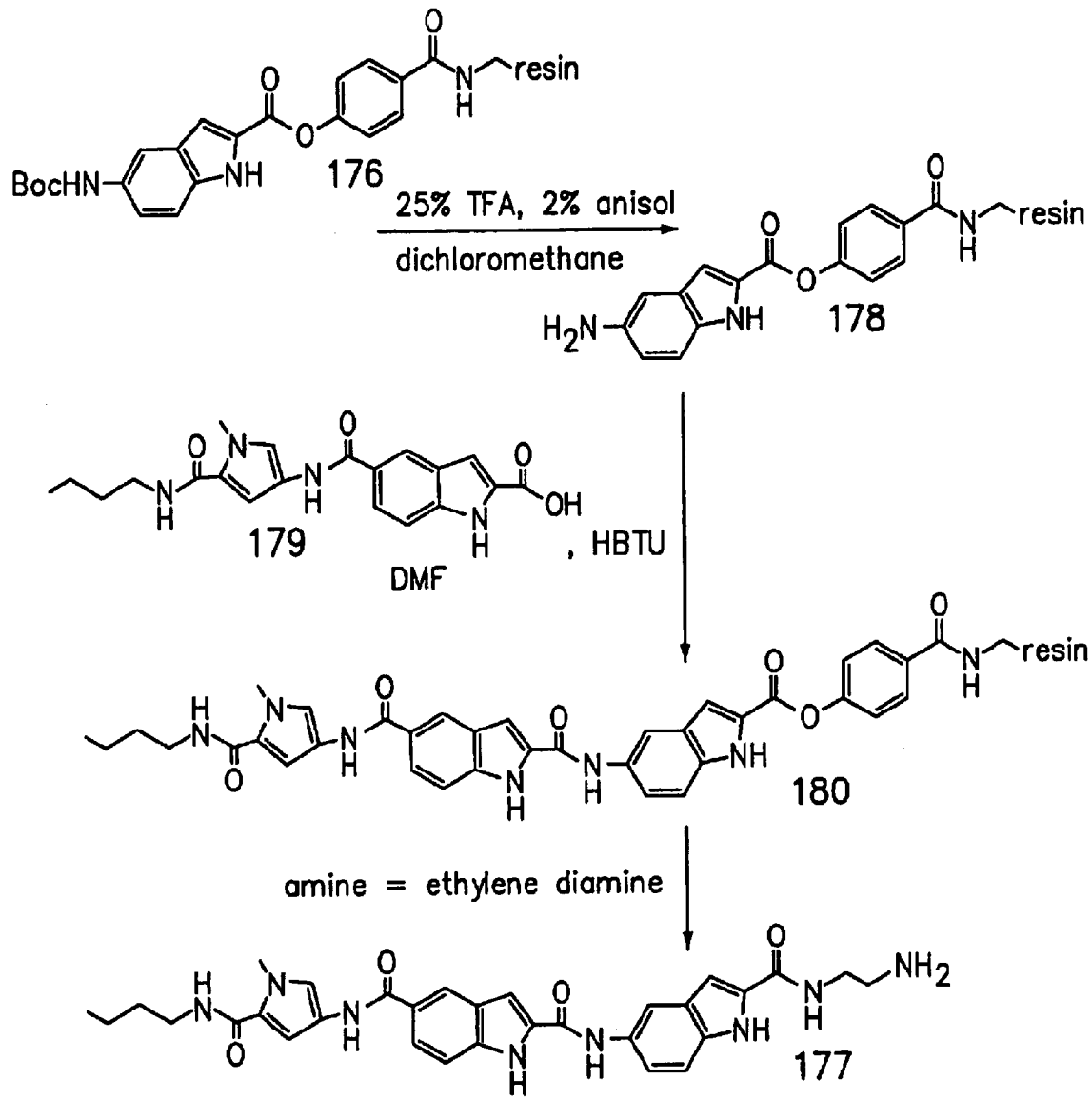
Figure 14:
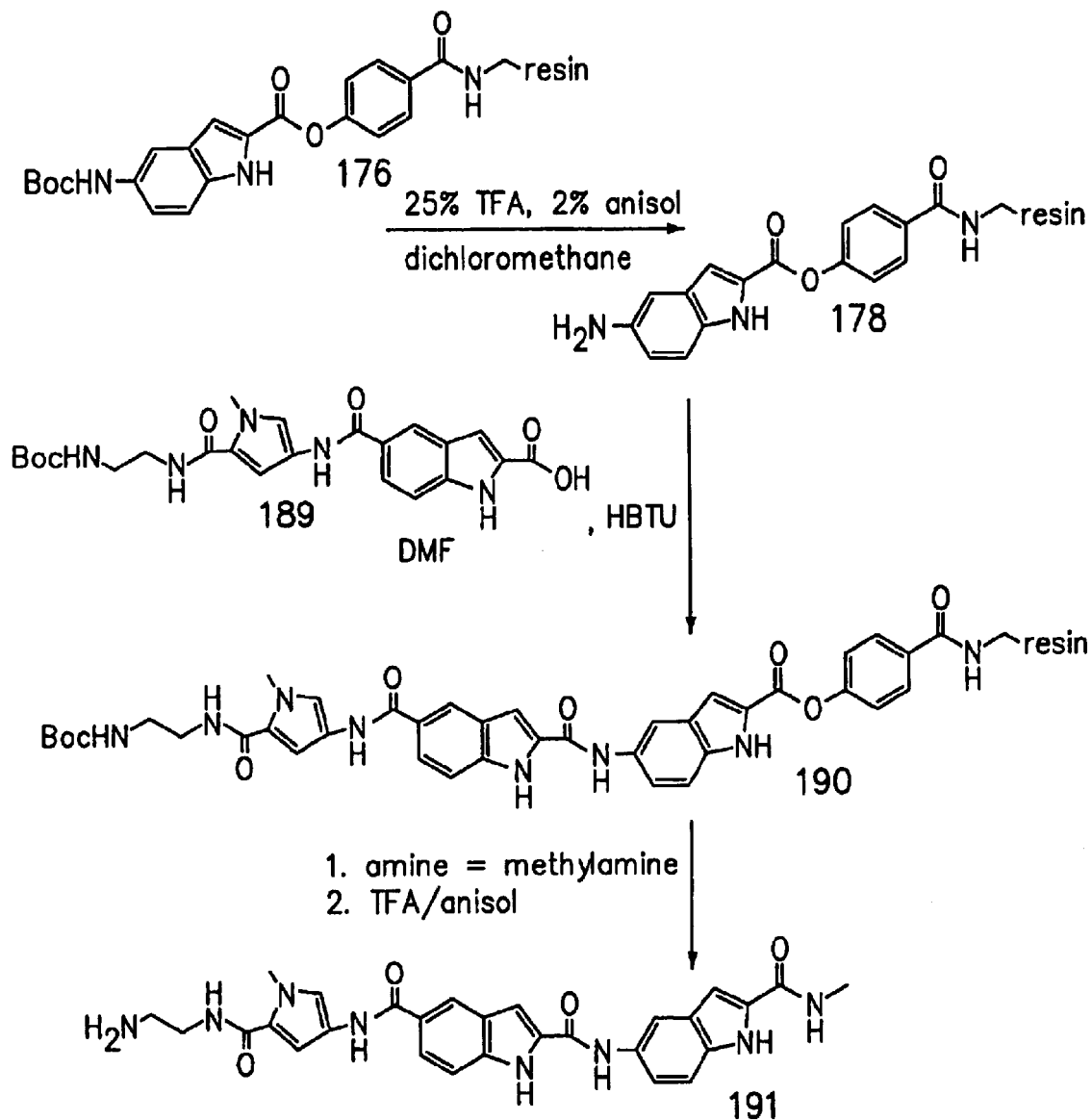
Figure 15:
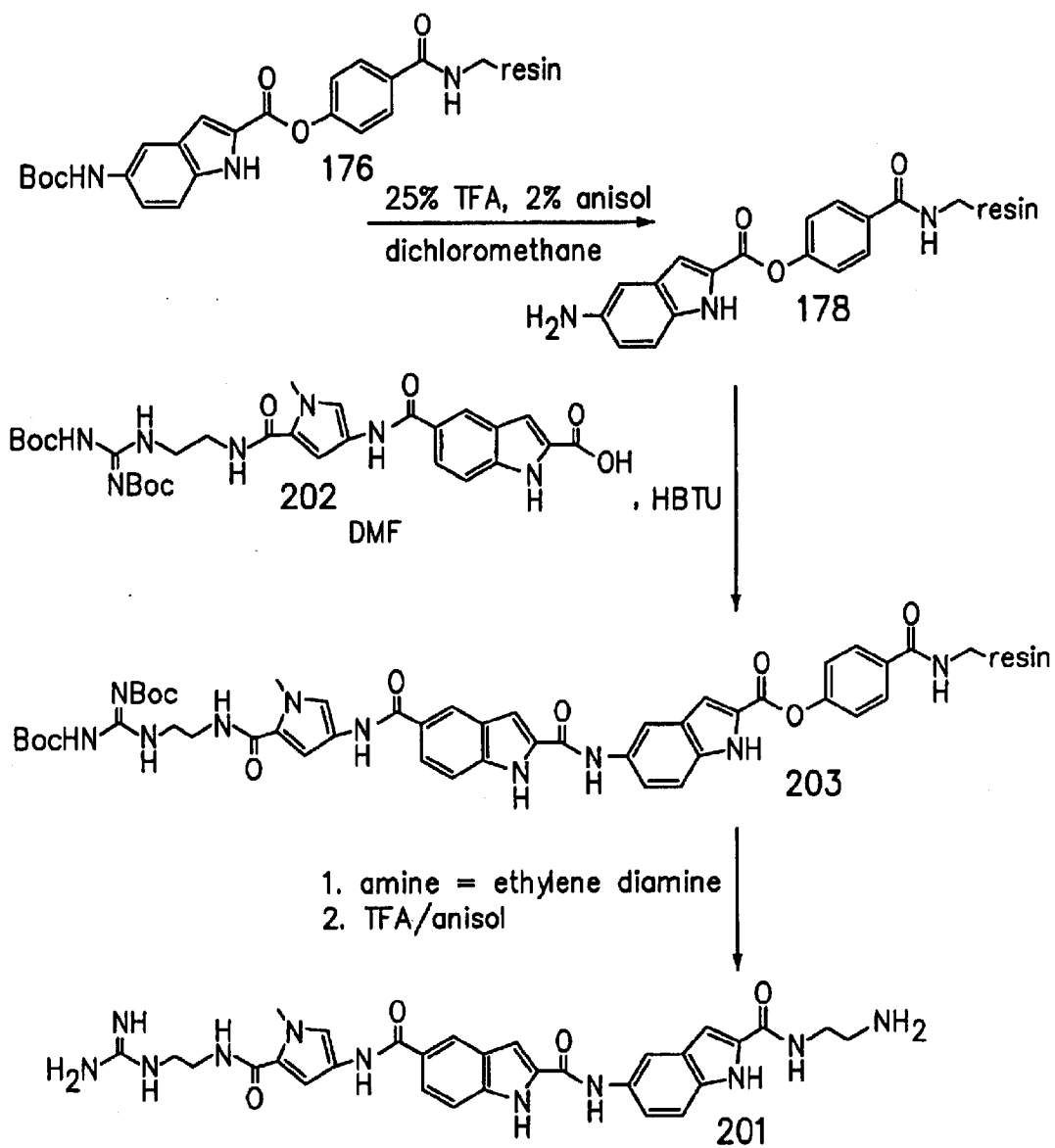
Figure 17:
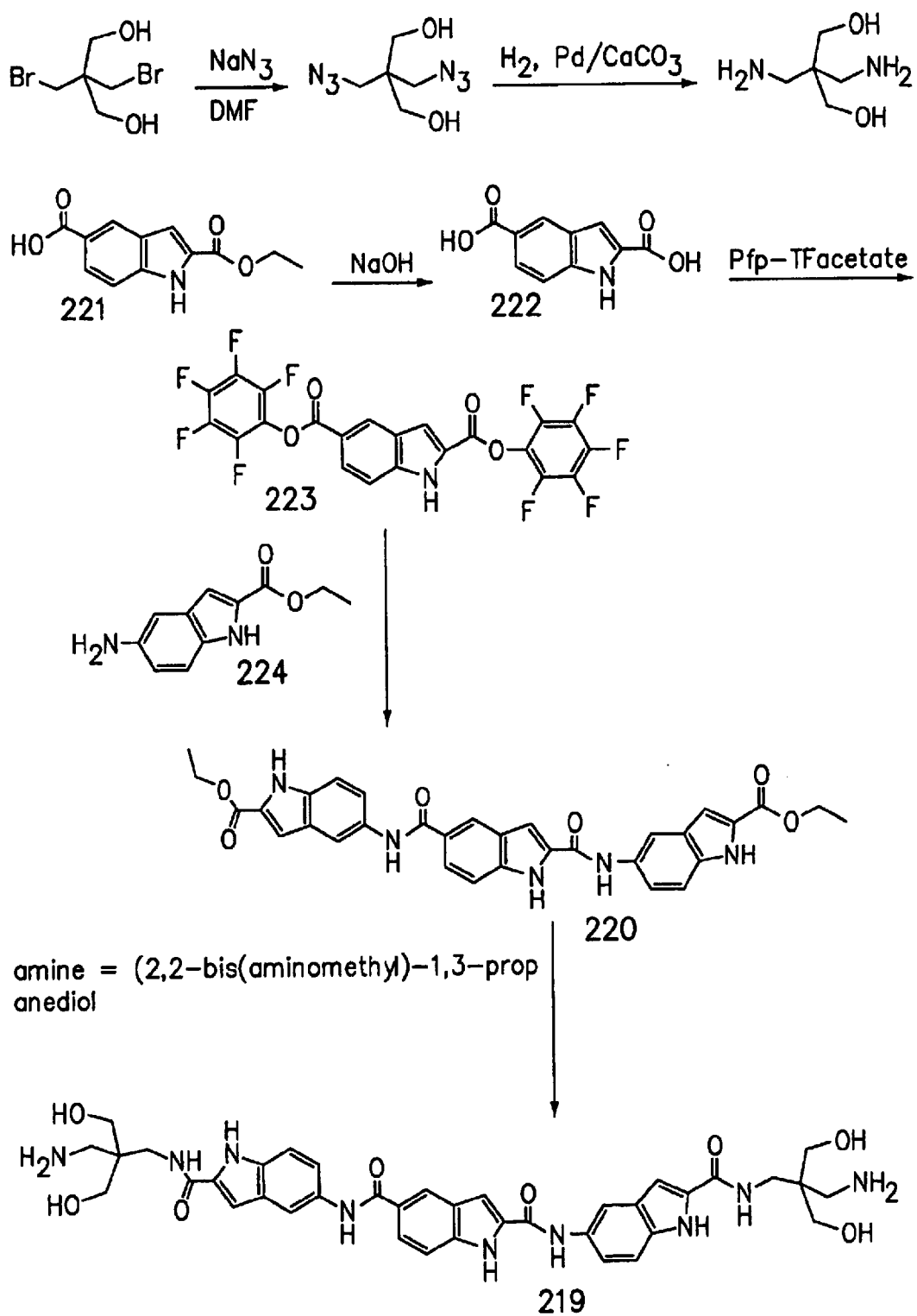
FIGS. 17–19 are referred to as Schemes 11–13 resepectively, throughout the specification and each illustrate synthetic routes to various compounds of Formula (I).
Figure 18:
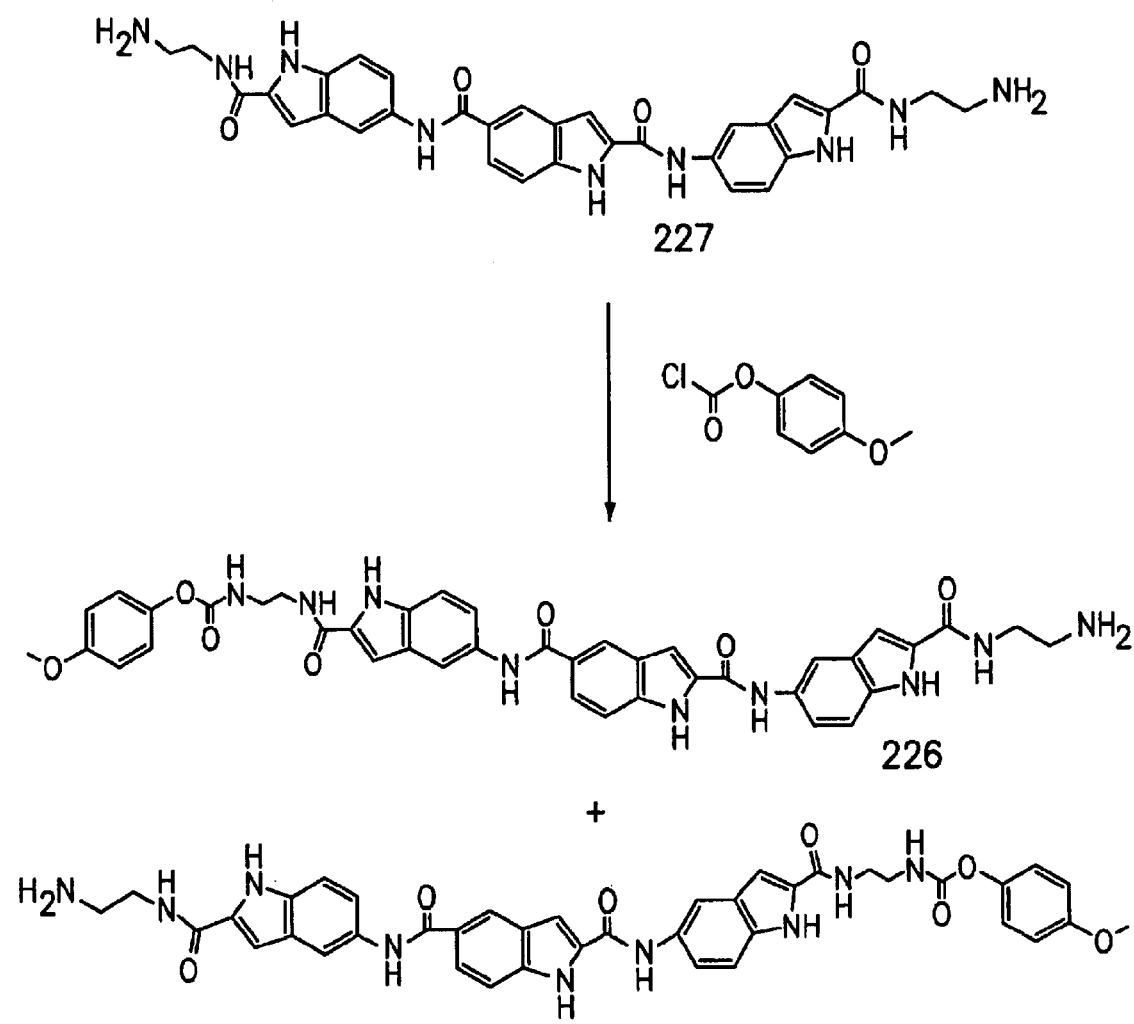
Figure 19:
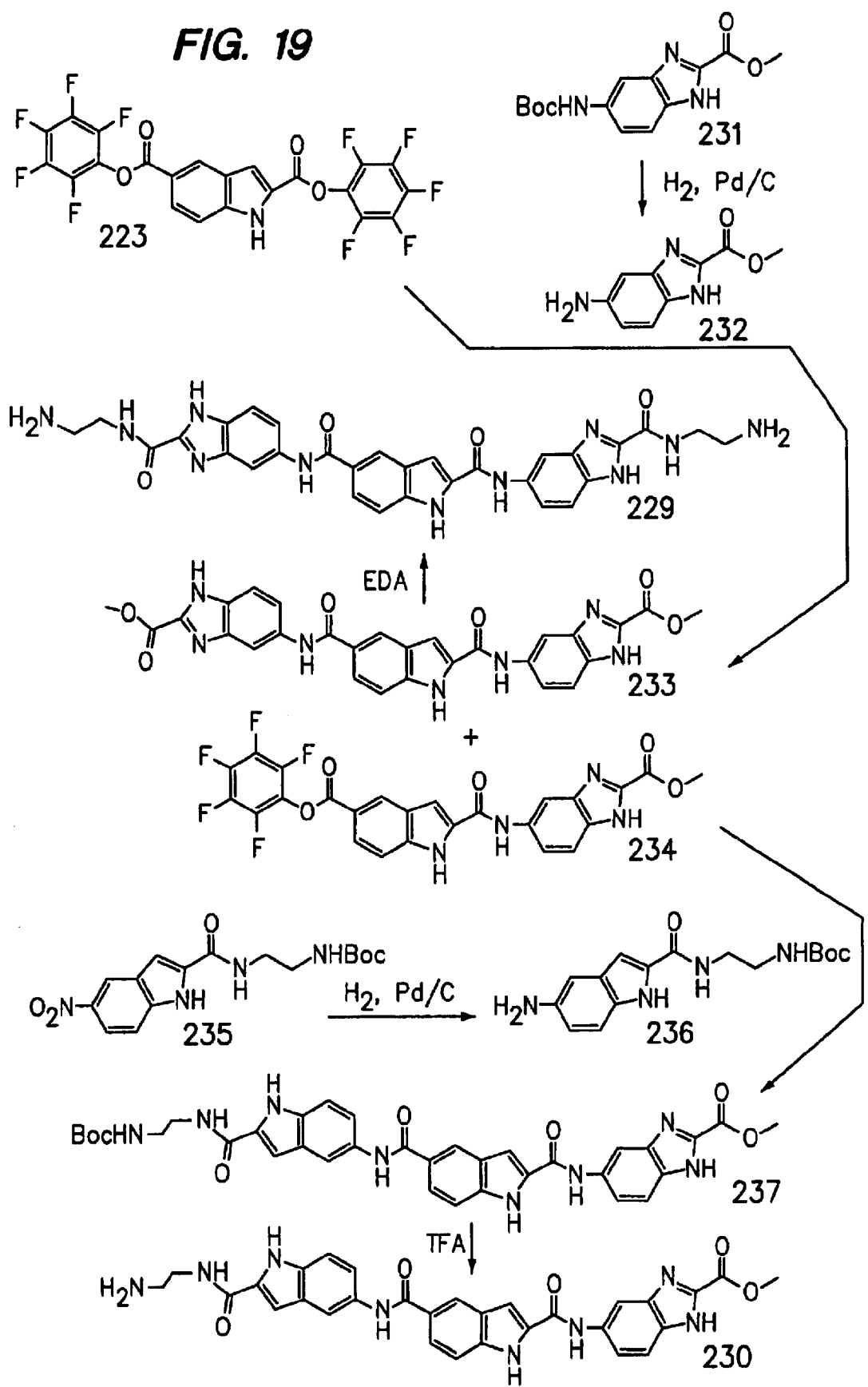

This invention is directed to novel compounds possessing one or more of the following activities: antibacterial, antifungal and antitumor activity. However, prior to describing this invention in further detail, the following terms will first be defined:

Unless otherwise stated, the following terms used in the specification and claims have the meanings given below:

"Alkyl" means a linear or branched saturated monovalent hydrocarbon radical of one to ten carbon atoms, preferably one to six carbon atoms, e.g., methyl, ethyl, propyl, 2-propyl, n-butyl, iso-butyl, tert-butyl, pentyl, and the like.

"Substituted alkyl" means a linear or branched saturated monovalent hydrocarbon radical of one to ten carbon atoms, preferably one to six carbon atoms, which is substituted with 1 to 5 group(s), preferably 1 or 2 group(s), selected from the group consisting of hydroxy, alkoxy, acyl, acylamino, halo, thio, thioalkyoxy, amido, amino, mono or disubstituted amino, carboxy, amidino, guanidino, amidoxime, sulfonylamino, cycloalkyl, heterocyclic, aryl, substituted aryl, heteroaryl, substituted heteroaryl and —NRSO$_2$NR'R" (where R is hydrogen or alkyl and R' and R" are independently hydrogen, alkyl, haloalkyl, aryl, substituted aryl, heteroaryl, and substituted heteroaryl). Representative examples include, but are not limited to, 2-hydroxyethyl, 3-hydroxypropyl, 2-hydroxy-1-hydroxymethylethyl, 2-hydroxy-2-hydroxymethylethyl, 1-hydroxymethylethyl, 3-hydroxybutyl, 2,3-dihydroxypropyl, 2,3-dihydroxypropyl, 2-hydroxy-1-methylpropyl, 2-methoxyethyl, 3-methoxypropyl, 2-acetylethyl, 3-acetylpropyl, 2-acetylaminoethyl, 3-acetylaminopropyl, 2-aminoethyl, 3-aminopropyl, dimethylaminoethyl, dimethylaminopropyl, 2-piperidin-1-ylethyl, 2-piperazin-1-ylethyl, 3-piperazin-1-ylpropyl, 3-piperazin-1-ylpropyl, 3-amidinopropyl, 3-guaindinopropyl, 2-imidazol-2-ylethyl, 3-imidazol-2-ylpropyl, and the like.

"Alkylene" means a linear or branched saturated divalent hydrocarbon radical of one to six carbon atoms, e.g., methylene, ethylene, 2,2-dimethylethylene, propylene, 2-methylpropylene, butylene, pentylene, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Substituted alkenyl" means an alkenyl radical, as defined herein, that is substituted with 1 to 3 group(s), preferably 1 or 2 group(s) selected from the group consisting of hydroxy, alkoxy, acyl, acylamino, halo, amino, mono or disubstituted amino, carboxy, amidino, guanidino, sulfonylamino, heterocyclic, aryl, substituted aryl, heteroaryl, substituted heteroaryl and —NRSO$_2$NR'R" (where R is hydrogen or alkyl and R' and R" are independently hydrogen, alkyl, haloalkyl, aryl, substituted aryl, heteroaryl, and substituted heteroaryl).

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Cycloalkyl" means a saturated monovalent cyclic hydrocarbon radical of three to six ring carbons, e.g., cyclopropyl, cyclopentyl, cyclohexyl, and the like.

"Substituted cycloalkyl" means a cycloalkyl radical as defined herein that is substituted independently with one, two or three substituents, preferably one or two substituents, selected from alkyl, alkoxy, substituted alkyl, acyl, acylamino, sulfonylamino, halo, nitro, cyano, amino, monosubstituted or disubstituted amino and —NRSO$_2$NR'R" (where R is hydrogen or alkyl and R' and R" are independently hydrogen, alkyl, haloalkyl, aryl, substituted aryl, heteroaryl, and substituted heteroaryl).

"Sulfonylamino" means a radical —NRSO$_2$R' where R is hydrogen or alkyl and R' is alkyl, substituted alkyl, amino, monosubstituted amino, disubstituted amino, aryl, substituted aryl, aralkyl, substituted aralkyl, heteroaryl, substituted heteroaryl, heteroaralkyl, and substituted heteroaralkyl, e.g., methylsulfonylamino, benzylsulfonylamino, N-methylaminosulfonylamino, and the like.

"Alkoxy" means a radical —OR where R is an alkyl as defined above e.g., methoxy, ethoxy, propoxy, butoxy and the like.

"Acyl" means a radical —C(O)R, where R is hydrogen, alkyl, substituted alkyl, aryl, substituted aryl, aralkyl, substituted aralkyl, heteroaryl, substituted heteroaryl, heteroaralkyl, substituted heteroaralkyl, heterocyclic, and heterocyclicalkyl group as defined herein. Representative examples include, but are not limited to formyl, acetyl, benzoyl, benzylcarbonyl, glycyl and the like.

"Acylamino" means a radical —NR'C(O)R, where R' is hydrogen or alkyl, and R is hydrogen, alkyl, substituted alkyl, aryl, substituted aryl, aralkyl, substituted aralkyl, heteroaryl, substituted heteroaryl, heteroaralkyl, substituted heteroaralkyl, heterocyclic, and heterocyclicalkyl group as defined herein. Representative examples include, but are not limited to formylamino, acetylamino, benzoylamino, benzylcarbonylamino, and the like. Preferred acylamino groups include the following: —NHC(O)CH(NH$_2$)CH$_3$; —NHC(O)CH(NH$_2$)—(CH$_2$)$_3$—NH—C(NH)NH$_2$; —NHC(O)CH(NH$_2$)—CH$_2$—C(O)NH$_2$; —NHC(O)CH(NH$_2$)—CH$_2$—CO$_2$H; —NHC(O)CH(NH$_2$)—CH$_2$—SH; —NHC(O)CH(NH$_2$)—(CH$_2$)$_2$—C(O)NH$_2$; —NHC(O)CH(NH$_2$)—(CH$_2$)$_2$—CO$_2$H; —NHC(O)CH$_2$—NH$_2$; —NHC(O)CH(NH$_2$)—CH$_2$—(C$_3$H$_2$N$_2$); —NHC(O)CH(NH$_2$)—CH(CH$_3$)CH$_2$CH$_3$; —NHC(O)CH(NH$_2$)—CH$_2$CH(CH$_3$)$_2$; —NHC(O)CH(NH$_2$)—(CH$_2$)$_4$—NH$_2$; —NHC(O)CH(NH$_2$)—(CH$_2$)$_2$—SCH$_3$; —NHC(O)CH(NH$_2$)—CH$_2$Ph; —NHC(O)CH(NH$_2$)—(C$_4$H$_8$N); —NHC(O)CH(NH$_2$)—CH$_2$OH; —NHC(O)CH(NH$_2$)—CH(OH)CH$_3$; —NHC(O)CH(NH$_2$)—CH$_2$—(C$_8$H$_6$N); —NHC(O)CH(NH$_2$)—CH$_2$—Ph-p-OH; and, —NHC(O)CH(NH$_2$)—CH(CH$_3$)$_2$.

"Monosubstituted amino" means a radical —NHR where R represents an alkyl, acyl, aryl, substituted aryl, aralkyl, substituted aralkyl, heteroaryl, substituted heteroaryl, heteroaralkyl, substituted heteroaralkyl, heterocyclic, and heterocyclicalkyl group as defined herein. Representative examples include, but are not limited to methylamino, ethylamino, phenylamino, benzylamino, and the like.

"Disubstituted amino" means a radical —NRR' where R and R' are independently selected from the group consisting of alkyl, acyl, aryl, substituted aryl, aralkyl, substituted aralkyl, heteroaryl, substituted heteroaryl, heteroaralkyl, substituted heteroaralkyl, heterocyclic, and heterocyclicalkyl group as defined herein. Representative examples include, but are not limited to dimethylamino, diethylamino, ethylmethylamino, diphenylamino, dibenzylamino, and the like.

"Halo" means fluoro, chloro, bromo, or iodo, preferably fluoro and chloro.

"Haloalkyl" means alkyl substituted with one or more same or different halo atoms, e.g., —$CH_2Cl$, —$CF_3$, —$CH_2CF_3$, —$CH_2CCl_3$, and the like.

"Aryl" means a monovalent monocyclic, bicyclic or tricyclic aromatic hydrocarbon radical of 6 to 14 ring atoms e.g., phenyl, naphthyl, or anthryl.

"Substituted aryl" means an aryl ring as defined above which is substituted independently with one, two or three substituents, preferably one or two substituents, selected from alkyl, alkoxy, aryloxy, substituted alkyl, acyl, acylamino, sulfonylamino, halo, nitro, cyano, amino, mono-substituted or disubstituted amino and —$NRSO_2NR'R''$ (where R is hydrogen or alkyl and R' and R'' are independently hydrogen, alkyl, haloalkyl, aryl, substituted aryl, heteroaryl, and substituted heteroaryl).

"Heteroaryl" means a monovalent monocyclic, bicyclic or tricyclic radical of 5 to 12 ring atoms having at least one aromatic ring containing one, two, three or four ring heteroatoms selected from N, O, or S, the remaining ring atoms being C, with the understanding that the attachment point of the heteroaryl radical will be on an aromatic ring. More specifically the term heteroaryl includes, but is not limited to, pyridyl, furanyl, thienyl, thiazolyl, tetrazolyl, isothiazolyl, triazolyl, imidazolyl, isoxazolyl, pyrrolyl, pyrazolyl, pyrimidinyl, benzofuranyl, isobenzofuranyl, benzothiazolyl, benzoisothiazolyl, benzotriazolyl, indolyl, isoindolyl, benzoxazolyl, quinolyl, tetrahydroquinolinyl, isoquinolyl, benzimidazolyl, benzisoxazolyl or benzothienyl.

"Substituted heteroaryl" means a heteroaryl ring as defined above which is substituted independently with one, two or three substituents, preferably one or two substituents, selected from alkyl, alkoxy, aryloxy, substituted alkyl, acyl, acylamino, sulfonylamino, halo, nitro, cyano, amino, mono-substituted or disubstituted amino and —$NRSO_2NR'R''$ (where R is hydrogen or alkyl and R' and R'' are independently hydrogen, alkyl, haloalkyl, aryl, substituted aryl, heteroaryl, and substituted heteroaryl).

"Aralkyl", "heteroaralkyl", "substituted aralkyl", "substituted heteroaralkyl", means a radical —$R^aR^b$ where $R^a$ is an alkylene group and $R^b$ is a aryl or substituted aryl, heteroaryl or substituted heteroaryl group as defined herein, e.g., benzyl, pyridin-3-ylmethyl, imidazolylethyl, pyridinylethyl, 3-(benzofuran-2-yl)propyl, and the like.

"Heterocyclic" means a saturated non-aromatic cyclic radical of 5 to 8 ring atoms in which one or two ring atoms are heteroatoms selected from NR (where R is independently hydrogen, alkyl, or heteroalkyl), O, or $S(O)_n$ (where n is an integer from 0 to 2), the remaining ring atoms being C, where one or two C atoms may optionally be replaced by a carbonyl group. The heterocyclic ring may be optionally substituted independently with one, two, or three substituents selected from alkyl, alkoxy, substituted alkyl, acyl, acylamino, sulfonylamino, halo, nitro, cyano, amino, mono-substituted or disubstituted amino and —$NRSO_2NR'R''$ (where R is hydrogen or alkyl and R' and R'' are independently hydrogen, alkyl, haloalkyl, aryl, substituted aryl, heteroaryl, and substituted heteroaryl). More specifically the term heterocyclic includes, but is not limited to, tetrahydropyranyl, 2,2-dimethyl-1,3-dioxolane, piperidino, N-methylpiperidin-3-yl, piperazino, N-methylpyrrolidin-3-yl, 3-pyrrolidino, morpholino, thiomorpholino, thiomorpholino-1-oxide, thiomorpholino-1,1-dioxide, pyrrolinyl, imidazolinyl, and the derivatives thereof.

"Heterocyclicalkyl" means a radical —$R^aR^b$ where $R^a$ is an alkylene group and $R^b$ is a heterocyclic group as defined herein, e.g., tetrahydropyran-2-ylmethyl, 4-methylpiperazin-1-ylethyl, 3-piperidinylmethyl, 2,2-dimethyl-1,3-dioxoxolan-4-ylmethyl, benzyl, and the like.

"Optional" or "optionally" means that the subsequently described event or circumstance may but need not occur, and that the description includes instances where the event or circumstance occurs and instances in which it does not. For example, "heterocyclic group optionally mono- or di-substituted with an alkyl group" means that the alkyl may but need not be present, and the description includes situations where the heterocyclic group is mono- or disubstituted with an alkyl group and situations where the heterocyclic group is not substituted with the alkyl group.

"Hydroxy or amino protecting group" refers to those organic groups intended to protect oxygen and nitrogen atoms against undesirable reactions during synthetic procedures. Suitable oxygen and nitrogen protecting groups are well known in the art e.g., trimethylsilyl, dimethyl-tert-butylsilyl, benzyl, benzyloxy-carbonyl (CBZ), tert-butoxycarbonyl (Boc), trifluoroacetyl, 2-trimethylsilylethanesulfonyl (SES), and the like. Others can be found in the book by T. W. Greene and G. M. Wuts, *Protecting Groups in Organic Synthesis*, Third Edition, Wiley, New York, 1999, and references cited therein.

Amino acid refers to any of the naturally occurring amino acids, as well as synthetic analogs (e.g., D-stereoisomers of the naturally occurring amino acids, such as D-threonine) and derivatives thereof. α-Amino acids comprise a carbon atom to which is bonded an amino group, a carboxyl group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine). Unnatural amino acids are also known in the art, as set forth in, for example, Williams (ed.), Synthesis of Optically Active.alpha.-Amino Acids, Pergamon Press (1989); Evans et al., J. Amer. Chem. Soc., 112:4011–4030 (1990); Pu et al., J. Amer. Chem. Soc., 56:1280–1283 (1991); Williams et al., J. Amer. Chem. Soc., 113:9276–9286 (1991); and all references cited therein. The present invention includes the side chains of unnatural amino acids as well.

Compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual I- or (S)-stereoisomers or as mixtures thereof. For example, if the $R^1$ substituent in a compound of formula (I) is 2-hydroxyethyl, then the carbon to which the hydroxy group is attached is an asymmetric center and therefore the compound of Formula (I) can exist as an I- or (S)-stereoisomer. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic —Chemistry", $4^{th}$ edition J. March, John Wiley and Sons, New York, 1992).

A "pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable acid addition salts" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Groups which form pharmaceutically acceptable acid addition salts include amines, hydrazines, amidines, guanidines, substituted aryl/heteroaryl and substituted alkyl groups that carry at least a nitrogen bearing substitutent such as amino, uanidine, amidino, uanidine and the like.

Amine groups are represented by the formula —NR'R" where R' and R" are independently hydrogen, alkyl, substituted alkyl, alkenyl, substituted alkenyl, aryl, substituted aryl, cycloalkyl, substituted cycloalkyl, heterocyclic, heteroaryl, substituted heteroaryl, and where R' and R", together with the nitrogen to which they are attached, form a heterocyclic or heteroaryl group.

Hydrazines are represented by the formula —NHNR'R" where R' and R" are independently hydrogen, alkyl, substituted alkyl, alkenyl, substituted alkenyl, aryl, substituted aryl, cycloalkyl, substituted cycloalkyl, heterocyclic, heteroaryl, substituted heteroaryl, and where R' and R", together with the nitrogen to which they are attached, form a heterocyclic or heteroaryl group.

Amidino groups are represented by the formula —C(=NH)NR'R" where R' and R" are independently hydrogen, alkyl, substituted alkyl, alkenyl, substituted alkenyl, aryl, substituted aryl, cycloalkyl, substituted cycloalkyl, heterocyclic, heteroaryl, substituted heteroaryl, and where R' and R", together with the nitrogen to which they are attached, form a heterocyclic or heteroaryl group.

Guanidino groups is represented by the formula —NHC(=NH)NR'R" where R' and R" are independently hydrogen, alkyl, substituted alkyl, alkenyl, substituted alkenyl, aryl, substituted aryl, cycloalkyl, substituted cycloalkyl, heterocyclic, heteroaryl, substituted heteroaryl, and where R' and R", together with the nitrogen to which they are attached, form a heterocyclic or heteroaryl group.

A compound of Formula (I) may act as a pro-drug. Prodrug means any compound which releases an active parent drug according to Formula (I) in vivo when such prodrug is administered to a mammalian subject. Prodrugs of a compound of Formula (I) are prepared by modifying functional groups present in the compound of Formula (I) in such a way that the modifications may be cleaved in vivo to release the parent compound. Prodrugs include compounds of Formula (I) wherein a hydroxy, amino, or sulfhydryl group in compound (I) is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), carbamates (e.g., N,N-dimethylamino-carbonyl) of hydroxy functional groups in compounds of Formula (I), and the like.

"Treating" or "treatment" of a disease includes:

(3) preventing the disease, i.e. causing the clinical symptoms of the disease not to develop in a mammal that may be exposed to or predisposed to the disease but does not yet experience or display symptoms of the disease, (3) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Anti-fungal" or "anti-bacterial" means that growth of the fungus or bacterial is inhibited or stopped.

"Anti-tumor" means the compound has the property of inhibiting the growth of tumor cells. Preferably, when the compound is contacted with a tumor cell line at a concentration of 100 μm, growth of the tumor cells is 32% or less as that of a no growth control.

"Bacteriostatic" means the compound has the property of inhibiting bacterial or fungal multiplication, wherein multiplication resumes upon removal of the active compound. For a bacteriostatic compound, its minimum bacteriocidal concentration (MBC) is greater than 4× its minimum inhibitory concentration (MIC).

"Bacteriocidal" or "fungicidal" means that the compound has the property of killing bacteria or fungi. Bacteriocidal/fungicidal action differs from bacteriostasis or fungistasis only in being irreversible. For example, the "killed" organism can no longer reproduce, even after being removed form contact with the active compound. In some cases, the active compound causes lysis of the bacterial or fungal cell; in other cases the bacterial or fungal cell remains intact and may continue to be metabolically active. A bacteriocidal compound exhibits a MBC that is less than 4× its MIC. Similarly, a fungicidal compound exhibits a minimum fungicidal concentration (MFC) that is less than 4× its MIC.

"Minimum inhibitory concentration" or "MIC" refers to the minimum concentration of a compound necessary to completely inhibit growth of the organism tested. Compounds of this invention having an MIC of at least 1 mM are active in the assays described in the examples below. In a preferred compounds have an MIC of 500 μM, and even more preferably an MIC of 100 μM.

"dsDNA" means double stranded DNA.

PREFERRED EMBODIMENTS

While the broadest definition of this invention is set forth in the Summary of the Invention, certain compounds of Formula (I) are preferred.

(A) A preferred group of compounds is that wherein $Z^1$ and $Z^2$ are —NH—.

(B) Another preferred group of compounds is that wherein $X^2$ is aryl, substituted aryl, heteroaryl or substituted heteroaryl.

(C) Another preferred group of compounds is that wherein $X^1$ and $X^3$ are independently heteroaryl or substituted heteroaryl.

(D) Another preferred group of compounds is that wherein $R^1$ and $R^2$ are independently substituted alkyl groups.

(E) Another preferred group of compounds is that wherein $X^2$ is an aryl, substituted aryl, heteroaryl or substituted heteroaryl moiety selected from a group consisting of the following moieties:

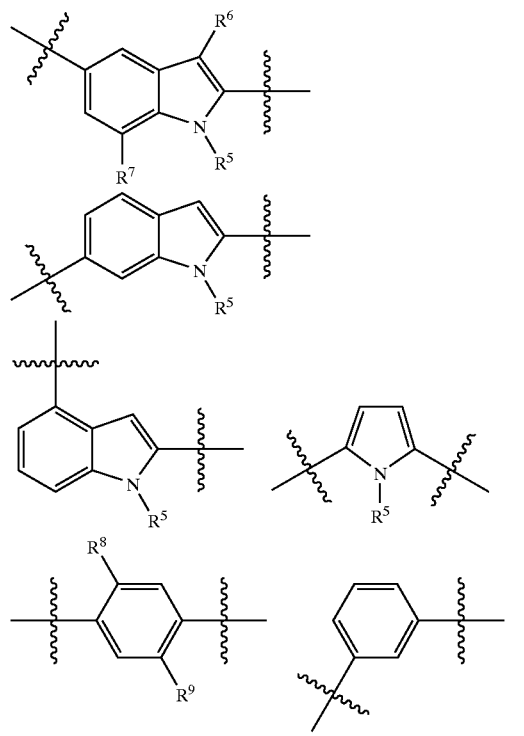

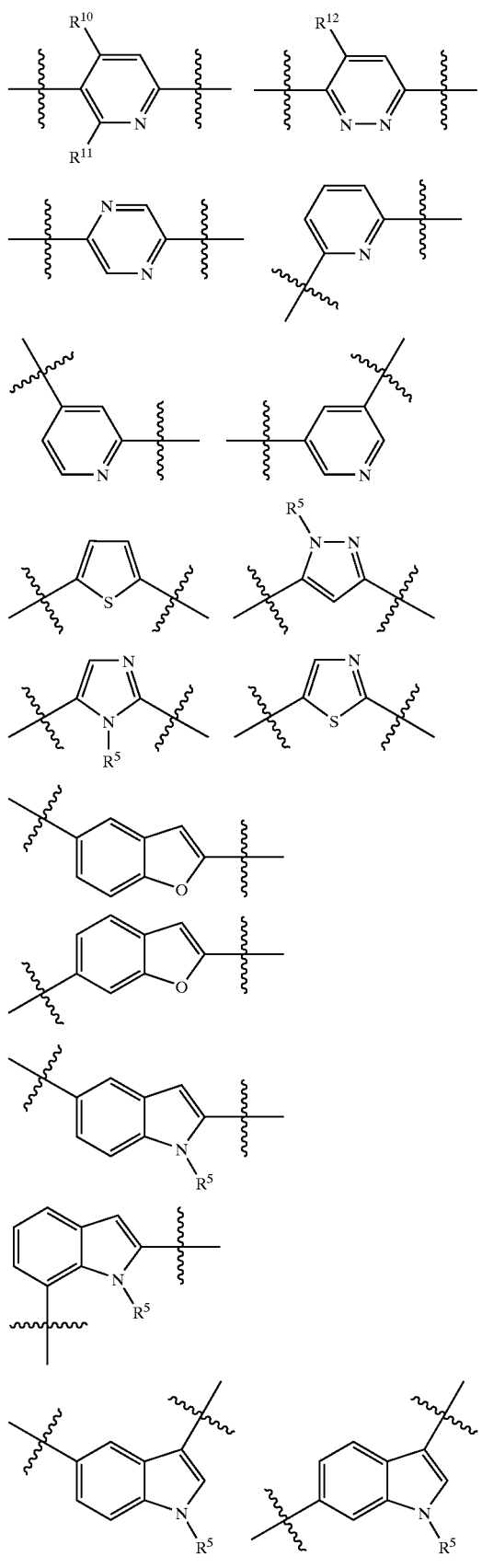

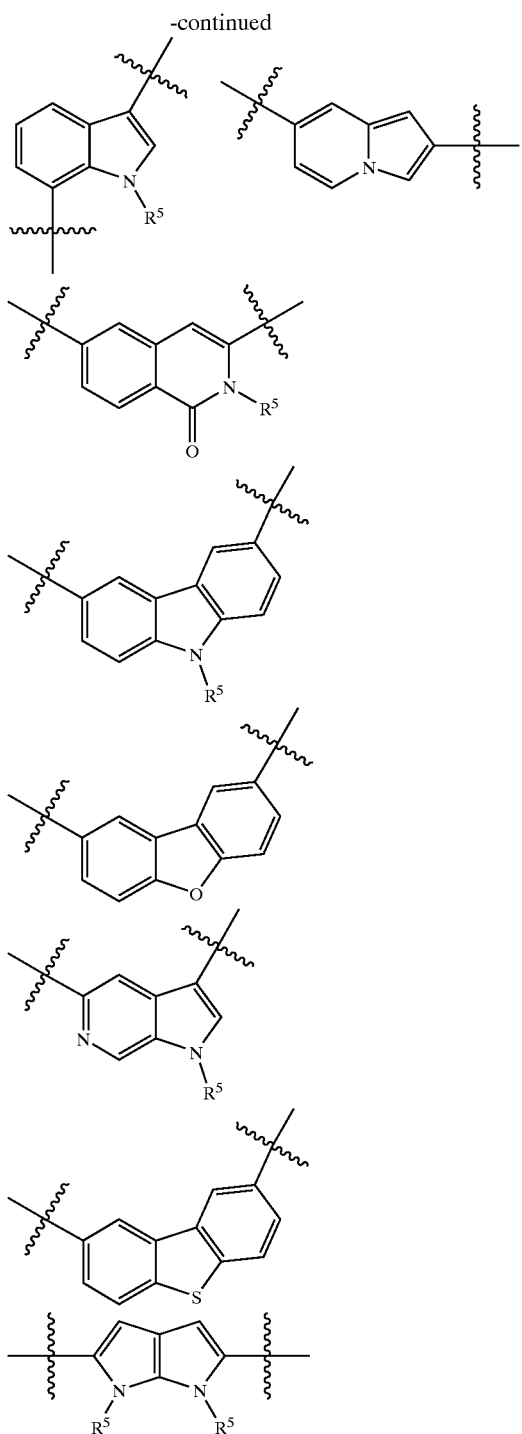

wherein,
R[5] is hydrogen, alkyl or substituted alkyl;
R[6] is hydrogen, alkyl, halo or alkoxy;
R[7] is hydrogen, alkyl or halo;
R[8] is hydrogen, alkyl, substituted alkyl, alkoxy or halo;
R[9] is hydrogen, alkyl, substituted alkyl, alkoxy, nitro or halo;
R[10] is hydrogen or alkyl;
R[11] is hydrogen or alkyl; and,
R[12] is hydrogen or alkyl.

(F) Another preferred group of compounds is that wherein X[1] and X[3] are heteroaryl or substituted heteroaryl moieties independently selected from a group consisting of the following moieties:

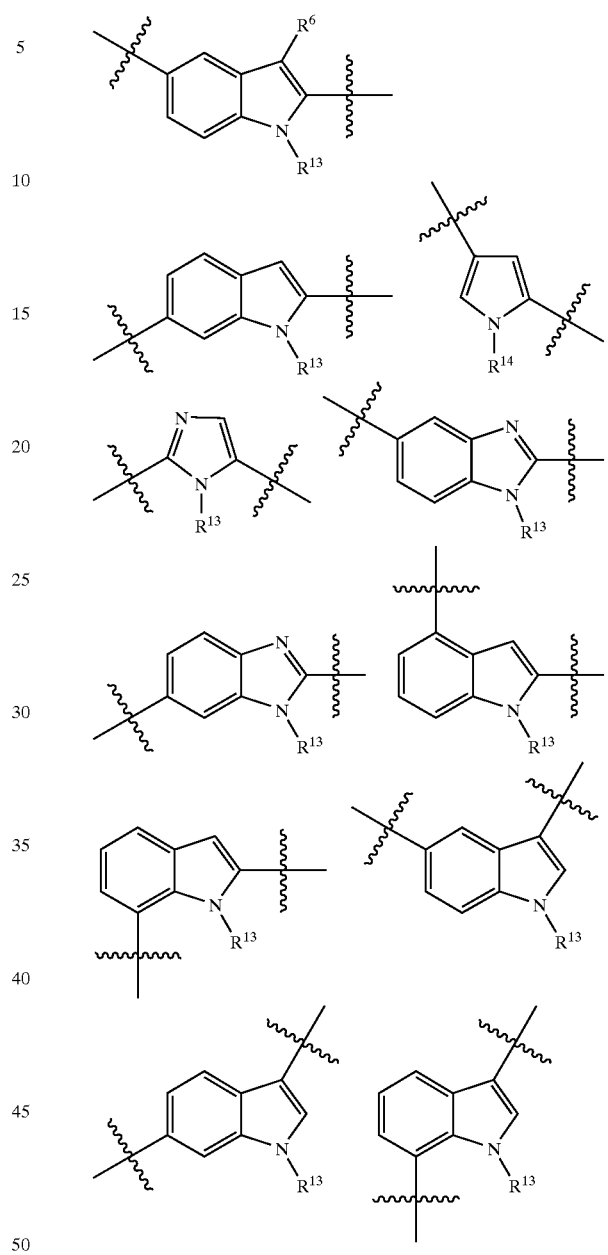

wherein
R[6] is hydrogen, alkyl, halo or alkoxy;
R[13] is hydrogen or alkyl; and,
R[14] is hydrogen, alkyl, substituted alkyl or aralkyl.

(G) Another preferred group of compounds is that wherein R[1] and R[2] are dependently selected from the group consisting of the following moieties:

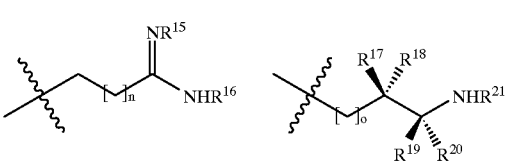

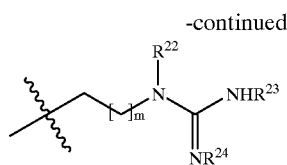

wherein

R¹⁵ is hydrogen, hydroxyl, alkoxyl, alkyl, cycloalkyl or R¹⁵ and R¹⁶ together with the atoms to which they are attached form a heterocyclic ring;

R¹⁶ is hydrogen, alkyl, hydroxyl or cycloalkyl;

R¹⁷, R¹⁸, R¹⁹ and R²⁰ are independently hydrogen or alkyl;

R²¹ is hydrogen alkyl, substituted alkyl, cycloalkyl or acyl;

R²² is hydrogen or alkyl, or R²² and R²³ together with the atoms to which they are attached form a heterocyclic ring, or R²² and R²⁴ together with the atoms to which they are attached form a heterocyclic ring.

R²³ is hydrogen, alkyl, hydroxyl, cycloalkyl or R²³ and R²⁴ together with the atoms to which they are attached form a heterocyclic ring;

R²⁴ is hydrogen, hydroxyl or alkyl;

m is 1, 2 or 3;

n is 1, 2 or 3; and, o is 0, 1, 2 or 3.

(H) Another preferred group of compounds is that wherein R¹⁴ is an alkyl, substituted alkyl or aralkyl moiety, and wherein the moiety is selected from a group consisting of the following moieties:

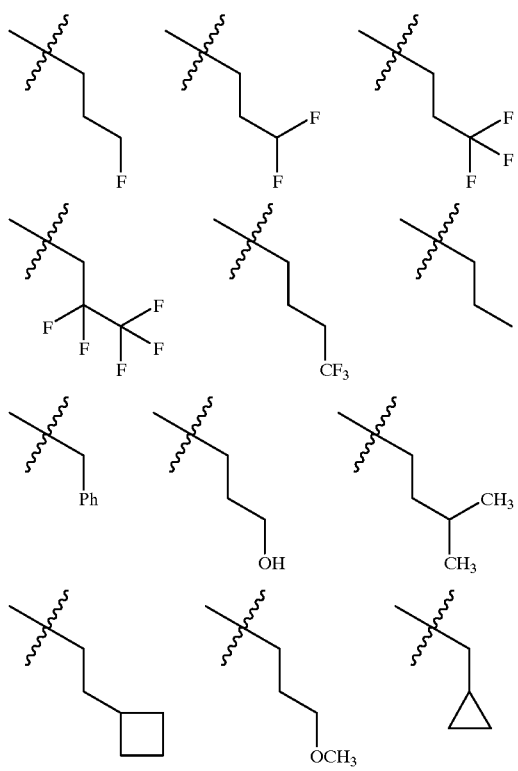

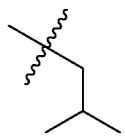

(I) Another preferred group of compounds is that wherein X² is

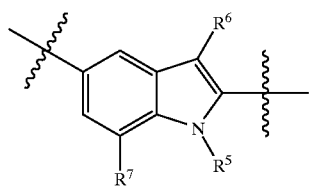

wherein,

R⁵ is hydrogen, alkyl or substituted alkyl;

R⁶ is hydrogen, alkyl, halo or alkoxy; and,

R⁷ is hydrogen, alkyl or halo.

(J) Another preferred group of compounds is that wherein X¹ and X³ are both

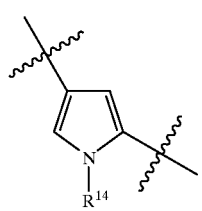

wherein

R¹⁴ is hydrogen, alkyl, substituted alkyl or aralkyl.

(K) Another preferred group of compounds is that wherein R¹ and R² are independently of one of the following structures:

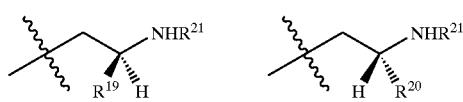

wherein

R¹⁹ and R²⁰ are independently hydrogen or alkyl; and,

R²¹ is hydrogen, alkyl or acyl.

(L) Another preferred group of compounds is that wherein R¹ and R² are of the following structure:

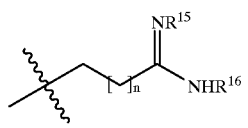

wherein
R$^{15}$ and R$^{16}$ are hydrogen, and,
n is 1 or 2.

(M) Another preferred group of compounds is that wherein R$^1$ and R$^2$ are of the following structure:

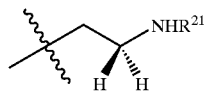

wherein

R$^{21}$ is an alkyl group selected from a group consisting of methyl, ethyl, —CH$_2$CH$_2$OH, —CH$_2$CH$_2$OAc and propyl, or an acyl moiety of the structure —C(O)C($^{25}$)(R$^{26}$)H;

R$^{25}$ is a substituent selected from a group consisting of the following substituents:

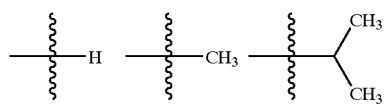

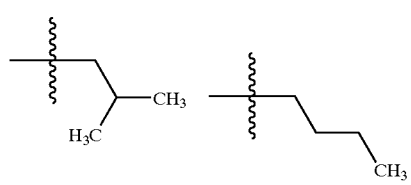

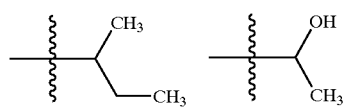

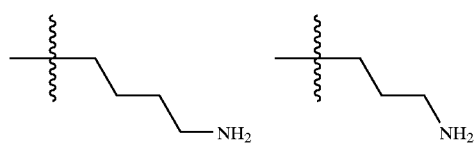

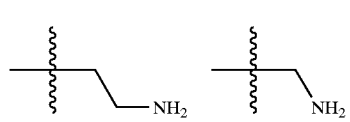

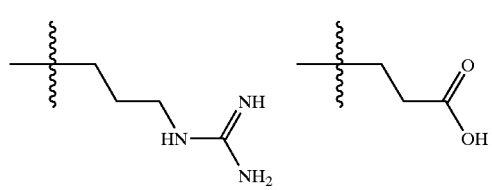

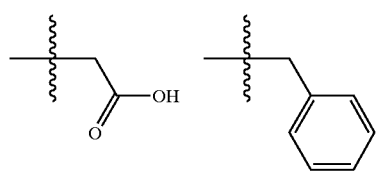

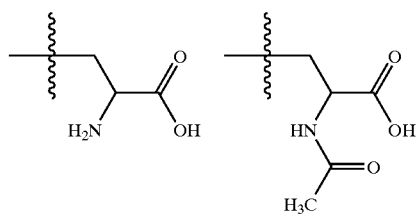

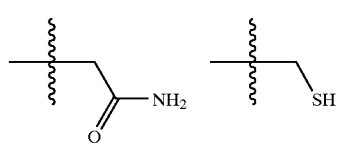

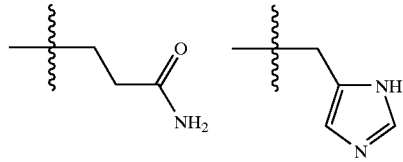

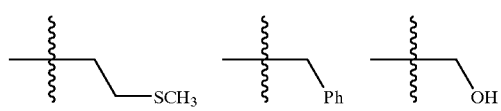

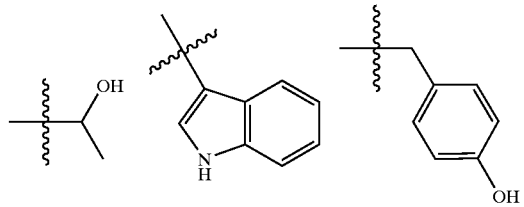

or R$^{25}$ and R$^{26}$ together with the atom to which they are attached form a heterocyclic ring of the following structure:

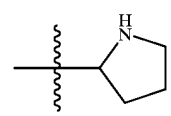

and,

R$^{26}$ is a substituent selected from a group consisting of the following substituents: —H, —NH$_2$ and —NHCH$_3$.

(N) Another preferred group of compounds is that wherein the compound of formula (I) is of the following structure:

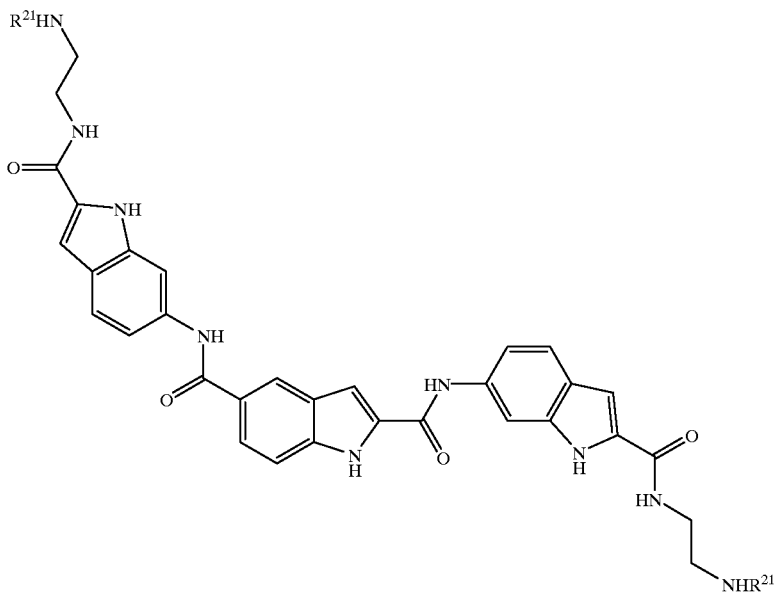

wherein $R^{21}$ is an alkyl group or an acyl group.

(O) Another preferred group of compounds is that wherein the compound of formula (I) is of the following structure:

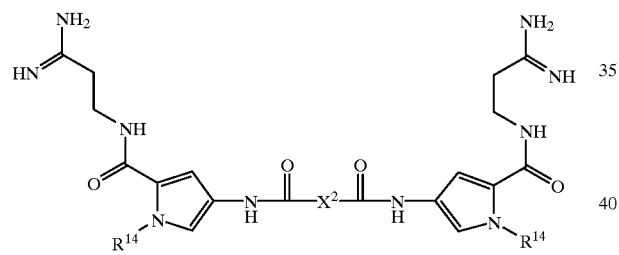

wherein $R^{14}$ is hydrogen, —$CH_2CH_2CH(CH_3)_2$ or —$CH_2(C_3H_5)$; and, $X^2$ is a moiety selected from a group consisting of the following moieties:

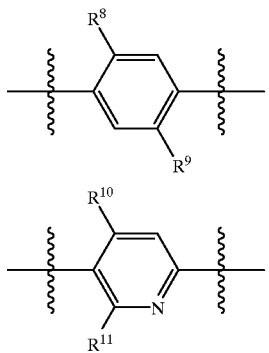

-continued

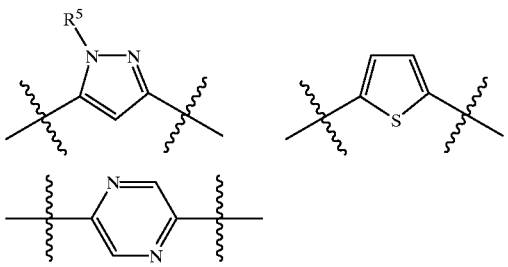

GENERAL SYNTHETIC SCHEME

Compounds of this invention can be made by the methods depicted in the reaction schemes shown below.

The starting materials and reagents used in preparing these compounds are either available from commercial suppliers such as Aldrich Chemical Co., (Milwaukee, Wis., USA), Bachem (Torrance, Calif. USA), Emka-Chemie, or Sigma (St. Louis, Mo., USA) or are prepared by methods known to those skilled in the art following procedures set forth in references such as Fieser and Fieser's Reagents for Organic Synthesis, Volumes 1–15 (John Wiley and Sons, 1991); Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 5th Edition), and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. (make sure lastest volumes included, any better book and suppliers of sm)

The starting materials and the intermediates of the reaction may be isolated and purified if desired using conventional techniques, including but not limited to filtration, distillation, crystallization, chromatography, and the like.

Such materials may be characterized using conventional means, including physical constants and spectral data.

Preparation of compounds of Formula (I)

Schemes A and B describe alternative methods to prepare the compounds of Formula (I).

Compounds of Formula (1) where $Z^1$ and $Z^2$ are —NH—; $R^1$ and $R^2$ and $X^1$ and $X^2$ are as defined in the Summary of the Invention and are the same can be prepared as shown in Scheme A below.

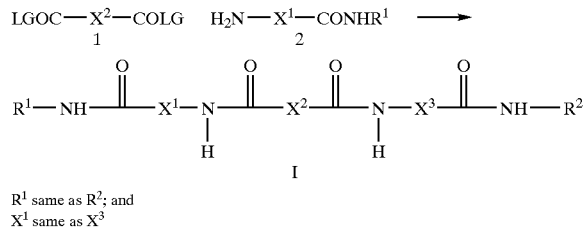

A compound of Formula I wherein $Z^1$ and $Z^2$ are —NH—; $R^1$ and $R^2$ and $X^1$ and $X^2$ are as defined in the Summary of the Invention and are the same can be prepared in one step by reacting a dicarboxylic acid derivative 1 (wherein LG is a suitable leaving group such as halo, pentafluorophenyloxy, and the like) with at least two equivalent of an amine of formula 2. The reaction is typically carried out in a polar organic solvent such as dimethylformamide, tetrahydrofuran, and the like and at an ambient temperature. It will be recognized by a person skilled in the art that if the leaving group is halo, then the reaction will be conducted in the presence of a non-nucleophilic base such as triethylamine and the like.

Compounds of formula 1 and 2 are commercially available from vendors such as Aldrich, Sigma, etc. Alternately these compounds can be prepared by methods well known in the art. For example, compounds of formulae 1 and 2 can be prepared by the procedure illustrated in Scheme 1 and described in detail in Example 1 below.

Additionally, it will be readily apparent to a person skilled in the art that a compound of Formula I where $Z^1$ and $Z^2$ are —O— can be prepared by following the above procedure but substituting the amino group in compound 2 with a hydroxy group.

Alternatively, compounds of Formula (I) where $Z^1$ and $Z^2$ are —NH—; $R^1$ and $R^2$ and $X^1$ and $X^2$ are as defined in the Summary of the Invention and are the same can be prepared as shown in Scheme B below.

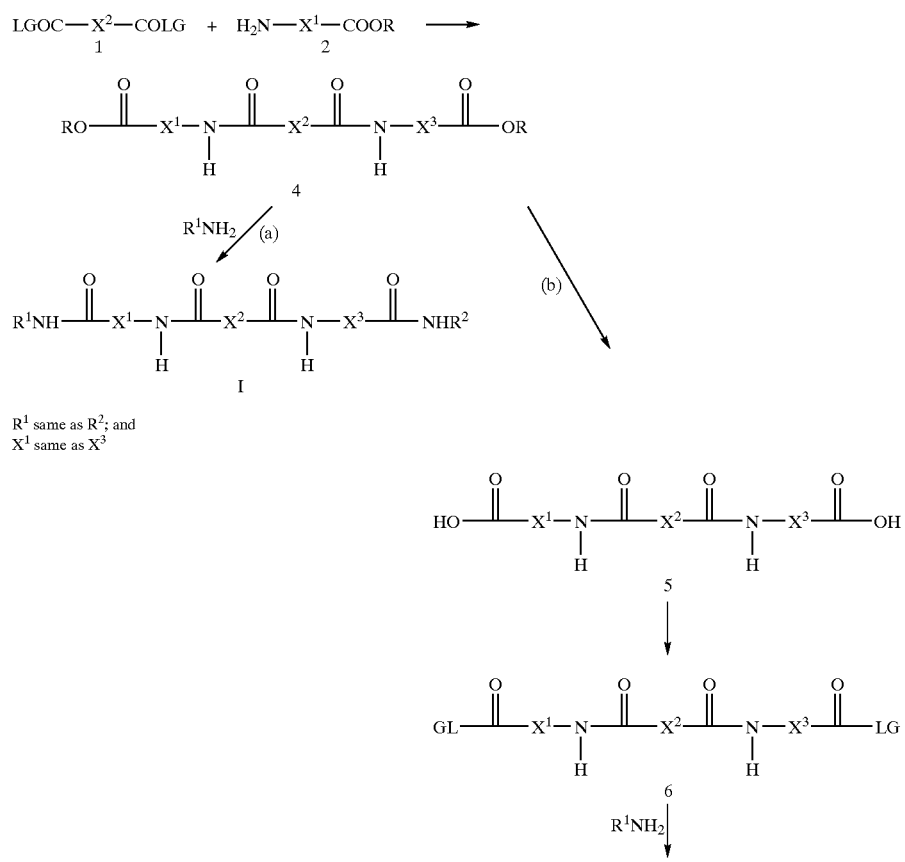

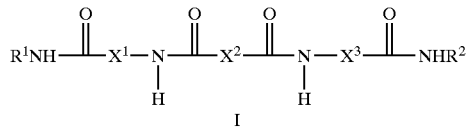

$R^1$ same as $R^2$; and
$X^1$ same as $X^3$

Reaction of a compound of formula 1 with an amino ester of formula 3 under conditions described in Scheme A above provides a diester compound of formula 4. Compound 4 is then converted to a compound of Formula I by following the procedures illustrated in method (a) or (b) above. In method (a), the diester 4 is treated with at least two equivalents of an amine of formula $R^1NH_2$ to provide a compound of Formula (I). The reaction is carried out between 40–60° C. and in a polar organic solvent such as dimethylformamide, tetrahydrofuran and the like.

In method (b), the diester is first hydrolyzed under basic hydrolysis reaction conditions to provide the diacid 5, which is then converted to a compound of Formula (I) under the conditions described above. Syntheses of compounds of Formula (I), following the procedures described in Scheme B, are described in Examples 2–6.

Utility, Testing, and Administration

Utility

The present invention provides novel compounds possessing one or more of the following activities: antibacterial, antifungal and antitumor activity. The compounds and compositions containing them are therefore useful in the treatment of one or more of the following diseases: bacterial infections, fungal infections and cancer. Without wishing to be bound to any theory, Applicants believe that the antibacterial and antifungal activity of the compounds of Formula (I) is due to their binding to the minor groove of the double stranded DNA. Applicants further believe that the antitumor activity of the compounds of Formula (I) is due to their inhibition of topoisomerases.

Topoisomerases are essential enzymes in virtually all living cells. The enzymes have two distinct classes: type I and type II enzymes (J. C. Wang, review). Top I relaxes supercoiled DNA by transiently nicking one DNA strand and rotate one strand about the other. Top II relaxes supercoiled DNA and decatenate linked DNA by transiently cleaving both DNA strands and passing another DNA through the lesion. Since their discovery, topoisomerases have been widely targeted in cancer therapy.

Compounds of Formula (I) are also useful as ultraviolet (UV) light absorbers. Accordingly, they are suitable for use in compositions requiring a UV light absorbing additive, such as plastic compositions. In this regard, it is known that prolonged exposure to UV light can have a deleterious effect on the physical properties and compositional stability of certain plastics. It is therefore conventional to include a UV light absorbing additive in such plastic compositions, and the compounds of Formula (I) can be employed in this manner.

Compounds of the present invention are further useful in that they bind to the minor groove of dsDNA thereby inducing DNA duplex formation. This property is beneficial in biological assays or diagnostic tests that measure the formation or stability of DNA duplexes. For instance, where one is attempting to measure the formation of a DNA duplex with a low $T_m$, one can increase the duplex population by adding a compound of Formula (I). Such an increase in population ensures that the binding event will be more easily measured. A compound of Formula (I) can also be used where one is detecting a single nucleotide polymorphism (SNP) through duplex formation. The compound will preferentially increase the $T_m$ of a perfectly matched duplex over a single mutated duplex, therein allowing one to more easily distinguish the two.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors. The drug can be administered more than once a day, preferably once or twice a day.

Therapeutically effective amounts of compounds of Formula (I) may range from approximately 0.05 to 50 mg per kilogram body weight of the recipient per day; preferably about 0.01–25 mg/kg/day, more preferably from about 0.5 to 10 mg/kg/day. Thus, for administration to a 70 kg person, the dosage range would most preferably be about 35–70 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen which can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of this invention is inhalation. This is an effective method for delivering a therapeutic agent directly to the respiratory tract for the treatment of diseases such as asthma and similar or related respiratory tract disorders (see U.S. Pat. No. 5,607,915).

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist which is carried into the patient's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula (I) in combination with at least one pharmaceutically acceptable excipient. Acceptable excipients are non-toxic, aid administration, and do not adversely affect the therapeutic benefit of the compound of Formula (I). Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01–99.99 wt % of a compound of Formula (I) based on the total formulation, with the balance being one or more suitable pharmaceutical excipients. Preferably, the compound is present at a level of about 1–80 wt %. Representative pharmaceutical formulations containing a compound of Formula (I) are described below.

EXAMPLES

The following preparations and examples are given to enable those skilled in the art to more clearly understand and to practice the present invention. They should not be considered as limiting the scope of the invention, but merely as being illustrative and representative thereof.

The following abbreviations are employed: AcOEt for ethylacetate; DCE for 1,2-dichloroethane; DCM for dichloromethane; DIPEA for diisopropylethylamine; DMF for dimethylformamide; DMSO for dimethylsulfoxide; EtOH for ethanol; MeOH for methanol; THF for tetrahydrofuran; Pyr for pyridine; TFA for trifluoroacetic acid; DCC for N,N'-dicyclohexylcarbodiimide; DCU for N,N'-dicyclohexylurea; Me for a methyl radical; Et for an ethyl radical; Phe for a phenyl radical; Np for a 4-nitrophenyl radical; Pfp for a pentafluorophenyl radical; Gly for a glycine amino acid residue; Lys for a lysine amino acid residue; Arg for a arginine amino acid residue; Py for a 4-amino-1-methyl-1H-pyrrole-2-carboxylic acid residue; Npc(Me) for a 4-nitro-1-methyl-1H-pyrrole-2-carboxylic acid residue; Npc(Et) for a 4-nitro-1-ethyl-1H-pyrrole-2-carboxylic acid residue; Npc(Pr) for a 4-nitro-1-propyl-1H-pyrrole-2-carboxylic acid residue; MMT for a monomethoxytrityl (p-anisyldiphenylmethyl) protecting group; Bzl for a benzyl protecting group; Boc for a tert-butoxycarbonyl protecting group; Fmoc for a fluorenylmethoxycarbonyl protecting group; Z for a benzyloxycarbonyl protecting group; t-Bu for a tert-butyl protecting group; Boc-5-Ain for N-Boc-5-Amino-Indole-2-Carboxylic Acid; Boc-5-Ain-HBA-AMPS for N-Boc-5-Amino-Indole-2-Carboxylic Acid (p-Hydroxy benzamide methyl polystyrene)ester; Boc Py for N-Boc-4-amino-1-methyl pyrrole-2-carboxylic acid; Boc-Py-HBA-AMPS for N-Boc-4-Amino-1-Methyl Pyrrole-2-Carboxylic Acid (p-Hydroxy benzamide methyl polystyrene)ester; BOP for Benzotriazol-1-yloxy-tris (dimethylamino)phosphonium hexafluorophosphate; DE for 2-(Dimethylamino)ethylamine; DIC for N,N' diisopropyl carbodiimide; DIEA for diisopropylethyl amine; DMAP for 4-Dimethylaminopyridine; DMF for dimethyl formamide; DP for 3-(Dimethylamino)propylamine; HBA-AMPS for p-hydroxybenzamide-methylpolystyrene; HBTU for O-Benzotriazol-1yl-N,N,N',N'-tetramethyluronium hexafluorophosphate; HCl for hydrochloric acid; Pzl-Gu-(Boc)$_2$ for N,N'-Bis(tert-butoxycarbonyl)-1H-pyrazole-1-carboxamidine; TFA for Trifluoro acetic acid; NMR for nuclear magnetic resonance spectrum; MS for mass spectrum; TLC for thin layer chromatography on silica gel; HPLC for high pressure liquid chromatography; mp for melting point; mp d for melting point with decomposition. In reporting NMR data, chemical shifts are given in ppm and coupling constants (J) given in Hertz (Hz). All melting points are uncorrected.

Example 1

Following Scheme 1

(A) Synthesis of indole-2,5-dicarboxylic acid, 1

Solution of 1H-Indole-2,5-dicarboxylic acid 2-ethyl ester[#] (20.0 g, 85.75 mmole) and NaOH (100 mmole) in a mixture of water/MeOH (1/1) (200 ml) was stirred at 50° C. for 4 h and then overnight at ambient temperature. The reaction mixture was evaporated in vacuo to dryness and the residue was dissolved in water (200 ml) and acidified with 1M HCl up to pH=3. The precipitates were collected on the filter and washed with water (3×50 ml) and dried over phosphorus pentoxide in dessicator to give indole-2,5-dicarboxylic acid 1 (10.38 g, 59%) of compound 1 as white crystals. MS: 203.7 (M-2H); 204.7 (M–H). [1]-NMR (DMSO-d$_6$): 8.32 (m, 1H, H-4, indole); 7.80 (m, 1H, H-6, indole); 7.45 (d, 1H, H-7, indole); 7.22 (s, 1H, H-3, indole).

(B) 1H-Indole-2,5-dicarboxylic acid dipentafluorophenyl ester, 2

A solution of indole-2,5-dicarboxylic acid 1 (5.15 g, 25.1 mmole), pentafluorophenol (10.00 g, 52.7 mmole) and DCC (10.9 g, 52.7 mmole) in DMF (250 ml) was stirred for 16 h at ambient temperature and evaporated. The residue was coevaporated with toluene (3×100 ml) and recrystallized from the same solvent. Yield: 11.16 g (82.5%). $^1$H-NMR (DMSO-d$_6$): 13.03 (s, 1H, H-1, indole); 8.76 (m, 1H, H-4, indole); 8.08 (m, 1H, H-6, indole); 7.84 (s, 1H, H-3, indole); 7.70 (d, 1H, H-7, indole). $^{19}$F-NMR (DMSO-d$_6$): -153.22&-153.60 (m, 2F&2F, F-2&F-6, -OPfp); -157.15& -157.80 (m, 1F&1F, F-4, -OPfp); -162.03&-162.40 (m, 2F, F-3&F-5, -OPfp).

(C) Npc(Me)-OH, 3

A solution of Npc(Me)-OMe (18.4 g, 100.0 mmole) and NaOH (200 mmole) in a mixture of water/MeOH (2/3) (200 ml) was stirred at 50 C. for 6 h and then overnight at ambient temperature and evaporated. The residue was dissolved in water (200 ml) and acidified with 1N HCl up to pH 2.0. The yellowish precipitate was collected, washed with water (5×250 ml) and dried in vacuo over phosphorus pentoxide to give Npc(Me)-OH, 3 16.16 g (95%) as a yellowish crystalline material. $^1$-NMR (DMSO-d$_6$): 7.61&7.40 (m&m, 1H&1H, H-3&H-5, Py); 3.87 (s, 3H, NCH$_3$, Py).

(D) Npc(Me)—Cl, 4

Stirred suspension of Npc(Me)—OH 3 (13.66 g, 80.0 mmole) in thionyl chloride (50 ml) was gently refluxed 4 h and evaporated. The residue was coevaporated with dry toluene (3×50 ml) and used for the next step without purification.

(E) Npc(Me)—NHCH$_2$CH$_2$CN, 5

To a stirred solution of Npc(Me)—Cl 4 (80.0 mmole) and DIPEA (13.0 g, 17.4 ml, 100 mmole) in dry toluene (300 ml) at 0 C. aminopropionitrile (14.0 g, 200.0 mmole) was added dropwise. The reaction mixture was stirred at 0 C. for 30 min and at ambient temperature for 3 h and evaporated. The residue was suspended in AcOEt (300 ml) and washed with water (2×100 ml), 0.1 M HCl (3×100 ml), brine (2×100 ml), 9.5% NaHCO$_3$ (3×100 ml) and brine (2×100 ml). The organic layer was dried over sodium sulfate and evaporated to give 17.70 g (99%) of Npc(Me)—NHCH$_2$CH$_2$CN 5 as a white crystalline material. MS: 223.11 (M+H). $^1$-NMR (DMSO-d$_6$): 7.59&7.18 (m&m, 1H&1H, H-3&H-5, Py); 6.63 (t, 1H, —NHCH$_2$CH$_2$CN); 3.99 (s, 3H, NCH$_3$, Py); 3.67 (m, 2H, NHCH—CH$_2$CN); 2.74 (t, 2H, NHCH$_2$CH$_2$CN).

(F) Npc(Me)—NHCH$_2$CH$_2$C(=NH)NH$_2$. HCl, 6

A suspension of Npc(Me)—NHCH$_2$CH$_2$CN 5 (9.0 g, 40.5 mmole) in dry EtOH (250 ml) was saturated with HCl (gas) at ambient temperature and kept for 16 h at 0 C. and evaporated. The residue was co-evaporated with dry toluene (3×200 ml) and suspended in dry EtOH (250 ml). The suspension was saturated with ammonia (gas) at 0 C. and kept for 16 h at 0C. and evaporated. The residue was crystallized from water-ethanol to give 8.26 g (74%) of Npc(Me)-NHCH$_2$CH$_2$C(=NH)NH$_2$ 6 as white crystalline material. $^1$-NMR (DMSO-d$_6$): 9.08&8.76 (bs&bs, 4H, NHCH$_2$CH$_2$C(=NH)NH$_2$. HCl); 8.13&7.52 (d&d, 1H&1H, H-3&H-5, Py); 3.99 (s, 3H, NCH$_3$, Py); 3.51 (m, 2H, NHCH$_2$CH$_2$C(=NH)NH$_2$); 2.62 (t, 2H, NHCH$_2$CH$_2$C(=NH)NH$_2$).

(G) 1H-Indole-2,5-dicarboxylic acid bis-{[5-(2-carbamimidoyl-ethylcarbamoyl)-1-methyl-1H-pyrrol-3-yl]-amide 7

To a stirred solution of Npc(Me)—NHCH$_2$CH$_2$C(=NH)NH$_2$ 6 (55.2 mg, 0.20 mmole) in methanol (20 ml) was added 10% Pd/C (Degussa type, Aldrich) (0.1 g). The flask was evacuated and then flushed 3 times with hydrogen and finally filled with hydrogen at 40 to 50 psi. The resultant suspension was stirred vigorously at 23° C. for 1 hour. The suspended material was filtered off through a pad of Celite in a Buchner funnel and then the funnel was rinsed several times with a small portion of MeOH. The combined filtrate and washings was evaporated in vacuo to dryness. The resulted 4-amino-1-methyl-1H-pyrrole-2-carboxylic acid (2-carbamidoyl-ethyl)-amide was used for the next step without purification.

A solution of compound 2 (51.0 mg, 0.095 mmole) and freshly prepared (as described above) 4-amino-1-methyl-1H-pyrrole-2-carboxylic acid (2-carbamidoyl-ethyl)-amide (22.0 mmole) in dry DMF (2.0 ml) was kept at ambient temperature for 72 hours and evaporated. The residue was re-precipitated from MeOH-ether, the precipitate was dried in vacuo and dissolved in water (5.0 ml). The resulted water solution was filtered through 0.45 µm filter and lyophilized to give 53 mg (83%) of 1H-Indole-2,5-dicarboxylic acid bis-{[5-(2-carbamimidoyl-ethylcarbamoyl)-1-methyl-1H-pyrrol-3-yl]-amide 7. MS: 294.60 (doubly charged peak, (M+H)/2). $^1$-NMR (DMSO-d$_6$): 11.97 (s, 1H, H-1, indole); 10.54&10.22 (s&s, 1H&1H, —C(=O)NH); 9.01&8.67 (bs&bs, 4H&4H, NHCH$_2$CH$_2$C(=NH$_2$×HCl); 8.31 (m, 2H with *, H-6, indole); 8.30 (m, *, NHCH$_2$CH$_2$C(=NH)NH$_2$× HCl); 8.25 (t, 1H, NHCH$_2$CH$_2$C(=NH)NH$_2$×HCl); 7.79 (m, 1H, H-6, indole); 7.48 (m, 1H, H-7, indole); 7.45 (s, 1H, H-3, indole); 7.31&7.28&6.97&6.96 (s&s&d&s, 4H, H-3&H-5, Py,&Py2); 3.83&3.81 (s&s, 6H, NCH$_3$, Py,&Py$_2$); 3.50 (m, 4H, NHCH CH$_2$C(=NH)NH$_2$); 2.62 (m, 4H, NHCH$_2$CH$_2$C(=NH)NH$_2$).

Example 2

Synthesis of 1H-indole-2,5-dicarboxylic acid bis-{[5-(2-amino-ethylcarhamoyl)-1-methyl-1H-pyrrol-3-yl]-amide}

(A) 4-({1-[2-(5-methoxycarbonyl-1methyl-1H-pyrrol-3-ylcarbamoyl)-1H-indol-5-yl]-methanoyl}-amino)-1-methyl-1H-pyrrole-2carboxylic acid methyl ester, 8

To a stirred solution of compound methyl 4-nitro-1-methyl-1H-pyrrole-2-carboxylate (967 mg, 5.25 mmole) in a mixture of AcOEt/EtOH (3/2) (50 ml) was added 10% Pd/C (Degussa type, Aldrich) (0.2 g). The flask was evacuated and then flushed 3 times with hydrogen and finally filled with hydrogen at 40 to 50 psi. The resultant suspension was stirred vigorously at 23° C. for 1 hour. The suspended material was filtered off through a pad of Celite in a Buchner funnel and then the funnel was rinsed several times with a small portion of AcOEt and EtOH. The combined filtrate and washings was evaporated in vacuo to dryness. The resulted methyl 4-amino-1-methyl-1H-pyrrole-2-carboxylate was used for the next step without purification.

A solution of compound 7 (1.13, 2.1 mmole) and freshly prepared (as described above) methyl 4-amino-1-methyl-1H-pyrrole-2-carboxylate in dry DMF (10.0 ml) was kept at ambient temperature for 48 hours and evaporated. The residue was re-precipitated from DMF (10 ml)-0.01 M HCl (100 ml). The precipitate was collected on the filter, washed with water (3×5 ml) end ether (2×3 ml) and dried in vacuo over phosphorus pentoxide to give 4-({1-[2-(5-methoxycarbonyl-1methyl-1H-pyrrol-3-ylcarbamoyl)-1H-indol-5-yl]-methanoyl}-amino)-1-methyl-1H-pyrrole-2carboxylic acid methyl ester 8 with quantitative yield. MS: 478.14 (M+H). $^1$-NMR (DMSO-d$_6$): 11.96 (s, 1H, H-1, indole); 10.43&10.23 (s&s, 1H&1H, —C(=O)NH ); 8.29 (m, 1H, H-6, indole); 7.50 (m, 3H, H-7, indole; H-3 or H-5, Py$_1$&Py$_2$); 7.37 (s, 1H, H-3, indole); 6.95 (m, 2H, H-3 or H-5, Py$_1$&Py$_2$); 3.86&3.85 (s, 6H, NCH$_3$, Py$_1$&Py$_2$); 3.74&3.73 (s, 6H, OCH$_3$, Py$_1$&Py$_2$).

(B) 4-({1-[2-(5-hydroxycarbonyl-1-methyl-1H-pyrrol-3-ylcarbamoyl)-1H-indol-5-yl]-methanoyl}-amino)-1-methyl-1H-pyrrole-2-carboxylic acid, 9

A solution of 4-({1-[2-(5-methoxycarbonyl-1methyl-1H-pyrrol-3-ylcarbamoyl)-1H-indol-5-yl]-methanoyl}-amino)-1-methyl-1H-pyrrole-2carboxylic acid methyl ester 8 (1.04 g, 2.18 mmole) and NaOH (10 mmole) in a mixture of water/MeOH (1/4) (25 ml) was stirred at 50C. for 6 h and then overnight at ambient temperature. The reaction mixture was evaporated in vacuo to dryness and the residue was dissolved in water (50 ml) and acidified with 1M HCl up to pH=3. The precipitate was collected on the filter and washed with water (3×50 ml) and dried over phosphorus pentoxide in dessicator to give 0.85 g (87%) of 4-({1-[2-(5-hydroxycarbonyl-1-methyl-1H-pyrrol-3-ylcarbamoyl)-1H-indol-5-yl]-methanoyl}-amino)-1-methyl-1H-pyrrole-2-carboxylic acid 9 as white crystalline material. MS: 448.08 (M–H). $^1$-NMR (DMSO-d$_6$): 11.96 (s, 1H, H-1, indole); 10.45&10.25 (s&s, 1H&1H, —C(=O)NH); 8.30 (m, 1H, H-6, indole); 7.48 (m, 3H with *, H-7, indole); 7.49&7.46 (d&d, *, H-3 or H-5, Py$_1$&Py$_2$); 7.39 (s, 1H, H-3, indole); 6.91 (m, 2H, H-3 or H-5, Py$_1$&Py$_2$); 3.84&3.83 (s&s, 6H, NCH$_3$, Py$_1$&Py$_2$).

(C) 4-({1-[2-(5-pentafluorophenoxycarbonyl-1-methyl-1H-pyrrol-3-ylcarbamoyl)-1H-indol-5-yl]-methanoyl}-amino)-1-methyl-1H-pyrrole-2carboxylic acid pentafluorophenyl ester, 10

A solution of 4-({1-[2-(5-hydroxycarbonyl-1-methyl-1H-pyrrol-3-ylcarbamoyl)-1H-indol-5-yl]-methanoyl}-amino)-1-methyl-1H-pyrrole-2-carboxylic acid 9 (0.85 g, 1.86 mmole), pentafluorophenol (0.72 g, 3.9 mmole) and DCC (0.81 g, 3.9 mmole) in DMF (15 ml) was stirred for 16 h at ambient temperature and evaporated. The residue was coevaporated with toluene (3×100 ml) and chromatographed over a silica gel column (2.5×25 cm) using mixture of toluene/AcOEt (7:3), as eluent to give 1.23 g (84%) of 4-({1-[2-(5-pentafluorophenoxycarbonyl-1-methyl-1H-pyrrol-3-ylcarbamoyl)-1H-indol-5-yl]-methanoyl}-amino)-1-methyl-1H-pyrrole-2carboxylic acid pentafluorophenyl ester 10. $^1$-NMR (DMSO-d$_6$): 12.03 (s, 1H, H-1, indole); 10.60&10.41 (s&s, 1H&1H, —C(=O)NH); 7.81 (m, 3H with *, H-6, indole); 7.80&7.78 (d&d, *, H-3 or H-5, Py$_1$&Py$_2$); 7.52 (m, 1H, H-6, indole); 7.41 (s, 1H, H-3, indole); 7.34 (m, 2H, H-3 or H-5, Py$_1$&Py$_2$); 3.92&3.90 (s&s, 6H, NCH$_3$, Py$_1$&Py$_2$). $^{19}$F-NMR (DMSO-d$_6$): -153.56&-153.60 (m&m, 2F&2F, F-2&F-6, -OPfp); -158.17&-158.27 (m&m, 1F&1F, F-4, -OPfp); -162.69 & -162.73 (m&m, 2F&2F, F-3&F-5, -OPfp).

(D) 1H-Indole-2,5-dicarboxylic acid bis-{[5-(2-amino-ethylcarbamoyl)-1-methyl-1H-pyrrol-3-yl]-amide}11

A solution of of 4-({1-[2-(5-pentafluorophenoxycarbonyl-1-methyl-1H-pyrrol-3-ylcarbamoyl)-1H-indol-5-yl]-methanoyl}-amino)-1-methyl-1H-pyrrole-2carboxylic acid pentafluorophenyl ester 10 (150 mg, 0.192 mmole) and ethylenediamine-1,2 (0.26 ml, 3.94 mmole) in dry DMF (2.0 ml) was kept at ambient temperature for 24 hours and evaporated. The residue was dissolved in 0.1TFA and purified by HPLC (Vydac 12 μm C$_{18}$ 2.2×25 cm column, 0% to 60% acetonitrile gradient over 30 minutes, flow 20 mL/min) to give 1H-indole-2,5-dicarboxylic acid bis-{[5-(2-amino-ethylcarbamoyl)-1-methyl-1H-pyrrol-3-yl]-amide} 11, as a bis-trifluoroacetate salt: 56 mg (38%). ES MS: 534.28 (calcd. for M+H$^+$: 534.28).

Example 3

Synthesis of 1H-Indole-2,5-dicarboxylic acid bis-{[5-(2-dimethylamino-ethylcarbamoyl)-1-methyl-1H-pyrrol-3-yl]-amide}, 12

Compound 12 was synthesized as described for Compound 11 above. Yield: (35%) of compound 12. ES MS: 590.32 (calcd. for M+H$^+$:590.32).

Example 4

Synthesis of 1H-Indole-2,5-dicarboxylic acid bis-{[5-(2-amino-propylcarbamoyl)-1-methyl-1H-pyrrol-3-yl]-amide}, 13

Compound 13 was synthesized as described for Compound 11 above. Yield: (37%) of compound 12. The structure was confirmed by ES MS.

Example 5

Synthesis of 1H-Indole-2,5-dicarboxylic acid bis-{[5-(2-dimethylamino-propylcarbamoyl)-1-methyl-1H-pyrrol-3-yl]-amide), 14

Compound 12 was synthesized as described for Compound 11 above. Yield: (31%) of compound 12. The structure was confirmed by ES MS.

Example 6

Synthesis of 1H-Indole-2,5-dicarboxylic acid bis-{[1-methyl-5-(2-piperazin-1-yl-ethylcarbamoyl)-1H-pyrrol-3-yl]-amide}, 15

Compound 15 was synthesized as described for Compound 10 above. Yield: (15%) of compound 15. The structure was confirmed by ES MS.

Example 7

Synthesis of 1-methyl-indole-2,5-dicarboxylic acid bis-{[5-(2-carbamimidoyl-ethylcarbamoyl)-1-methyl-1H-pyrrol-3-yl]-amide), 20

(A) 1H-Indole-2,5-dicarboxylic acid diethyl ester, 16

A suspension of 1H-Indole-2,5-dicarboxylic acid 2-ethyl ester (20.0 g, 85.75 mmole) in a saturated HCl/EtOH (200 ml) was stirred at 55 C. for 24 h and evaporated in vacuo to dryness. The residue was freeze-dried from dioxane to give 22.18 g (99%) of 1H-indole-2,5-dicarboxylic acid diethyl ester, 16 as white powder. MS: 262.12 (M+H). $^1$-NMR (DMSO-d$_6$): 12.23 (s, 1H, H-1, indole); 8.34 (m, 1H, H-4, indole); 7.83 (m, 1H, H-6, indole); 7.49 (m, 1H, H-7, indole); 7.30 (s, 1H, H-3, indole); 4.31 (m, 4H, —OCH$_2$CH$_3$); 1.32 (m, 4H, —OCH$_2$CH$_3$).

(B) 1-Methyl-indole-2,5-dicarboxylic acid diethyl ester, 17

Sodium hydride (60%-suspension, 144 mg, 3.6 mmole) was added to a stirred solution of 1H-indole-2,5-dicarboxylic acid diethyl ester 16 (784 mg, 3.0 mmole) in dry DMF (15.0 ml) and kept at ambient temperature for 30 min. To a resulted reaction mixture MeI (280 μl, 4.5 mmol) was added and kept at ambient temperature for 16 hours and evaporated. The residue was suspended in AcOEt (100 ml) and washed with water (2×20 ml), 0.01 M HCl (3×20 ml) and brine (2×100 ml). The organic layer was dried over sodium sulfate and evaporated to give 800 mg (97%) of 1-methyl-indole-2,5-dicarboxylic acid diethyl ester 17 as a yellow oil. $^1$-NMR (DMSO-d$_6$): 8.45 (m, 1H, H-4, indole); 8.03 (m, 1H, H-6, indole); 7.40 (m, 1H, H-7, indole); 7.38

(s, 1H, H-3, indole); 4.40 (m, 4H, —OCH$_2$CH$_3$); 4.10 (s, 3H, NCH$_3$, indole); 1.42 (m, 4H, —OCH$_2$CH$_3$).

(C) 1-Methyl-indole-2,5-dicarboxylic acid, 18

Solution of 1-methyl-indole-2,5-dicarboxylic acid diethyl ester 17 (675 mg, 2.5 mmole) and NaOH (5.00 mmole) in a mixture of water/MeOH (1/4) (20 ml) was stirred at 50 C. for 4 h and then overnight at ambient temperature. The reaction mixture was evaporated in vacuo to dryness and the residue was dissolved in water (20 ml) and acidified with 1M HCl up to pH=3. The precipitate was collected on the filter and washed with water (3×5 ml) and dried over phosphorus pentoxide in dessicator to give 488 mg (89%) of 1-methyl-indole-2,5-dicarboxylic acid 18 as white crystalline material. MS: 218.2 (M−H). $^1$—NMR (DMSO-d$_6$): 8.35 (m, 1H, H-4, indole); 7.90 (m, 1H, H-6, indole); 7.41 (d, 1H, H-7, indole); 7.32 (s, 1H, H-3, indole); 4.05 (s, 3H, NCH$_3$, indole).

(D) 1-Methyl-indole-2,5-dicarboxylic acid di(2,3,5,6-tetrafluorophenyl) ester, 19

To a stirred solution of 1-methyl-indole-2,5-dicarboxylic acid 18 (439 mg, 2.0 mmole), triethylamine (12 mmole) in dry DCM (20 ml), maintained at 0C., the solution of tetrafluorophenyl trifluoroacetate (6 mmole) in dry DCM (20 ml) was added dropwise. The stirred reaction mixture was kept on ice bath for 2 h and then overnight at ambient temperature. The reaction mixture was evaporated in vacuo to dryness and the residue was dissolved in DMF (20 ml) and the solution used as it was for the next step reaction.

(E) 1-Methyl-indole-2,5-dicarboxylic acid bis-{[5-(2-carbamimidoyl-ethylcarbamoyl)-1-methyl-1H-pyrrol-3-yl]-amide}, 20

To a stirred solution of compound 6 (110 mg, 0.40 mmole) in methanol (20 ml) was added 10% Pd/C (Degussa type, Aldrich) (0.1 g). The flask was evacuated and then flushed 3 times with hydrogen and finally filled with hydrogen at 40 to 50 psi. The resultant suspension was stirred vigrously at 23° C. for 1 hour. The suspended material was filtered off through a pad of Celite in a Buchner funnel and then the funnel was rinsed several times with a small portion of MeOH. The combined filtrate and washings was evaporated in vacuo to dryness. The resulted 4-amino-1-methyl-1H-pyrrole-2-carboxylic acid (2-carbamidoyl-ethyl)-amide was used for the next step without purification.

A solution of 1-methyl-indole-2,5-dicarboxylic acid di(2, 3,5,6-tetrafluorophenyl) ester 19 (2.0 ml, 0.2 mmole; see Example 19) and freshly prepared (as described above) 4-amino-1-methyl-1H-pyrrole-2-carboxylic acid (2-carbamidoyl-ethyl)-amide (0.4 mmole) in dry DMF (2.0 ml) was kept at ambient temperature for 72 hours and evaporated. The residue was re-precipitated from MeOH-ether, the precipitate was dried in vacuo, dissolved in 0.1 TFA and purified by HPLC (Vydac 12 μm C$_{18}$ 2.2×25 cm column, 0% to 60% acetonitrile gradient over 30 minutes, flow 20 mL/min) to give 1-methyl-indole-2,5-dicarboxylic acid bis-{[5-(2-carbamimidoyl-ethylcarbamoyl)-1-methyl-1H-pyrrol-3-yl]-amide} 20, as a bis-trifluoroacetate salt: mg (18%). The structure was confirmed by ES MS.

Example 8

Synthesis of 1H-indole-2,5-dicarboxylic acid bis-{[2-(2-amino-ethylcarbamoyl)-1-1H-indol-5-yl]-amide}

(A) 5-({1-[2-(2-ethoxycarbonyl-1H-indol-5-ylcarbamoyl)-1H-indol-5-yl]-methanoyl}-amino)-1H-indole-2-carboxylic acid ethyl ester, 21

To a stirred solution of 5-nitroindole-2-carboxylic acid ethyl ester (220 mg, 0.93 mmole) in methanol (10 ml) was added 10% Pd/C (Degussa type, Aldrich) (0.1 g). The flask was evacuated and then flushed 3 times with hydrogen and finally filled with hydrogen at 40 to 50 psi. The resultant suspension was stirred vigrously at 23° C. for 1 hour. The suspended material was filtered off through a pad of Celite in a Buchner funnel and then the funnel was rinsed several times with a small portion of MeOH. The combined filtrate and washings was evaporated in vacuo to dryness. The resulted 4-amino-1-methyl-1H-pyrrole-2-carboxylic acid (2-carbamidoyl-ethyl)-amide was used for the next step without purification.

A solution of compound 2 (200 mg, 0.372 mmole) and freshly prepared of 5-aminoindole-2-carboxylic acid ethyl ester (as described above) methyl 4-amino-1-methyl-1H-pyrrole-2-carboxylate in dry DMF (5.0 ml) was kept at ambient temperature for 48 hours and evaporated. The residue was re-precipitated from DMF (1.0 ml)-0.01 M HCl (10 ml). The precipitate was collected on the filter, washed with water (3×5 ml) end ether (2×3 ml) and dried in vacuo over phosphorus pentoxide to give 142 mg (66%) of 5-({1-[2-(2-ethoxycarbonyl-1H-indol-5-ylcarbamoyl)-1H-indol-5-yl]-methanoyl}-amino)-1H-indole-2-carboxylic acid ethyl ester 21. The structure was confirmed by ES MS and $^1$H-NMR.

(B) 1H-Indole-2,5-dicarboxylic acid bis-{[2-(2-amino-ethylcarbamoyl)-1-1H-indol-5-yl]-amide}, 22

A solution of 5-({1-[2-(2-ethoxycarbonyl-1H-indol-5-ylcarbamoyl)-1H-indol-5-yl]-methanoyl}-amino)-1H-indole-2-carboxylic acid ethyl ester 21 (115 mg, 0.2 mmole) and ethylenediamine-1,2 (1.5 ml) in dry DMF (2.0 ml) was kept at 55 C. for 16 h and evaporated. The residue was dissolved in 0.1 TFA and purified by HPLC (Vydac 12 μm C$_{18}$ 2.2×25 cm column, 0% to 60% acetonitrile gradient over 30 minutes, flow 20 mL/min) to give 1H-indole-2,5-dicarboxylic acid bis-{[2-(2-amino-ethylcarbamoyl) 1-1H-indol-5-yl]-amide} 22, as a bis-trifluoroacetate salt: 62 mg (%). ES MS: 606.27 (M+H$^+$).

Example 9

Synthesis of 1H-Indole-2,5-dicarboxylic acid bis-{ [5-(2-guanidino-ethylcarbamoyl)-1-methyl-1H-pyrrol-3-yl]-amide}

(A) MMT-NHCH$_2$CH$_2$NH$_2$, 23

MMT-Cl (15.44 g, 50 mmole) was added dropwise to a stirred solution of ethylenediamine (24.0 g, 400 mmole) in DCM (500 ml) at 0 C. The reaction mixture was kept at ambient temperature for 2 h, washed with NaHCO$_3$ (5×100 ml) and water (3×100 ml), dried over sodium sulfate and evaporated. The residue was chromatographed over a silica gel column (5.0×25 cm) using mixture of chloroform/MeOH (19:1+0.01% of ammonia), as eluent to give 11.38 g (68%) of MMT-NHCH$_2$CH$_2$N—H$_2$ 23 as light yellow foam. The structure was confirmed by $^1$-NMR.

(B) MMT-NHCH$_2$CH$_2$NHC(=N-Boc)NH-Boc, 24

A solution of MMT-NHCH$_2$CH$_2$NH$_2$ 23 (8.06 g, 24.24 mmole), 1-H-pyrazole-1-[N,N'-bis(tert-butoxycarbonyl) carboxamidine (6.02 g, 19.4 mmole) in MeCN (100 ml) was stirred for 16 h at ambient temperature and evaporated. The residue was coevaporated with toluene (3×100 ml) and chromatographed over a silica gel column (2.5×25 cm) using mixture of hexane/AcOEt (9:1), as eluent to give 10.71 g (96%) of MMT-NHCH$_2$CH$_2$NHC(=N-Boc)NH-Boc 24. The structure was confirmed by ES MS and $^1$-NMR.

(C) NH$_2$CH$_2$CH$_2$NHC(=N-Boc)NH-Boc, 25

To a stirred solution of MMT-NHCH$_2$CH$_2$NHC(=N-Boc)NH-Boc 24 (7.0 mg, 12.2 mmole) in the mixture AcOEt/MeOH (3:1, 200 ml) was added 10% Pd/C (Degussa type, Aldrich) (1.0 g). The flask was evacuated and then flushed 3 times with hydrogen and finally filled with hydrogen at 40 to 50 psi. The resultant suspension was stirred vigrously at 23° C. for 24 hour. The suspended material was filtered off through a pad of Celite in a Buchner funnel and then the funnel was rinsed several times with a small portion of MeOH. The combined filtrate and washings was evaporated in vacuo to dryness. The resulted compound $NH_2CH_2CH_2NHC(=N-Boc)NH-Boc$ 25 was used for the next step without purification.

(D) 1H-Indole-2,5-dicarboxylic acid bis-{[5-(2-guanidino-ethylcarbamoyl)-1-methyl-1H-pyrrol-3-yl]-amide}, 26

A solution of compound 10 (78.2 mg, 0.10 mmole) and $NH_2CH_2CH_2NHC(=N-Boc)NH-B$ 25 (144 mg, 0.25 mmole) in dry DMF (1.0 ml) was kept at ambient temperature for 24 hours and evaporated. The residue was dissolved in the mixture TFA/DCM/anisole (49/49/2), kept at ambient temperature for 1 h and evaporated. The residue was dissolved in 0.1% TFA purified by HPLC (Vydac 12 μm $C_{18}$ 2.2×25 cm column, 0% to 60% acetonitrile gradient over 30 minutes, flow 20 mL/min) to give 1H-indole-2,5-dicarboxylic acid bis-{[5-(2-guanidino-ethylcarbamoyl)-1-methyl-1H-pyrrol-3-yl]-amide}, 26, as a bis-trifluoroacetate salt: 56 mg (38%). ES MS: 618.32 (M+H).

Example 10

Synthesis of 1H-pyrrole-2,5-dicarboxylic acid bis-{[5-(2-carbamimidoyl-ethylcarbamoyl)-1-propyl-1H-pyrrol-3-yl]-amide} 30

(A) Pyrrole-2,5-dicarboxylic acid (31)

Pyrrole-2,5-dicarbaldehyde was prepared in three steps according to the literature (R. Miller and K. Olsson, *Acta Chemica Scandinavica* B, 1981, 35, 303–304) from pyrrole-2-carboxaldehyde. $^1$H NMR (DMSO-$d_6$) δ13.08 (br. S), 9.74 (s), 7.04 (s).

Pyrrole-2,5-dicarbaldehyde (0.21 g, 1.71 mmol) was dissolved in 35 ml of hot water and placed in a hot water bath (95–100° C.). A solution of $KMnO_4$ (0.788 g, 5.13 mmol) in 10 ml of water was added dropwise in a period of 5 min. The reaction mixture was stirred at 95–100° C. for 1 h, and was then cooled to 70° C. The brown precipitates ($MnO_2$) were filtered off and washed with water. The filtrate was acidified at 0° C. with 5 M HCl to pH 2, evaporated to dryness, and dried under high vacuum. The product was dissolved in 80 ml of anhydrous EtOH and the solution was filtered through a funnel. The filtrate was evaporated to give a brown solid (0.25 g), which was used in next reaction without further purification. ESI MS: 154.00 (M−H$^+$). $^1$H NMR (DMSO-$d_6$) δ12.68 (br. S), 12.17 (s), 6.72 (s).

(B) Pyrrole-2,5-dicarboxylic acid dipentafluorophenyl ester (32)

To a solution of pyrrole-2,5-dicarboxylic acid (0.24 g) in 10 ml of anhydrous DMF in the presence of triethylamine (0.48 ml, 3.42 mmol) was added dropwise pentafluorophenyl trifluoroacetate in 2 min at 0° C. The reaction mixture was warmed up slowly to room temperature and stirred at room temperature overnight. After evaporation of solvent, the residue was dissolved in 30 ml of ethyl acetate, washed with water 30 ml×3) and dried over $Na_2SO_4$. The solvent was evaporated and the product was adsorbed onto silica gel, which was placed on the top of silica gel column to run the flash chromatography by using toluene-ethyl acetate (30:1) as eluent. The product as small crystals were obtained (0.406 g). $^{19}$F NMR (CDCl$_3$) δ-152.13 (d), -156.80 (t), -161.60 (t). The total yield for the above two steps reaction was 49%.

(C) 1H-Pyrrole-2,5-dicarboxylic acid bis-{[5-(2-carbamimidoyl-ethylcarbamoyl)-1-propyl-1H-pyrrol-3-yl]-amide} (33)

General Procedure A: To a solution of 4-nitro-1-propyl-1H-pyrrole-2-carboxylic acid (2-carbamimidoyl-ethyl)-amide (52 mg, 0.2 mmol) in 15 ml of MeOH was added 20 mg of 5% Pd/C under argon. The reaction mixture was flashed with hydrogen and shaken under hydrogen at 30 psi for 30 min. The catalyst was removed by filtration through celite and washed with methanol. The filtrate was evaporated to dryness to give 4-amino-1-propyl-1H-pyrrole-2-carboxylic acid (2-carbamimidoyl-ethyl)-amide 34. This product was immediately used in next step reaction.

General Procedure B: A mixture of above amine 34 and pyrrole-2,5-dicarboxylic acid dipentafluorophenyl ester 32 (34.1 mg, 0.07 mmol) in 2 ml of anhydrous DMF under argon was stirred at 55° C. overnight. The product was directly purified by reverse phase HPLC (Zorbax SB-C18 2.2×25 cm; Mobile phase: A=water with 0.1% TFA, B=$CH_3CN$ with 0.1% TFA; Gradient: 0 to 60% B, 40 min; Flow rate: 10 ml/min). The purified compound was transferred to its HCl salt by dissolving it in 2 ml of methanol, following addition 0.5 ml of saturated ethanol with HCl gas or 4 N HCl in dioxane at 0° C. The solution was diluted with 40 ml of cold anhydrous ether and the precipitates were collected and dried. The total yield was 21.2 mg (45%). ESI MS: 594.32 (M+H$^+$). 297.66 (M/2+H$^+$).

Example 11

Synthesis of 1H-pyrrole-2,5-dicarboxylic acid bis-{[5-(2-carbamimidoyl-ethylcarbamoyl)-1-(3-methyl-butyl)-1H-pyrrol-3-yl]-amide} 35

1-(3-Methyl-butyl)-4-nitro-1H-pyrrole-2-carboxylic acid (2-carbamimidoyl-ethyl)-amide 36 (60 mg, 0.2 mmol) was reduced to 4-amino-1-(3-methyl-butyl)-1H-pyrrole-2-carboxylic acid (2-carbamimidoyl-ethyl)-amide 37 by hydrogenation according to general procedure A in example 10.

Pyrrole-2,5-dicarboxylic acid dipentafluorophenyl ester 32 (34.1 mg, 0.07 mmol) was condensed with above amine according to general procedure B in example 10 to give 35 (24.2 mg, 48%). ESI MS: m/z 650.39 (M+H$^+$), 325.69 (M/2+H$^+$).

Example 12

Synthesis of 1H-pyrrole-2,5-dicarboxylic acid bis-{[5-(2-carbamimidoyl-ethylcarbamoyl)-1-methyl-1H-pyrrol-3-yl]-amide} 38

1-Methyl-4-nitro-1H-pyrrole-2-carboxylic acid (2-carbamimidoyl-ethyl)-amide 39 (47.8 mg, 0.2 mmol) was reduced to 4-amino-1-methyl-1H-pyrrole-2-carboxylic acid (2-carbamimidoyl-ethyl)-amide 40 by hydrogenation according to general procedure A in example 10.

Pyrrole-2,5-dicarboxylic acid dipentafluorophenyl ester 32 (34.1 mg, 0.07 mmol) was condensed with above amine according to general procedure B in example 10 to give 38 (31.5 mg, 74%). ESI MS: 538.26 (M+H$^+$) 269.63 (M/2+H$^+$).

Example 13

Synthesis of thiophene-2,5-dicarboxylic acid bis-{[5-(3-carbamimidoyl-propylcarbamoyl)-1-(3-methyl-butyl)-1H-pyrrol-3-yl]-amide} 41

(A) N-(3-Cyanopropyl)phthalimide (42)

A mixture of potassium phthalimide (8.48 g, 0.046 mol) and 4-bromopropylcyanide (6.4 g, 0.043 mol) in 50 ml of anhydrous DMF was stirred at 90° C. for 2 h. After dilution with 300 ml of water, the aqueous solution was extracted with chloroform (80 ml×3). The combined chloroform solution was washed with 0.5% NaOH aqueous solution (80 ml) and water (100 ml), and dried over anhydrous Na2SO4. After evaporation of chloroform, an oil was obtained and 300 ml of water was added. The oil was rapidly solidified. The solid formed was collected by filtration, washed with water, and dried under high vacuum. The product was recrystallized from methanol which was diluted with water, to give white crystals (7.75 g, 84%). $^1$H NMR (CDCl$_3$) δ7.87 (dd, 2H), 7.75 (dd, 2H), 3.83 (t, 2H), 2.44 (t, 2H), 2.09 (quintet, 2H).

(B) 3-Amino-propylcyanide hydrochloride (43)

A mixture of N-(3-cyanopropyl)phthalimide (7.56 g, 35.29 mmol) and hydrazine hydrate (4.4 g, 88.22 mmol) in 20 ml of ethanol was stood at room temperature overnight. After the solution was diluted with 8 ml of water, it was adjusted to pH 3.5 with hydrochloric acid and the precipitates were removed by filtration. The filtrate was evaporated to a small volume. The residue was cooled to 0° C. and then treated with 10 N NaOH solution (6 ml). This basic solution was extracted with chloroform (80 ml×4). The combined chloroform solution was dried over $Na_2SO_4$ and evaporated to dryness. The residue was extracted with ether (100 ml) and precipitated after anhydrous HCl was passed through ether solution. A white solid was obtained (2.2 g, 51%). $^1$H NMR (DMSO-$d_6$) δ8.12 (br, s), 2.82 (m, 2H), 2.61 (t, 2H), 1.86 (quintet, 2H).

(C) 1-(3-Methyl-butyl)-4-nitro-1H-pyrrole-2-carboxylic acid ethyl ester (44)

4-Nitro-1H-pyrrole-2-carboxylic acid ethyl ester (3.69 g, 20.04 mmol) was dissolved in 100 ml of hot anhydrous ethanol and the solution was cooled to room temperature. 30 ml of sodium ethoxide (about 1M) in ethanol was added. The reaction mixture was stirred at room temperature for 20 min and 1-bromo-3-methylbutane (8 ml) was added. The mixture was stirred at reflux for 6 h and cooled to room temperature and then poured into water. The pale yellow precipitates were collected by filtration, washed with water, and dried to give the product (1.48 g, 29%).

(D) 1-(3-Methyl-butyl)-4-nitro-1H-pyrrole-2-carbonyl chloride (45)

1-(3-Methyl-butyl)-4-nitro-1H-pyrrole-2-carboxylic acid ethyl ester (1.44 g,) was dissolved in 50 ml of methanol and 25 ml of 20% aqueous NaOH was added. The reaction mixture was stirred at 50° C. for 1.5 h until there was no starting material checked by TLC. The reaction mixture was concentrated to about 20 ml, 200 ml of water was added. The resulting solution was neutralized with 5 M hydrochloric acid to pH 2 and the precipitates formed were collected by filtration, washed with water and dried to give 1-(3-methyl-butyl)-4-nitro-1H-pyrrole-2-carboxylic acid (1.29 g, 99%). $^1$H NMR (DMSO-$d_6$) δ13.12 (br. s, 1H), 8.27 (d, 1H), 7.26 (d, 1H), 4.36 (t, 2H), 1.59 (dd, 2H), 1.50 (dt, 1H), 0.88 (d, 6H).

The acid was suspended in 15 ml of $SOCl_2$. The reaction mixture was stirred at reflux under argon for 4 h, cooled to room temperature, and evaporated. To the residue was added 80 ml of anhydrous toluene and the toluene evaporated. This was repeated three times. The residue was dissolved in 20 ml of anhydrous benzene, which was frozen and lyophilized to give a white powder (1.26 g, 99%).

(E) 1-(3-Methyl-butyl)-4-nitro-1H-pyrrole-2-carboxylic acid (3-cyano-propyl)-amide (46)

To a mixture of the acid chloride 45 (0.6 g, 2.45 mmol) and 3-aminopropylcyanide hydrochloride (0.31 g, 2.57 mmol) in anhydrous toluene was added 1.5 ml of anhydrous pyridine. The reaction mixture was stirred at 50° C. overnight and then evaporated to dryness. The product was purified by chromatography using toluene-ethyl acetate (2:1) to yield white crystals (0.623 g, 87%). $^1$H NMR (DMSO-$d_6$) δ8.46 (t, 1H), 8.17 (d, 1H), 7.39 (d, 1H), 4.37 (t, 2H), 3.27 (quintet, 2H), 2.53 (d, 2H), 1.77 (quintet, 2H), 1.60–1.42 (q and quintet, 3H), 0.87 (d, 6H).

(F) 1-(3-Methyl-butyl)-4-nitro-1H-pyrrole-2-carboxylic acid (3-carbamimidoyl-propyl)-amide hydrochloride (47)

48 (0.6 g, 2.05 mmol) was dissolved in 25 ml of anhydrous ethanol and the solution was cooled to 0° C. in an ice-bath. Then hydrogen chloride gas dried through concentrated $H_2SO_4$ was bubbled through the solution for 1.5 h. The reaction flask was stopped by using a rubber stopper. The above saturated solution was stirred at room temperature for 4 h and was placed in a refrigerator overnight. Evaporation of solvent gave an oil. To the residue was added 80 ml of anhydrous toluene and the toluene evaporated. This was repeated twice. The white solid obtained was dried under high vacuum.

The product was dissolved in 40 ml of anhydrous ethanol and anhydrous ammonia gas was bubbled through the solution at room temperature for 1.5 h. The flask was stopped by using a rubber stopper. The reaction solution was stirred at 50° C. for 1 h and left at room temperature overnight. The solvent was evaporated and co-evaporated with anhydrous toluene twice. The residue was dried under high vacuum, then dissolved in 1 ml of anhydrous methanol and the solution was diluted with 45 ml of cold anhydrous ether. The precipitates were collected by centrifuge and dried to give a white powder (0.63 g, 89%). ESI MS: 310.19 (M+H$^+$). $^1$H NMR (DMSO-$d_6$) δ8.97 (br. s, 2H), 8.56 (br, s, 3H), 8.18 (d, 1H), 7.44 (d, 1H), 4.37 (t, 2H), 3.21 (q, 2H), 2.40 (t, 2H), 1.80 (quintet, 2H), 1.56 (quintet, 2H), 1.46 (quintet, 1H), 0.87 (d, 6H).

(G) Thiophene-2,5-dicarboxylic acid bis-{[5-(3-carbamimidoyl-propylcarbamoyl)-1-(3-methyl-butyl)-1H-pyrrol-3-yl]-amide} (49)

1-(3-Methyl-butyl)-4-nitro-1H-pyrrole-2-carboxylic acid (3-carbamimidoyl-propyl)-amide hydrochloride (47) (48.4 mg, 0.14 mmol) was reduced to 4-amino-1-(3-methyl-butyl)-1H-pyrrole-2-carboxylic acid (3-carbamimidoyl-propyl)-amide 50 by hydrogenation according to general procedure A in example 10.

5-Pentafluorophenylcarbamoyl-thiophene-2-carboxylic acid pentafluorophenyl ester 50 (25.2 mg, 0.05 mmol) was condensed with above amine 51 according to general procedure B in example 10 to give GL800918 (28.7 mg, 75%). ESI MS: 695.35 (M+H$^+$), 348.18 (M/2+H$^+$).

Example 14

Synthesis of thiophene-2,5-dicarboxylic acid bis-{[5-(4-carbamimidoyl-butylcarbamoyl)-1-(3-methyl-butyl)-1H-pyrrol-3-yl]-amide} 52

1-(3-Methyl-butyl)-4-nitro-1H-pyrrole-2-carboxylic acid (5-carbamimidoyl-pentyl)-amide hydrochloride 53 (50.4 mg, 0.14 mmol) was reduced to 4-amino-1-(3-methyl-butyl)-1H-pyrrole-2-carboxylic acid (5-carbamimidoyl-pentyl)-amide 54 by hydrogenation according to general procedure A in example 10.

5-Pentafluorophenylcarbamoyl-thiophene-2-carboxylic acid pentafluorophenyl ester 50 (25.2 mg, 0.05 mmol) was condensed with above amine 54 according to general procedure B to give 52 (28.3 mg, 71%). ESI MS: 723.39 (M+H$^+$), 362.20 (M/2+H$^+$).

Example 15

Synthesis of 1H-pyrazole-3,5-dicarboxylic acid bis-{[5-(3-carbamimidoyl-propylcarbamoyl)-1-(3-methyl-butyl)-1H-pyrrol-3-yl]-amide} 55

1-(3-Methyl-butyl)-4-nitro-1H-pyrrole-2-carboxylic acid (3-carbamimidoyl-propyl)-amide hydrochloride (47) (17.3 mg, 0.05 mmol) was reduced to 4-amino-1-(3-methyl-butyl)-1H-pyrrole-2-carboxylic acid (3-carbamimidoyl-propyl)-amide 51 by hydrogenation according to general procedure A in example 10.

5-Pentafluorophenylcarbamoyl-2H-pyrazole-3-carboxylic acid pentafluorophenyl ester 56 (8.8 mg, 0.018 mmol) was condensed with above amine 51 according to general procedure B in example 10 to give 55 (5.6 mg, 41%). ESI MS: 679.43 (M+H$^+$), 340.22 (M/2+H$^+$).

Example 16

Synthesis of 1H-pyrazole-3,5-dicarboxylic acid bis-{[5-(4-carbamimidoyl-butylcarbamoyl)-1-(3-methyl-butyl)-1H-pyrrol-3-yl]-amide} 57

1-(3-Methyl-butyl)-4-nitro-1H-pyrrole-2-carboxylic acid (5-carbamimidoyl-pentyl)-amide hydrochloride 53 (18 mg, 0.05 mmol) was reduced to 4-amino-1-(3-methyl-butyl)-1H-pyrrole-2-carboxylic acid (5-carbamimidoyl-pentyl)-amide 54 by hydrogenation according to general procedure A in example 10.

5-Pentafluorophenylcarbamoyl-2H-pyrazole-3-carboxylic acid pentafluorophenyl ester 56 (8.8 mg, 0.018 mmol) was condensed with above amine 54 according to general procedure B in example 10 to give GL190472 (5.2 mg, 37%). ESI MS: 707.46 (M+H$^+$), 354.24 (M/2+H$^+$).

Example 17

Synthesis of N,N'-Bis-[5-(3-carbamimidoyl-propylcarbamoyl)-1-(3-methyl-butyl)-1H-pyrrol-3-yl]-terephthalamide 58

1-(3-Methyl-butyl)-4-nitro-1H-pyrrole-2-carboxylic acid (3-carbamimidoyl-propyl)-amide hydrochloride 47 (50 mg, 0.15 mmol) was reduced to 4-amino-1-(3-methyl-butyl)-1H-pyrrole-2-carboxylic acid (3-carbamimidoyl-propyl)-amide 51 by hydrogenation according to general procedure A in example 10.

Terephthalic acid dipentafluorophenyl ester 59 (30 mg, 0.06 mmol) was condensed with above amine 51 according to general procedure B in example 10 to give GL324265 (9.4 mg, 21%). ESI MS: 689.40 (M+H$^+$), 345.21 (M/2+H$^+$).

Example 18

Synthesis of N,N'-bis-[5-(4-carbamimidoyl-butylcarbamoyl)-1-(3-methyl-butyl)-1H-pyrrol-3-yl]-terephthalamide 60

1-(3-Methyl-butyl)-4-nitro-1H-pyrrole-2-carboxylic acid (5-carbamimidoyl-pentyl)-amide hydrochloride 53 (54 mg, 0.15 mmol) was reduced to 4-amino-1-(3-methyl-butyl)-1H-pyrrole-2-carboxylic acid (5-carbamimidoyl-pentyl)-amide 54 by hydrogenation according to general procedure A in example 10.

Terephthalic acid dipentafluorophenyl ester 59 (30 mg, 0.06 mmol) was condensed with above amine 54 according to general procedure B in example 10 to give 60 (29.9 mg, 63%). ESI MS: 359.23 (M/2+H$^+$).

Example 19

Synthesis of pyridine-2,5-dicarboxylic acid bis-{[5-(3-carbamimidoyl-propylcarbamoyl)-1-(3-methyl-butyl)-1H-pyrrol-3-yl]-amide} 61

1-(3-Methyl-butyl)-4-nitro-1H-pyrrole-2-carboxylic acid (3-carbamimidoyl-propyl)-amide hydrochloride (47) (48.4 mg, 0.14 mmol) was reduced to 4-amino-1-(3-methyl-butyl)-1H-pyrrole-2-carboxylic acid (3-carbamimidoyl-propyl)-amide 51 by hydrogenation according to general procedure A in example 10.

Pyridine-2,5-dicarboxylic acid dipentafluorophenyl ester 62 (25 mg, 0.05 mmol) was condensed with above amine according to general procedure B in example 10 to give 61 (35.7 mg, 89%). ESI MS: 345.74 (M/2+H$^+$).

Example 20

Synthesis of pyridine-2,5-dicarboxylic acid bis-{[5-(4-carbamimidoyl-butylcarbamoyl)-1-(3-methyl-butyl)-1H-pyrrol-3-yl]-amide} 63

1-(3-Methyl-butyl)-4-nitro-1H-pyrrole-2-carboxylic acid (5-carbamimidoyl-pentyl)-amide hydrochloride 53 (54 mg, 0.15 mmol) was reduced to 4-amino-1-(3-methyl-butyl)-1H-pyrrole-2-carboxylic acid (5-carbamimidoyl-pentyl)-amide 54 by hydrogenation according to general procedure A in example 10.

Pyridine-2,5-dicarboxylic acid dipentafluorophenyl ester 62 (30 mg, 0.06 mmol) was condensed with above amine 54 according to general procedure B in example 10 to give 63 (28.5 mg, 57%). ESI MS: 718.46 (M+H$^+$), 359.73 (M/2+H$^+$).

Example 21

Synthesis of pyrazine-2,5-dicarboxylic acid bis-{[5-(3-carbamimidoyl-propylcarbamoyl)-1-(3-methyl-butyl)-1H-pyrrol-3-yl]-amide} 64

1-(3-Methyl-butyl)-4-nitro-1H-pyrrole-2-carboxylic acid (3-carbamimidoyl-propyl)-amide hydrochloride (47) (52 mg, 0.15 mmol) was reduced to 4-amino-1-(3-methyl-butyl)-1H-pyrrole-2-carboxylic acid (3-carbamimidoyl-propyl)-amide 51 by hydrogenation according to general procedure A in example 10.

Pyrazine-2,5-dicarboxylic acid dipentafluorophenyl ester 65 (30 mg, 0.06 mmol) was condensed with above amine 51 according to general procedure B in the example 10 to give 64 (30 mg, 65%). ESI MS: 691.40 (M+H$^+$), 346.20 (M/2+H$^+$).

Example 22

Synthesis of pyrazine-2,5-dicarboxylic acid bis-{[5-(4-carbamimidoyl-butylcarbamoyl)-1-(3-methyl-butyl)-1H-pyrrol-3-yl]-amide} 66

1-(3-Methyl-butyl)-4-nitro-1H-pyrrole-2-carboxylic acid (5-carbamimidoyl-pentyl)-amide hydrochloride 53 (54 mg, 0.15 mmol) was reduced to 4-amino-1-(3-methyl-butyl)-1H-pyrrole-2-carboxylic acid (5-carbamimidoyl-pentyl)-amide 54 by hydrogenation according to general procedure A in example 10.

Pyrazine-2,5-dicarboxylic acid dipentafluorophenyl ester 65 (30 mg, 0.06 mmol) was condensed with above amine according to general procedure B in example 10 to give 66 (29 mg, 61%). ESI MS: 360.22 (M/2+H$^+$).

Example 23

Synthesis of $N^1,N^4$-bis-[5-(3-carbamimidoyl-propylcarbamoyl)-1-(3-methyl-butyl)-1H-pyrrol-3-yl]-2-methyl-terephthalamide 67

1-(3-Methyl-butyl)-4-nitro-1H-pyrrole-2-carboxylic acid (3-carbamimidoyl-propyl)-amide hydrochloride (47) (52 mg, 0.15 mmol) was reduced to 4-amino-1-(3-methyl-butyl)-1H-pyrrole-2-carboxylic acid (3-carbamimidoyl-propyl)-amide 51 by hydrogenation according to general procedure A in example 10.

2-Methyl-terephthalic acid dipentafluorophenyl ester 68 (30.7 mg, 0.06 mmol) was condensed with above amine DS-c-2 according to general procedure B to give 67 (20.5 mg, 44%). ESI MS: 352.22 (M/2+H$^+$).

Example 24

Synthesis of N$^1$,N$^4$-bis-[5-(4-carbamimidoyl-butylcarbamoyl)-1-(3-methyl-butyl)-1H-pyrrol-3-yl]-2-methyl-terephthalamide 69

1-(3-Methyl-butyl)-4-nitro-1H-pyrrole-2-carboxylic acid (5-carbamimidoyl-pentyl)-amide hydrochloride 53 (54 mg, 0.15 mmol) was reduced to 4-amino-1-(3-methyl-butyl)-1H-pyrrole-2-carboxylic acid (5-carbamimidoyl-pentyl)-amide 54 by hydrogenation according to general procedure A in example 10.

2-Methyl-terephthalic acid dipentafluorophenyl ester 68 (30.7 mg, 0.06 mmol) was condensed with above amine 54 according to general procedure B in example 10 to give 69 (25 mg, 52%). ESI MS: 366.23 (M/2+H$^+$).

Example 25

Synthesis of N,N'-bis-[5-(3-carbamimidoyl-propylcarbamoyl)-1-(3-methyl-butyl)-1H-pyrrol-3-yl]-2,5-dimethyl-terephthalamide 70

1-(3-Methyl-butyl)-4-nitro-1H-pyrrole-2-carboxylic acid (3-carbamimidoyl-propyl)-amide hydrochloride (47) (52 mg, 0.15 mmol) was reduced to 4-amino-1-(3-methyl-butyl)-1H-pyrrole-2-carboxylic acid (3-carbamimidoyl-propyl)-amide 51 by hydrogenation according to general procedure A in example 10.

2,5-Dimethyl-terephthalic acid dipentafluorophenyl ester 71 (31.6 mg, 0.06 mmol) was condensed with above amine according to general procedure B in example 10 to give 70 (19.1 mg, 40%). ESI MS: 359.22 (M/2+H$^+$).

Example 26

Synthesis of N,N'-bis-[5-(4-carbamimidoyl-butylcarbamoyl)-1-(3-methyl-butyl)-1H-pyrrol-3-yl]-2,5-dimethyl-terephthalamide 72

1-(3-Methyl-butyl)-4-nitro-1H-pyrrole-2-carboxylic acid (5-carbamimidoyl-pentyl)-amide hydrochloride 53 (54 mg, 0.15 mmol) was reduced to 4-amino-1-(3-methyl-butyl)-1H-pyrrole-2-carboxylic acid (5-carbamimidoyl-pentyl)-amide 54 by hydrogenation according to general procedure A in example 10.

2,5-Dimethyl-terephthalic acid dipentafluorophenyl ester 71 (31.6 mg, 0.06 mmol) was condensed with above amine 54 according to general procedure B in example 10 to give 72 (22.8 mg, 46%). ESI MS: 373.24 (M/2+H$^+$).

Example 27

Synthesis of 1H-indole-2,5-dicarboxylic acid bis-{[5-(3-carbamimidoyl-propylcarbamoyl)-1-(3-methyl-butyl)-1H-pyrrol-3-yl]-amide} 73

1-(3-Methyl-butyl)-4-nitro-1H-pyrrole-2-carboxylic acid (3-carbamimidoyl-propyl)-amide hydrochloride (47) (48.4 mg, 0.14 mmol) was reduced to 4-amino-1-(3-methyl-butyl)-1H-pyrrole-2-carboxylic acid (3-carbamimidoyl-propyl)-amide 51 by hydrogenation according to general procedure A in example 10.

1H-Indole-2,5-dicarboxylic acid bis-(pentafluorophenyl-amide) 74 (26.8 mg, 0.05 mmol) was condensed with above amine 51 according to general procedure B in example 10 to give 73 (29.6 mg, 74%). ESI MS: 728.42 (M+H$^+$), 364.71 (M/2+H$^+$).

Example 28

Synthesis of 1H-indole-2,5-dicarboxylic acid bis-{[5-(4-carbamimidoyl-butylcarbamoyl)-1-(3-methyl-butyl)-1H-pyrrol-3-yl]-amide} 75

1-(3-Methyl-butyl)-4-nitro-1H-pyrrole-2-carboxylic acid (5-carbamimidoyl-pentyl)-amide hydrochloride 53 (50.4 mg, 0.15 mmol) was reduced to 4-amino-1-(3-methyl-butyl)-1H-pyrrole-2-carboxylic acid (5-carbamimidoyl-pentyl)-amide 54 by hydrogenation according to general procedure A in example 10.

1H-Indole-2,5-dicarboxylic acid bis-(pentafluorophenyl-amide) 74 (26.8 mg, 0.05 mmol) was condensed with above amine according to general procedure B in example 10 to give 75 (13 mg, 31%). ESI MS: 756.44 (M+H$^+$), 378.73 (M/2+H$^+$).

Example 29

Synthesis of 1H-indole-2,5-dicarboxylic acid bis-{[2-(2-ethylamino-ethylcarbamoyl)-1H-indol-5-yl]-amide} 76

(A) 5-Nitro-1H-indole-2-carboxylic acid (2-ethylamino-ethyl)-amide (77)

A fine powder of 5-nitro-2-indolecarboxylic acid ethyl ester (0.8 g, 3.41 mmol) was suspended in 2 ml of N-ethylethylenediamine under argon and the reaction mixture was stood at 55° C. overnight. The mixture was co-evaporated with toluene to dryness. The brown solid obtained was dissolved in 6 ml of ethyl acetate and 40 ml of ether was added to precipitate the product. After centrifugation, the liquid was poured out and the solid was washed with 30 ml of ether and dried to give small brown crystals (0.77 g, 82%). ESI MS: 277.11 (M+H$^+$), 299.09 (M+Na$^+$). $^1$H NMR (DMSO-d$_6$) δ8.67 (d, 1H), 8.04 (dd, 1H), 7.55 (d, 1H), 7.37 (s), 3.36 (m, 3H), 2.69 (q, 2H), 2.55 (q, 2H), 0.99 (t, 3H).

(B) Ethyl-(2-{[1-(5-nitro-1H-indol-2-yl)-methanoyl]-amino}-ethyl)-carbamic acid dimethyl-ethyl ester (78)

Compound 77 (0.12 g, 0.434 mmol) was dissolved in 3 ml of DMF and 0.48 ml of 1.0 M di-tert-butyl dicarbonate in THF was added. The reaction mixture was stirred at room temperature for 20 min until the reaction completed by TLC. The solvent was evaporated to dryness and a brown solid formed was recrystallized from MeOH—H$_2$O to give brown crystals (0.139 g, 85%). ESI MS: 377.15 (M+H$^+$), 399.13 (M+Na$^+$).

(C) 1H-Indole-2,5-dicarboxylic acid bis-{[2-(2-ethylamino-ethylcarbamoyl)-1H-indol-5-yl]-amide} (76)

Compound 78 (127 mg, 0.336 mmol) was reduced to 79 by hydrogenation according to general procedure A in example 10. A mixture of above amine DS13a and 1H-indole-2,5-dicarboxylic acid bis-(pentafluorophenyl-amide) 74 (45 mg, 0.084 mmol) in 2 ml of anhydrous DMF under argon was stirred at 55° C. overnight. The solvent was evaporated to dryness. The residue was dissolved in 5 ml of TFA/anisole (8:2) and the mixture was kept at room temperature for 1 h. The product was precipitated by ether and purified by HPLC described in general procedure B in example 10 to give 76 (22 mg, 40%). ESI MS: 662.27 (M+H$^+$), 331.64 (M/2+H$^+$).

Example 30

Synthesis of 1H-indole-2,5-dicarboxylic acid bis-{[2-(2-propylamino-ethylcarbamoyl)-1H-indol-5-yl]-amide} 80

(A) 5-Nitro-1H-indole-2-carboxylic acid (2-propylamino-ethyl)-amide (81)

Similar procedure as described for preparation of 81 from 5-nitro-2-indolecarboxylic acid ethyl ester (0.8 g, 3.41 mmol) and N-propylethylenediamine (2 ml) gave a brown solid (0.84 g, 85%). ESI MS: 291.13 (M+H$^+$). $^1$H NMR (DMSO-d$_6$) δ8.68 (d, 1H), 8.04 (d, 1H), 7.55 (d, 1H), 7.37 (s, 1H), 3.35 (m, 3H), 2.68 (q, 2H), 2.49 9 (q, 2H), 1.40 (tt, 2H), 0.84 (t, 3H).

(B) (2-{[1-(5-Nitro-1H-indol-2-yl)-methanoyl]-amino}-ethyl)-propyl-carbamic acid dimethyl-ethyl ester (82)

Similar procedure as described for preparation of 78 from compound 81 (0.12 g, 0.413 mmol) gave brown powder (0.142 g, 88%). ESI MS: 391.17 (M+H$^+$), 413.15 (M+Na$^+$).

(C) 1H-Indole-2,5-dicarboxylic acid bis-{[2-(2-propylamino-ethylcarbamoyl)-1H-indol-5-yl]-amide} (80)

Compound 82 (131.2 mg, 0.336 mmol) was reduced to 83 by hydrogenation according to general procedure A in example 10. Similar procedure as described for the preparation of 76 from condensation of compound 83 with 1H-indole-2,5-dicarboxylic acid bis-(pentafluorophenyl-amide) 74 (45 mg, 0.084 mmol) followed deprotection of Boc group and purification by HPLC gave GL496564 (39.4 mg, 63%). ESI MS: 690.31 (M+H$^+$), 345.66 (M/2+H$^+$).

Example 31

Synthesis of 1-Octyl-1H-indole-2,5-dicarboxylic acid-84

Sodium hydride (60% suspension, 125 mg, 5 mmol) was added to a stirred solution of 1H-indole-2,5-dicarboxylic acid (525 mg, 2 mmol) in dry DMF (10 mL) and maintained at ambient temperature for 1 hour. The reaction was cooled to 0° C. and then octyl bromide (1.5 mL, 13 mmol) was added. After 3 days the reaction was quenched by addition of 5% aqueous NH4Cl. The mixture was concentrated to dryness and then purified on a silica gel column using toluene. The product was then dissolved in 30 mL ethanol and 10 mL of 2 M NaOH was added. The solution was heated at 55° C. for 2 days. The ethanol was removed in vacuo and the resulting aqueous solution was acidified with 0.01 M HCl to pH 3. The resulting precipitate was filtered and rinsed twice with water. The isolated product was dried by evaporation from absolute ethanol (3×) to give 460 mg (73%) of Cl. $^1$H NMR (DMSO): 8.44 (d, 1H, H-4 indole), 8.01 (dd, 1H, H-6 indole), 7.35 (m, 2 H, H-3&7 indole), 4.43–4.35 (m, 4H, Octyl), 1.4–1.2 (m, 10H, octyl), 0.865 (m, 3H, octyl) MS: 316 [M–H]

Example 32

Synthesis of 1-Octyl-1H-indole-2,5-dicarboxylic acid dipentafluorophenyl ester-85

84 (460 mg, 1.45 mmol) and pentafluorophenol (560 mg, 3.045 mmol) was dissolved in dry DMF (7.25 mL) and then 628 mg (3.05 mmol) of dicyclohexylcarbodiimide dissolved in dry DMF (7.25 mL) was added. The reaction was maintained at ambient temperature for 3 days. The reaction was filtered through paper to remove precipitated urea and concentrated. The residue was taken up in EtOAc (50 mL) and filtered again. The solution was concentrated and then dissolved in 10 mL of dry dioxane and freeze-dried to afford C2 (823 mg, 87%).

Example 33

Synthesis of 1-Octyl-1H-indole-2,5-dicarboxylic acid bis-{[5-(2-carbamimidoyl-ethylcarbamoyl)-1-methyl-1H-pyrrol-3-yl]-amide}-86

90 mg (0.325 mmol) of freshly reduced (as described above) "amino-pyrrole(N1-methyl) amidine" was dissolved in dry DMF (1.25 mL) and added to 65 mg (0.1 mmol) of 84. The reaction was maintained at 40° C for 3 days. The product was precipitated with 40 mL cold diethyl ether, decanted and rinsed once more with ether. The crude product was taken up into 0.1% aqueous TFA and purified by HPLC (Vydac 12 M C$_{18}$ 2.2×25 cm column, 0% to 60% acetonitrile gradient over 30 minutes, 20 mL/min.) to afford 86 as the bis-trifluoroacetate salt. This was dissolved in 2 mL dry MeOH, cooled to –20° C. and then 1 mL 4 M HCl/dioxane was added. The solution was precipitated with 40 mL cold ether to afford 86 as the bis-HCl salt (13.1 mg). MS: 350.7 [M+2H]/2

Example 34

Synthesis of 1-Propyl-1H-indole-2,5-dicarboxylic acid-87

Sodium hydride (60% suspension, 125 mg, 5 mmol) was added to a stirred solution of 1H-indole-2,5-dicarboxylic acid (525 mg, 2 mmol) in dry DMF (10 mL) and maintained at ambient temperature for 1 hour. The reaction was cooled to 0° C. and then propyl bromide (0.275 mL, 3 mmol) was added. After 3 days the reaction was quenched by addition of 5% aqueous NH$_4$Cl. The mixture was concentrated to dryness and then purified on a silica gel column using 5% EtOAc/toluene. The product was then dissolved in 30 mL ethanol and 10 mL of 2 M NaOH was added. The solution was heated at 55° C. for 2 days. The ethanol was removed in vacuo and the resulting aqueous solution was acidified with 0.01 M HCl to pH 3. The resulting precipitate was filtered and rinsed twice with water. The isolated product was dried by evaporation from absolute ethanol (3×) to give 340 mg (67%) of 87. $^1$H NMR (CDCl$_3$): 8.38 (s, 1H, H-4 indole), 7.87 (d, 1H, H-6 indole), 7.71 (d, 1 H, H-7 indole), 7.44 (d, 1 H, H-3 indole), 4.53 (m, 2H, Propyl), 1.7 (m, 2H, propyl), 0.81 (m, 3H, propyl) MS: 246 [M–H]

Example 35

Synthesis of 1-Propyl-1H-indole-2,5-dicarboxylic acid dipentafluorophenyl ester-88

84 (340 mg, 1.33 mmol) and pentafluorophenol (514 mg, 2.8 mmol) was dissolved in dry DMF (6.65 mL) and then 575 mg (2.8 mmol) of dicyclohexylcarbodiimide dissolved in dry DMF (6.65 mL) was added. The reaction was maintained at ambient temperature for 3 days. The reaction was filtered through paper to remove precipitated urea and concentrated. The residue was taken up in EtOAc (50 mL) and filtered again. The solution was concentrated and then dissolved in 10 mL of dry dioxane and freeze-dried to afford 88 (626 mg, 81%).

Example 36

Synthesis of 1-Propyl-1H-indole-2,5-dicarboxylic acid bis-{[5-(2-carbamimidoyl-ethylcarbamoyl)-1-methyl-1H-pyrrol-3-yl]-amide}-89

90 mg (0.325 mmol) of freshly reduced (as described above) amino-pyrrole(N1-methyl) amidine was dissolved in dry DMF (1.25 mL) and added to 58 mg (0.1 mmol) of 88. The reaction was maintained at 40° C. for 3 days. The product was precipitated with 40 mL cold diethyl ether, decanted and rinsed once with ether. The crude product was taken up into 0.1% aqueous TFA and purified by HPLC (Vydac 12 μM C$_{18}$ 2.2×25 cm column, 0% to 60% acetonitrile gradient over 30 minutes, 20 mL/min.) to afford 89 as the bis-trifluoroacetate salt. This was dissolved in 2 mL dry MeOH, cooled to −20° C. and then 1 mL 4 M HCl/dioxane was added. The solution was precipitated with 40 mL cold ether to afford 89 as the bis-HCl salt (19.3 mg). MS: 315.7 [M+2H]/2

Example 37

Synthesis of 1H-Indole-2,5-dicarboxylic acid bis-([2-(2-methylamino-ethylcarbamoyl)-1H-indol-5-yl]-amide}-90

To 30 mg (0.05 mmol) of "EtO-hnd-hnd-hnd-OEt" was added 1.5 mL of N-methylethylenediamine. The mixture was reacted at 50° C. for 72 hours and then concentrated in vacuo. The residue was taken up into 2 mL DMF and precipitated with 40 mL cold diethyl ether, decanted and rinsed once with ether. The crude product was taken up into 0.1% aqueous TFA and purified by HPLC (Vydac 12 $\mu$M $C_{18}$ 2.2×25 cm column, 0% to 60% acetonitrile gradient over 30 minutes, 20 mL/min.) to afford 90 as the bis-trifluoroacetate salt. This was dissolved in 2 mL dry MeOH, cooled to −20° C. and then 1 mL 4 M HCl/dioxane was added. The solution was precipitated with 40 mL cold ether to afford 90 as the bis-HCl salt (11.5 mg). MS: 317.7 [M+2H]/2

Example 38

Synthesis of 1H-Indole-2,5-dicarboxylic acid bis-[(2-{2-[bis-(2-amino-ethyl)-amino]-ethylcarbamoyl}-1H-indol-5-yl)-amide]-91

To 50 mg (0.087 mmol) of "EtO-Ind-Ind-Ind-OEt" was added 3 mL of Tris-(2-aminoethyl)amine. The mixture was reacted at 55° C. for 24 hours and then precipitated with 40 mL cold diethyl ether, decanted and rinsed once with ether. The crude product was taken up into 0.1% aqueous TFA and purified by HPLC (Vydac 12 M $C_{18}$ 2.2×25 cm column, 0% to 60% acetonitrile gradient over 30 minutes, 20 mL/min.) to afford 91 as the hexa-trifluoroacetate salt. (22.9 mg). MS: 389.7 [M+2H]/2

Example 39

Synthesis of 1H-Indole-2,5-dicarboxylic acid bis-({2-[3-(3-amino-propylamino)-propylcarbamoyl]-1H-indol-5-yl}-amide)-92

To 50 mg (0.087 mmol) of "EtO-Ind-Ind-Ind-OEt" was added 3 mL of 3-aminopropyl-propane-diamine and 1 mL DMF. The mixture was reacted at 55° C. for 48 hours and then precipitated with 40 mL cold diethyl ether, decanted and rinsed once with ether. The crude product was taken up into 0.1% aqueous TFA and purified by HPLC (Vydac 12 M $C_{18}$ 2.2×25 cm column, 0% to 60% acetonitrile gradient over 30 minutes, 20 mL/min.) to afford 92 as the tetrakis-trifluoroacetate salt. (20.4 mg). MS: 374.7 [M+2H]/2

Example 40

Synthesis of 5-Nitro-1-propyl-1H-indole-2-carboxylic acid ethyl ester-93

To 3.69 g (15.75 mmol) of commercial ethyl 5-Nitro-2-carboxy-indole dissolved in 35 mL of DMSO was added 2.01 g (31.5 mmol) of KOH. The reaction was stirred vigorously for 30 mins., at which time 2.86 mL (31.5 mmol) of propyl bromide was added. After 4 hours an additional 5 mL DMSO was added and the reaction was reacted overnight. 1 mL 5% aqueous $NH_4Cl$ was added and poured into toluene (150 mL) and washed with saturated $NaHCO_3$ (100 mL). The aqueous layer was extracted twice with toluene (75 mL each) and the combined organic layers washed with brine (100 mL), dried over $Na_2SO_4$ and concentrated. The product was dissolved in 100 mL dioxane and freeze-dried to give 4.15 g (15.1 mmol, 95%) of 93. $^1$H NMR ($CDCl_3$): 8.64 (s, 1H, H-4 indole), 8.2 (m, 1H, H-6 indole), 7.47–7.42 (m, 2 H, H-7 & H-3 indole), 4.57 (m, 2H, Propyl), 4.45–4.37 (m, 4H, ethyl ester), 1.89–1.8 (m, 2H, propyl), 1.47–1.41 (m, 3H, propyl), 0.98–0.98–0.92 (m, 6H, ethyl ester) MS: 299 [M+Na]

Example 41

Synthesis of 1H-Indole-2,5-dicarboxylic acid bis-{[2-(2-amino-ethylcarbamoyl)-1-propyl-1H-indol-5-yl]-amide}-94

To a solution of 93 (104 mg, 0.375 mmol) in 50 mL anhydrous EtOAc and 25 mL anhydrous methanol was added 10% Pd/C (Degussa type, Aldrich) (0.05 g). The flask was evacuated and flushed with hydrogen three times and finally filled with hydrogen at 40 psi. The suspension was shaken vigourously for 45 mins. at ambient temperature. The suspension was filtered through a Buchner funnel and rinsed several times with methanol. The filtrate and washings were concentrated to dryness. The resulting amino-indole was then dissolved in dry DMF (1 mL) and added to 75 mg (0.15 mmol) "Pfp-Indole-Pfp" in a vial and placed at 55° C. for 24 hours. The crude tris-indole was isolated by addition of 40 mL of 0.001 M HCl to the reaction mixture. The precipitate was isolated by centrifugation and the acidic supernatant decanted. The crude was rinsed and centrifuged once more with 0.001 M HCl and three times with water. The product was dried by evaporation twice from ethanol. Finally, the crude residue was placed in a vial and 2 mL redistilled ethylenediamine was added. The reaction was heated at 55° C. for 72 hrs. and then concentrated in vacuo. The residue was taken up into 2 mL DMF and precipitated with 40 mL cold diethyl ether, decanted and rinsed once with ether. The crude product was taken up into 0.1% aqueous TFA and purified by HPLC (Vydac 12 M $C_{18}$ 2.2×25 cm column, 0% to 60% acetonitrile gradient over 30 minutes, 20 mL/min.) to afford 94 as the bis-trifluoroacetate salt This was dissolved in 2 mL dry MeOH, cooled to −20° C. and then 1 mL 4 M HCl/dioxane was added. The solution was precipitated with 40 mL cold ether to afford 94 as the bis-HCl salt (30.0 mg). MS: 345.7 [M+2H]/2

Example 42

Synthesis of 1-Propyl-1H-indole-2,5-dicarboxylic acid bis-{[2-(2-amino-ethylcarbamoyl)-1-propyl-1H-indol-5-yl]-amide}-95

To a solution of 93 (104 mg, 0.375 mmol) in 50 mL EtOAc and 25 mL methanol was added 10% Pd/C (Degussa type, Aldrich) (0.05 g). The flask was evacuated and flushed with hydrogen three times and finally filled with hydrogen at 40 psi. The suspension was shaken vigourously for 45 mins. at ambient temperature. The suspension was filtered through a Buchner funnel and rinsed several times with methanol. The filtrate and washings were concentrated to dryness. The resulting amino-indole was then dissolved in dry DMF (1 mL) and added to 87 mg (0.15 mmol) 88 in a vial and placed at 55° C. for 24 hours. The crude tris-indole was isolated by addition of 40 mL of 0.001 M HCl to the reaction mixture. The precipitate was isolated by centrifugation and the acidic supernatant decanted. The crude was rinsed and centrifuged once more with 0.001 M HCl and three times with water. The product was dried by evaporation twice from ethanol.

Finally, the crude residue was placed in a vial and 2 mL redistilled ethylenediamine was added. The reaction was heated at 55° C. for 72 hrs. and then concentrated in vacuo. The residue was taken up into 2 mL DMF and precipitated with 40 mL cold diethyl ether, decanted and rinsed once with ether. The crude product was taken up into 0.1% aqueous TFA and purified by HPLC (Vydac 12 M $C_{18}$ 2.2×25 cm column, 0% to 60% acetonitrile gradient over 30 minutes, 20 mL/min.) to afford 95 as the bis-trifluoroacetate salt. This was dissolved in 2 mL dry MeOH, cooled to −20° C. and then 1 mL 4 M HCl/dioxane was added. The solution was precipitated with 40 mL cold ether to afford 95 as the bis-HCl salt (48.5 mg). MS: 366.7 [M+2H]/2

Example 43

Synthesis of 1-Propyl-1H-indole-2,5-dicarboxylic acid bis-{[2-(2-amino-ethylcarbamoyl)-1H-indol-5-yl]-amide}-96

To a solution of commercial ethyl 5-Nitro-2-carboxy-indole (87 mg, 0.37 mmol) in 75 mL EtOAc and 25 mL methanol was added 10% Pd/C (Degussa type, Aldrich) (0.05 g). The flask was evacuated and flushed with hydrogen three times and finally filled with hydrogen at 40 psi. The suspension was shaken vigorously for 45 mins. at ambient temperature. The suspension was filtered through a Buchner funnel and rinsed several times with methanol. The filtrate and washings were concentrated to dryness. The resulting amino-indole was then dissolved in dry DMF (1 mL) and added to 87 mg (0.15 mmol) C5 in a vial and placed at 55° C. for 24 hours. The crude tris-indole was isolated by addition of 40 mL of 0.001 M HCl to the reaction mixture. The precipitate was isolated by centrifugation and the acidic supernatant decanted. The crude was rinsed and centrifuged once more with 0.001 M HCl and three times with water. The product was dried by evaporation twice from ethanol. Finally, the crude residue was placed in a vial and 3 mL redistilled ethylenediamine was added. The reaction was heated at 55° C. for 72 hrs. and then concentrated in vacuo. The residue was taken up into 1 mL DMF and precipitated with 40 mL cold diethyl ether, decanted and rinsed once with ether. The crude product was taken up into 0.1% aqueous TFA and purified by HPLC (Vydac 12 M $C_{18}$ 2.2×25 cm column, 0% to 60% acetonitrile gradient over 30 minutes, 20 mL/min.) to afford 96 as the bis-trifluoroacetate salt. This was dissolved in 2 mL dry MeOH, cooled to −20° C. and then 1 mL 4 M HCl/dioxane was added. The solution was precipitated with 40 mL cold ether to afford 96 as the bis-HCl salt (7.7 mg). MS: 324.7 [M+2H]/2

Example 44

Synthesis of 5-Nitro-1H-indole-2-carboxylic acid-97

To a solution of commercial ethyl 5-Nitro-2-carboxy-indole (10.21 g, 43.6 mmol) in ethanol (220 mL) was added 110 mL of 2 M NaOH. The reaction was stirred at 60° C. for 18 hours. The reaction was then cooled and the ethanol removed in vacuo and then an additional 200 mL water was added. To the vigourously stirring aqueous solution was added 5 M HCl followed by 1 M HCl until pH 4 was attained and the acid product was precipitated. The product was collected by filtration on a Buchner funnel and washed once with dilute HCl (1:40 v/v) and twice with water. The filtrate was dried over $P_2O_5$ in a dessicator in vacuo to afford 8.83 g (42.8, 98%) of acid 97. $^1$H NMR (DMSO): 12.4 (br s, 1H, 1H indole), 8.68 (dd, 1H, H-4 indole), 8.08 (m, 1H, H-6 indole), 7.54 (m, 1H, H-7 indole), 7.34 (dd, 1H, H-3 indole).

Example 45

Synthesis of 5-Nitro-1H-indole-2-carboxylic acid (2-cyano-ethyl)-amide-98

4.5 g (21.8 mmol) of acid 97 was placed in a flask and 100 mL of thionyl chloride was added. The reaction was refluxed at 85° C. for 2.5 hrs under a dry atmosphere. The reaction was cooled to ambient temperature and the mixture concentrated in vacuo. The residue was taken up into 75 mL dioxane and the suspension concentrated in vacuo. Finally, the residue was taken up into 100 mL toluene and the suspension concentrated in vacuo. The residue was suspended in dry dioxane (220 mL) and amino-propionitrile (3.96 mL, 54.5 mmol) was added dropwise. The reaction was stirred at ambient temperature for 18 hrs. and then concentrated in vacuo. The residue was taken into 50 mL DMF and with vigourous stirring 0.001 M HCl was added until pH 3 was attained and then an additional 200 mL 0.001 M HCl was added. The product was collected by filtration on a Buchner funnel and washed twice with water. The filtrate was dried over $P_2O_5$ in a dessicator in vacuo to afford 5.13 g (19.9, 91%) of 98. $^1$H NMR (DMSO): 12.34 (br s, 1H, 1H indole), 9.1 (dd, 1H, H-4 indole), 8.7 (s, 1H, amide NH), 8.04 (m, 1H, H-6 indole), 7.55 (m, 1H, H-7 indole), 7.38 (s, 1H, H-3 indole), 3.54–3.49 (m, 2H), 2.78 (dd, 2H).

Example 46

Synthesis of 5-Nitro-1H-indole-2-carboxylic acid (2-carbamimidoyl-ethyl)-amide-99

Nitrile 98 (2.5 g, 9.68 mmol) was suspended in anhydrous ethanol (75 mL) and cooled to 0° C. The cooled ethanolic suspension was then saturated with dried HCl gas for 5 hours. The gas stream was removed, the flask sealed and kept overnight at 4° C. In the morning, the suspension was concentrated in vacuo and then coevaporated with anhydrous ethanol (100 mL) to afford 3.26 g of imidate ester intermediate. 2.26 g of the crude was suspended in anhydrous ethanol (100 mL), cooled to 0° C. and saturated with anhydrous $NH_3$ gas. After 4 hrs. the gas source was removed, the flask sealed and placed at 4° C. overnight. In the morning, the reaction was concentrated in vacuo and coevaporated once with anhydrous ethanol (100 mL). The residue was suspended in anhydrous ethanol (200 mL), filtered, rinsed with anhydrous ethanol and dried in vacuo to afford 1.89 g (5.86 mmol) of 99. $^1$H NMR (DMSO): 9.1–9.05 (br m, 3H, $H_4$ indole & amidine), 8.75–8.65 (br s, 2 H, amidine), 8.06 (dd, 1H, H-6 indole), 7.57 (d, 1H, H-7 indole), 7.45 (s, 1H, H-3 indole)3.65–3.61 (m, 2H), 2.71–2.66 (m, 2H). MS: 276 [M+H]

Example 47

Synthesis of 1H-Indole-2,5-dicarboxylic acid bis-([2-(2-carbamimidoyl-ethylcarbamoyl)-1H-indol-5-yl]-amide)-100

To a solution of "nitro-indole-amidine" 99 (117 mg, 0.375 mmol) in methanol (30 mL) and EtOAc (10 mL) was added 10% Pd/C (Degussa type, Aldrich) (0.05 g). The flask was evacuated and flushed with hydrogen three times and finally filled with hydrogen at 50 psi. The suspension was shaken vigourously for 45 mins. at ambient temperature. The suspension was filtered through a Buchner funnel and rinsed several times with methanol. The filtrate and washings were concentrated to dryness. The resulting amino-indole was then dissolved in dry DMF (1.9 mL) and added to 75 mg (0.15 mmol) "Pfp-Indole-Pfp" in a vial and placed at 45° C. for 48 hours. The product was precipitated with 40 mL cold diethyl ether, decanted and rinsed once with ether. The crude product was taken up into 0.1% aqueous TFA and purified by HPLC (Vydac 12 M $C_{18}$ 2.2×25 cm column, 0% to 60% acetonitrile gradient over 30 minutes, 20 mL/min.) to afford 100 as the bis-trifluoroacetate salt. This was dissolved in 6 mL dry MeOH, cooled to −20° C. and then 1 mL 4 M HCl/dioxane was added. The solution was precipitated with 40 mL cold ether to afford 100 as the bis-HCl salt (62.0 mg). MS: 330.6 [M+2H]/2

Example 48

Synthesis of 9H-Carbazole-3,6-dicarboxylic acid dipentafluorophenyl ester-101

Commercial carbazole (5.02 g, 30 mmol) was suspended in chlorobenzene (48 mL) and trichloroacetonitrile (7.2 mL, 72 mmol) added. $AlCl_3$ was then added to the stirring reaction mixture. The reaction mixture was fit with reflux condensor under a dry atmosphere and slowly heated to 100° C. After 2 hrs. 20 mL concentrated HCl was added and the temperature increased to 120° C. for 2 hours. The mixture was concentrated in vacuo and then suspended in 2 M KOH (200 mL), refluxed for 1 hour and finally, filtered through a Buchner funnel. The filtrate was adjusted to pH 3 with 5 M HCl, cooled to ambient temperature and filtered. The filtrate was dried by coevaporation from methanol three times to afford 1.86 g of crude diacid.

The crude diacid was dissolved in and concentrated from anhydrous pyridine three times and dissolved in dry DMF (14.5 mL). Diisopropylethylamine (5.05 mL) was added followed by 2.62 mL (15.25 mmol) of pentafluorophenyl-trifluoroacetate. The reaction was stirred at ambient temperature overnight and then concentrated in vacuo. The residue was then purified on a silica gel column using 50% EtOAc/toluene. The product was dissolved in anhydrous benzene (30 mL) and freeze dried to afford 290 mg (0.494 mmol, 7%) of 101. $^1$H NMR ($CDCl_3$): 9.04 (s, 2H, H-4&5), 8.3 (dd, 2H, H-1 &8), 7.64 (d, 2H, H-2&7).

Example 49

9H-Carbazole-3,6-dicarboxylic acid bis-{[2-(2-amino-ethylcarbamoyl)-1H-indol-5-yl]-amide}-102

To a solution of "5-nitro-indole-EDA-Boc" (74 mg, 0.21 mmol) in methanol (25 mL) and EtOAc (25 mL) was added 10% Pd/C (Degussa type, Aldrich) (0.01 g). The flask was evacuated and flushed with hydrogen three times and finally filled with hydrogen at 40 psi. The suspension was shaken vigourously for 45 mins. at ambient temperature. The suspension was filtered through a Buchner funnel and rinsed several times with methanol. The filtrate and washings were concentrated to dryness. The resulting amino-indole was then dissolved in dry DMF (1.0 mL) and added to 57 mg (0.1 mmol) "Pfp-Carbazole-Pfp"-101 in a vial and placed at 50° C. for 20 hours. The Boc-protected product was precipitated with 40 mL cold diethyl ether, decanted and rinsed once with ether. To the residue was added anisole (0.8 mL) and then trifluoroacetic acid (3.2 mL). The solution was maintained at ambient temperature for 30 minutes and then product was precipitated with 40 mL cold diethyl ether, decanted and rinsed twice with ether. The crude product was taken up into 0.1% aqueous TFA and purified by HPLC (Vydac 12 M $C_{18}$ 2.2×25 cm column, 0% to 60% acetonitrile gradient over 30 minutes, 20 mL/min.) to afford 102 as the bis-trifluoroacetate salt. This was dissolved in 6 mL dry MeOH, cooled to −20° C. and then 1 mL 4 M HCl/dioxane was added. The solution was precipitated with 40 mL cold ether to afford 102 as the bis-HCl salt (38.4 mg). MS: 328.7 [M+2H]/2

Example 50

Synthesis of 1H-Indole-2,5-dicarboxylic acid 2-{[2-(2-amino-ethylcarbamoyl)-1H-indol-5-yl]-amide}5-{[2-(2-guanidino-ethylcarbamoyl)-1H-indol-5-yl]-amide}, 103, (Scheme 6)

Loading of the linker. 2.5 g (2.55 mmol) MBHA resin (S=1.02) was swelled in DMF for 5 minutes. 1.06 g (7.65 mmol) 4-hydroxybenzoic acid and 1.03 g (7.65 mmol) HOBt was dissolved in DMF to which 1.18 mL (7.65 mmol) DIC was added. The clear mixture was poured to the resin and was agitated gently for 2 hrs. The resin was drained, washed with DMF (5×). A mixture of 10 mL DMF and 5 mL ethanolamine was added and was agitated overnight at room temperature (18 hrs). Next morning the resin was drained, washed with DMF (3×), DCM (3×), 50% TFA/DCM (2×), DCM (2×), DMF (2×), DCM (2×), methanol (2×), ether (2×) and it was dried to get 2.8 g phenol resin, B1. The degree of substitution was S=0.89 mmol/g resin (calculated from the weight increase).

Loading of the first acid. 1.2 g (5 mmol) N-tert-butyloxycarbonyl-5-aminoindole-2-carboxylic acid (Boc-5Ain-OH) was suspended in 20 mL DCM. 0.78 mL (5 mmol) DIC was added followed by 100 mg (0.8 mmol) DMAP. The suspension became clear within 5 minutes. The clear solution was added to the dry, 2.8 g (2.5 mmol) phenol resin, B1 and the mixture was agitated overnight (18 hrs) at room temperature. Next day the resin was drained, washed with DMF (3×). The unreacted phenolic OH groups were blocked by acetylation with 20% acetic anhydryde in DCM plus 0.5 mL DIEA. The resin was then washed with DMF (3×), DCM (3×), methanol (2×), ether (2×) and was dried resulting in 3.2 g B2. The degree of substitution was about 0.55 mmol/g resin-based on the weight increment.

Synthesis. 160 mg (0.1 mmol) Boc-5Ain-Hba-Resin (B2) was swelled in DCM for ten minutes then was treated with 25% TFA 2% anisol in DCM for 20 minutes. It was washed 3× with DCM and 3× with DMF. The unprotected B3 was coupled in DMF with 151 mg (0.3 mmol) B4 dipeptide (synthesized separately in solution) using 108 mg (0.285 mmol) HBTU and 104 μL (0.6 mmol) DIEA for three hrs resulting in the resin bound tripeptide, B5. The resin was washed with DMF (3×), DCM (3×) and was treated with the TFA/anisol/DCM reagent again for 20 minutes. The TFA was washed out with DCM (3×) and DMF (3×). The free amino containing molecule was treated with 10 fold excess of 1H-Pyrazole-1-carboxamidine hydrochloride (146.6 mg, 1.0 mmol) and DIEA (344 μL, 2.0 mmol) overnight at room temperature to give B6. Finally, the product (103) was cleaved from the resin by treating with EDA at room temperature for 1 hour. The resin was filtered off, the supernatant was evaporated in vacuum and the remaining oil was precipitated from methanol with ether. The precipitate was spun down and was dried. The crude product was purified with HPLC (Vydac 12 μm $C_{18}$ 2.2×25 cm column, 0% to 60% acetonitrile gradient over 30 minutes, flow 20 mL/min). The overall yield was 16.4 mg (24%) 103. ES MS: 648.26 (calcd. for M+H$^+$: 648.28).

Example 51

Synthesis of 1H-Indole-2,5-dicarboxylic acid 5-{[2-(2-amino-ethylcarbamoyl)-1H-indol-5-yl]-amide} 2-{[2-(2-guanidino-ethylcarbamoyl)-1H-indol-5-yl]-amide}, 104

The same amount of tBoc protected peptide-resin (0.1 mmole, Scheme [FILL IN], B5), instead of removing the protecting group was first cleaved from the resin with EDA as described in Example 50. The resulted amine was treated with 146.6 mg (1.0 mmole) of 1H-Pyrazole-1-carboxamidine hydrochloride in DMF (2 mL) solution overnight. The reaction mixture was evaporated to dryness and the remaining oil was dissolved in 5 mL TFA containing 20% anisol. The deprotection was complete in 30 minutes, when the product was precipitated by addition of 45 mL cold diethylether. The precipitate was filtered off, was washed with ether and was dried. The crude product was purified with HPLC (Vydac 12 µm $C_{18}$ 2.2×25 cm column, 0% to 60% acetonitrile gradient over 30 minutes, flow 20 mL/min). The overall yield was 15.2 mg (22%) 104. ES MS: 648.26 (calcd. for M+H$^+$:648.28).

Example 52

Synthesis of 1H-Indole-2,5-dicarboxylic acid bis-{[2-(2-guanidino-ethylcarbamoyl)-1H-indol-5-yl]-amide}, 105

8.2 mg (0.01 mmole) 103 was treated with 14.6 mg (0.1 mmole) of 1H-Pyrazole-1-carboxamidine hydrochloride in DMF (2 mL) solution as described in Example 51. After evaporation, the oily residue was purified with HPLC in the same way. Yield: 15.6 mg (23%) B9. ES MS: 690.27 (calcd. for M+H$^+$:690.30).

Example 53

Synthesis of 1H-Indole-2,5-dicarboxylic acid bis-{[2-(2-amino-ethylcarbamoyl)-1H-indol-6-yl]-amide}, 106

(A) 6-Amino-1H-indole-2-carboxylic acid methyl ester, 107 (R=CH$_3$).

To a solution of 6-Nitro-1H-indole-2-carboxylic acid methyl ester (108) 200 mg (0.91 mmole) in a mixture of methanol/ethylacetate 1:1 10% Pd/C (40 mg) was added. The flask was rinsed 3 times with hydrogen and filled with hydrogen at 30 to 35 psi. The suspension was stirred vigorously at room temperature for 30 minutes. The catalyst was filtered off, the filtrate was evaporated in vacuo to dryness. The resulted 6-amino-1H-indole-2-carboxylic acid methyl ester gave a single spot on TLC (Silica, toluene-ethylacetate 7:3, R$_f$:0.31) and was used for the next step without purification
(B) 1H-Indole-2,5-dicarboxylic acid bis-{[2-methoxycarbonyl-1H-indol-6-yl]-amide}, 109 (R=CH$_3$)

The freshly prepared (as described above) 6-amino-1H-indole-2-carboxylic acid methyl ester (0.91 mmole) was dissolved in 3 mL of dry DMF. 235 mg (0.44 mmole) 1H-Indole-2,5-dicarboxylic acid dipentafluorophenyl ester, 110 (Example 1, Step B) and 156 µL (0.91 mmole) DIEA were added and the mixture was heated under argon at 55° C. for three days then was evaporated to dryness. The oily residue was triturated with ether to give 200 mg (83%) solid product which was pure enough to continue the synthesis without further purification.
(C) 1H-Indole-2,5-dicarboxylic acid bis-{[2-(2-amino-ethylcarbamoyl)-1H-indol-6-yl]-amide}, 106

50 mg (0.091 mmole) 109 (R=CH$_3$) was dissolved in 2 mL neat 1,2-ethylenediamine and was kept at 55° C. overnight (18 hrs) and was evaporated to dryness. The residue was dissolved in 2 mL methanol and was precipitated by addition of 45 mL of ether. The precipitate was spun down, the pallet was washed twice with ether and was dried. The crude 106 was purified with HPLC (Vydac 12 µm $C_{18}$ 2.2×25 cm column, 0% to 60% acetonitrile gradient over 30 minutes, flow 20 mL/min). The purified compound was transferred to HCl salt by dissolving in 2 mL methanol, treating with 1 mL 4N HCl in dioxane and precipitating with ether. The overall yield was 9.1 mg (15%) 106. ES MS: 606.30 (calcd. for M+H$^+$: 606.26).

Example 54

Synthesis of 1H-Indole-2,5-dicarboxylic acid bis-{[2-(3-amino-propylcarbamoyl)-1H-indol-6-yl]-amide}, 111

Compound 111 was synthesized as described for Compound 106 in Example 53, using propane-1,3-diamine in Step C. Yield 8.6 mg (18%); MS: 634.38 (calcd. for M+H$^+$: 634.29).

Example 55

Synthesis of N,N'-Bis-[2-(2-amino-ethylcarbamoyl)-1H-indol-5-yl]-isophthalamide, 112

Compound 112 was synthesized as generally described for Compound 106 in Example 53. Yield 10.9 mg (18%); MS: 567.26 (calcd. for M+H$^+$:567.25).

Example 56

Synthesis of Pyridine-2,6-dicarboxylic acid bis-{[2-(2-amino-ethylcarbamoyl)-1H-indol-5-yl]-amide}, 113

Compound 113 was synthesized as generally described for Compound 106 in Example 53. Yield 23.2 mg (41%); MS: 568.24 (calcd. for M+H$^+$:568.24).

Example 57

Synthesis Pyridine-2,4-dicarboxylic acid bis-{[2-(2-amino-ethylcarbamoyl)-1H-indol-5-yl]-amide}, 114

Compound 114 was synthesized as generally described for Compound 106 in Example 53. Yield 17.1 mg (30%); MS: 568.24 (calcd. for M+H$^+$:568.24).

Example 58

Synthesis Pyridine-3,5-dicarboxylic acid bis-{[2-(2-amino-ethylcarbamoyl)-1H-indol-5-yl]-amide}, 115

Compound 115 was synthesized as generally described for Compound 106 in 53. Yield 30 mg (53%); MS: 568.25 (calcd. for M+H$^+$:568.24).

Example 59

Synthesis N,N'-Bis-[2-(2-amino-ethylcarbamoyl)-1H-indol-6-yl]-isophthalamide, 116

Compound 116 was synthesized as generally described for Compound 106 in Example 53. Yield 34.9 mg (61%); MS: 567.26 (calcd. for M+H$^+$:567.25).

Example 60

Synthesis Pyridine-2,6-dicarboxylic acid bis-{[2-(2-amino-ethylcarbamoyl)-1H-indol-6-yl]-amide}, 117

Compound 117 was synthesized as generally described for Compound 106 in Example 53. Yield 35.5 mg (61%); MS: 568.25 (calcd. for M+H$^+$:568.24).

Example 61

Synthesis Pyridine-2,4-dicarboxylic acid bis-{[2-(2-amino-ethylcarbamoyl)-1H-indol-6-yl]-amide}, 118

Compound 118 was synthesized as generally described for Compound 106 in Example 53. Yield 35.3 mg (61%); MS: 568.26 (calcd. for M+H$^+$:568.24).

Example 62

Synthesis 1H-Pyrazole-3,5-dicarboxylic acid bis-([2-{2-amino-ethylcarbamoyl]-1H-indol-6-yl]-amide}, 119

Compound 119 was synthesized as generally described for Compound 106 in Example 53. Yield 9.6 mg (17%); MS: 557.23 (calcd. for M+H$^+$:557.24).

Example 63

Synthesis Thiophene-2,5-dicarboxylic acid bis-{[2-(2-amino-ethylcarbamoyl)-1H-indol-5-yl]-amide}, 120

Compound 120 was synthesized as generally described for Compound 106 in Example 53. Yield 8.7 mg (15%); MS: 573.19 (calcd. for M+H$^+$:573.21).

Example 64

Synthesis 1H-Pyrazole-3,5-dicarboxylic acid bis-{[2-(2-amino-ethylcarbamoyl)-1H-indol-5-yl]-amide), 121

Compound 121 was synthesized as generally described for Compound 106 in Example 53. Yield 3.7 mg (7%); MS: 557.23 (calcd. for M+H$^+$:557.24).

Example 65

Synthesis 1H-Indole-2,5-dicarboxylic acid bis-{[2-(2-amino-ethylcarbamoyl]-1-methyl-1H benzimidazole-5-yl]-amide}, 122

Compound 122 was synthesized as generally described for Compound 106 in Example 53. Yield 6.8 mg (10%); MS: 636.37 (calcd. for M+H$^+$:636.40).

Example 66

Synthesis 1H-Indole-2,5-dicarboxylic acid bis-({2-[2-(2-hydroxy-ethylamino)-ethylcarbamoyl]-1H-indol-6-yl}-amide), 123

Compound 123 was synthesized as generally described for Compound 106 in 53. Yield 12.5 mg (17%); MS: 694.35 (calcd. for M+H$^+$:694.31).

Example 67

Synthesis of 1H-Indole-2,5-dicarboxylic acid bis-{[2-(2-dimethylamino-ethylcarbamoyl)-1H-indol-6-yl]-amide}, 124
(A) Synthesis of 6-Nitro-1H-indole-2-carboxylic acid (2-dimethylamino-ethyl)-amide, 125

500 mg (2.27 mmole) 6-Nitro-1H-indole-2-carboxylic acid methyl ester was dissolved in 4 mL neat N$^1$,N$^1$-dimethyl-ethane-1,2-diamine, was kept at 55° C. overnight and was evaporated. The oily residue was triturated with n-hexane to give 528 mg (84%) yellow solid which was no further purified. MS: 277.13 (calcd for M+H$^+$:277.13)
(B) Synthesis of 6-Amino-1H-indole-2-carboxylic acid (2-dimethylamino-ethyl)-amide, 126

To a solution of 82.9 mg (0.3 mmole) 125 in a mixture of ethanol/ethylacetate 1:1 10% Pd/C (40 mg) was added. The flask was flushed 3 times with hydrogen and filled with hydrogen at 30 to 35 psi. The suspension was stirred vigorously at room temperature for 30 minutes. The catalyst was filtered off, the filtrate was evaporated in vacuo to dryness. The solid 126 was used for the next step without purification (C) 1H-Indole-2,5-dicarboxylic acid bis-{[2-(2-dimethylamino-ethylcarbamoyl)-1H-indol-6-yl]-amide}, 124

The freshly prepared (as described above) 126 was dissolved in 3 mL dry DMF. 54 mg (0.1 mmole) 1-H-indole-2,5-dicarboxylic acid dipentafluorophenyl ester (Example 1, Step B) and 103 μL (0.6 mmole) DIEA were added and the mixture was heated under argon at 55° C. overnight (18 hrs) then was evaporated to dryness. The crude 124 was purified with HPLC (Vydac 12 μm C$_{18}$ 2.2×25 cm column, 0% to 60% acetonitrile gradient over 30 minutes, flow 20 mL/min). The purified compound was converted to HCl salt by dissolving in 2 mL methanol, treating with 1 mL 4N HCl in dioxane and precipitating with ether to yield 7.0 mg (9.5%) 124. ES MS: 662.29 (calcd. for M+H$^+$:662.32).

Example 68

Synthesis of 1H-Indole-2,5-dicarboxylic acid bis-{[2-(3-dimethylamino-propylcarbamoyl)-1H-indol-5-yl]-amide}, 127

Compound 127 was synthesized as generally described for Compound 124 in Example 67. Yield 16.7 mg (24%); MS: 690.34 (calcd. for M+H$^+$:690.35).

Example 69

Synthesis of 1H-Indole-2,5-dicarboxylic acid bis-{[2-(2-dimethylamino-ethylcarbamoyl)-2,3-dihydro-1H-indol-6-yl]-amide}, 128

Compound 128 was synthesized as generally described for Compound 124 in Example 67. Yield 4.8 mg (7%); MS: 666.33(calcd. for M+H$^+$:666.35).

Example 70

Synthesis of 1H-Indole-2,5-dicarboxylic acid bis-{[2-(2-dimethylamino-propylcarbamoyl)-2,3-dihydro-1H-indol-6-yl]-amide}, 129

Compound 129 was synthesized as described for Compound 124 in Example 67. Yield 23.7 mg (34%); MS: 694.36 (calcd. for M+H$^+$:694.39).

Example 71

Synthesis of 1H-Indole-2,5-dicarboxylic acid bis-({2-[2-(2-hydroxy-ethylamino)-ethylcarbamoyl]-1H-indol-5-yl}-amide), 130
(A) 5-Nitro-1H-indole-2-carboxylic acid [2-(2-hydroxy-ethylamino)-ethyl]-amide, 131

To a solution of 2.34 g (10 mmole) 5-Nitro-1H-indole-2-carboxylic acid ethyl ester, (132) in 25 mL DMF 5.2 g (50 mmole) 2-(2-amino-ethylamino)-ethanol (133) was added and the mixture was kept at 55° C. for 36 hrs under argon atmosphere. It was then evaporated to dryness and the oily residue was dissolved at room temperature in ethanol resulting in an immediate crystal formation. The crystals were filtered off, washed with ethanol (2×) and dried to give 2.08 g product (71%). MS: 293.13 (calcd for M+H$^+$:293.31). $^1$-NMR (DMSO-d$_6$): 8.70–8.67 (m, 2H, amide & indole H-4); 8.04 (dd, 1H, indole H-6); 7.55 (d, 1H, indole H-7); 7.37 (s, 1H, indole H-3); 3.43 (t, 2H, —NH—CH$_2$—CH$_2$—NH—CH$_2$—CH$_2$—OH); 3.39–3.33 (m, 2H, —NH—CH$_2$—CH$_2$—NH—CH$_2$—CH$_2$—OH); 2.71–2.66 (m, 2H, —NH—CH$_2$—CH$_2$—NH—CH$_2$—CH$_2$—OH); 2.59 (t, 2H, —NH—CH$_2$—CH$_2$—NH—CH$_2$—CH$_2$—OH)

(B) 5-Nitro-1H-indole-2-carboxylic acid [(2-(2-hydroxy-ethyl-2-tert-butyloxycarbonyl-amino)-ethyl]-amide, 134

2.08 g (7.12 mmole) 131 was suspended in 10 mL DMF. 1.71 g (7.83 mmole) tBoc$_2$O was added at room temperature. The mixture became clear in ten minutes and the reaction was complete in 1 hr. The DMF was evaporated in vacuo, the remaining solid was crystallized from isopropanol to yield 1.82 g (65%). $^1$-NMR (DMSO-d$_6$):12.33 (s, 1H, indole H-1); 8.79 (s, 1H, CO—NH); 8.69 (s, 1H, indole H-3); 8.03 (dd, 1H, indole H-6); 7.55 (d, 1H, indole H-7); 7.34 (d, 1H, indole H-4); 3.46–3.23 (m, 8H, methylenes); 1.32 (s, 9H, CH$_3$)

(C) 5-Amino-1H-indole-2-carboxylic acid [(2-(2-hydroxy-ethyl-2-tert-butyloxycarbonyl-amino)-ethyl]-amide, 135

To a solution of 196 mg (0.5 mmole) 134 in a mixture of ethanoll/ethylacetate 1:1 10% Pd/C (50 mg) was added. The flask was rinsed 3 times with hydrogen and filled with hydrogen at 30 to 35 psi. The suspension was stirred vigorously at room temperature for 30 minutes. The catalyst was filtered off, the filtrate was evaporated in vacuo to dryness to result in 180 mg (100%) 135 that gave a single spot on TLC (Silica, toluene-ethylacetate 1:9, R$_f$: 0.16) and was used for the next step without purification.

(D) 1H-Indole-2,5-dicarboxylic acid bis-({2-[2-(2-hydroxy-ethylamino)-ethylcarbamoyl]-1H indol-5-yl}-amide), 130

180 mg (0.5 mmole) 135 was dissolved in 3 mL DMF and was reacted with 50 mg (0.1 mmole) 1-H-indole-2,5-dicarboxylic acid dipentafluorophenyl ester and 86 μL (0.5 mmole) DIEA overnight (18 hrs) at 55° C. The mixture was evaporated to drynes in vacuo, the semisolid remaining was triturated with ether to give 190 mg solid 136. The tBoc protecting groups were removed by dissolving it in 5 mL TFA containing 20% anisol and reacting for 30 minutes at room temperature. 40 mL ether was added and the mixture was spun down. The supernatant was discarded, the pallet was washed with ether 3 times and was dried. The crude 130 was purified with HPLC (Vydac 12 μm C$_{18}$ 2.2×25 cm column, 0% to 60% acetonitrile gradient over 30 minutes, flow 20 mL/min). The purified compound was converted to HCl salt by dissolving in 2 mL methanol, treating with 1 mL 4N HCl in dioxane and precipitating with ether to yield 29.3 mg (42.3%) 130. ES MS: 694.29 (calcd. for M+H$^+$: 694.31).

Example 72

Synthesis 1H-Indole-2,5-dicarboxylic acid bis-{[2-(3-amino-2-hydroxy-propylcarbamoyl]-1H indole-5-yl]-amide}, 137

Compound 137 was synthesized as generally described for Compound 130 in Example 71. Yield 58 mg (86%); MS: 666.42 (calcd. for M+H$^+$:666.28).

Example 73

Synthesis of 1H-Indole-2,5-dicarboxylic acid bis-{[2-(2-guanidino-ethylcarbamoyl)-1H-indol-6-yl]-amide}, 138

To a solution of 23.8 mg (35 μmole) 106 (synthesized as described in example 53) in 2 mL of DMF 51 mg (0.35 mmole) 1-H-pyrazole-1-carboxamidine hydrochloride and 73 μL (0.42 mmole) DIEA was added. The mixture was kept overnight (18 hrs) at room temperature then was evaporated to dryness. The oily residue was purified with HPLC (Vydac 12 μm C$_{18}$ 2.2×25 cm column, 0% to 60% acetonitrile gradient over 30 minutes, flow 20 mL/min). The purified compound was converted to HCl salt by dissolving in 2 mL methanol, treating with 1 mL 4N HCl in dioxane and precipitating with ether to yield 3.3 mg (13%) 138. ES MS: 690.41 (calcd. for M+H$^+$:690.30).

Example 74

Synthesis 1H-Indole-2,5-dicarboxylic acid bis-{[2-(2-guanidino-propylcarbamoyl)-1H-indol-6-yl]-amide}, 139

Compound 139 was synthesized as generally described for Compound 138 in Example 73. Yield 2.0 mg (8%); MS: 718.43 (calcd. for M+H$^+$:718.33).

Example 75

Synthesis 1H-Indole-2,5-dicarboxylic acid bis-{[2-(2-guanidino-ethylcarbamoyl)-1H-indol-5-yl]-amide}, 140

Compound 140 was synthesized as generally described for Compound 138 in Example 53. Yield 50 mg (24%); MS: 690.39 (calcd. for M+H$^+$:690.30).

Example 76

Synthesis 1H-Indole-2,5-dicarboxylic acid bis-{[2-(3-guanidino-2-hydroxypropylcarbamoyl]-1H indole-5-yl]-amide}, 141

Compound 141 was synthesized as described for Compound 138 in Example 53. Yield 9.1 mg (60%); MS: 750.37 (calcd. for M+H$^+$:750.32).

Example 77

Synthesis of 1H-Indole-2,5-dicarboxylic acid bis-([2-(2-amino-ethylcarbamoyl)-1-ethoxymethyl-1H-indol-5-yl]}-amide}, 142

A solution of 2.3 g (10 mmole) 5-nitro-1H-indole-2-carboxylic acid ethyl ester (143) in DMF was cooled to 0° C. and 598 mg (15 mmole) NaH (60% in mineral oil) was added with vigorous stirring. The flask was evacuated and kept under vacuum for 1 hr. 1.44 mL (15.5 mmole) ethoxymethyl-chloride was added still at 0° C. The mixture was further stirred for 1 hr at room temperature then it was evaporated in vacuo to dryness. The oily residue was extracted with ether, the ether phase was evaporated and the remaining solid material was crystallized twice from 70 mL iso-proppyl alcohol. Yield 1.7g (58%) 144.

146 mg (0.5 mmole) 144 was reduced, coupled with 1-H-indole-2,5-dicarboxylic acid dipentafluorophenyl ester (Example 1, Step B), reacted with ethylenediamine and purified as described for 106 in Example 53. Yield 40 mg (55%) B507-b. ES MS: 722.49 (calcd. for M+H$^+$:722.34).

Example 78

Synthesis of 1H-Indole-2,5-dicarboxylic acid bis-{ [2-(2-amino-ethylcarbamoyl)-1-methoxyethoxymethyl-1H-indol-5-yl]}-amide}, 145

Compound 145 was synthesized as generally described for 142 in Example 77 using methoxyethoxymethyl chloride. Yield 22 mg (27%). ES MS: 782.52 (calcd. for M+H$^+$: 782.36).

Example 79

Synthesis of 1H-Indole-2,5-dicarboxylic acid bis-{ [2-(2-amino-ethylcarbamoyl)-1-methoxymethyl-1H-indol-5-yl]}-amide), 146

Compound 146 was synthesized as described for 142 in Example 77 using methoxymethyl chloride. Yield 20.3 mg (29%). ES MS: 694.35 (calcd. for M+H$^+$:694.31).

Example 80

Synthesis of of 1H-Indole-2,5-dicarboxylic acid bis-{[2-(2-L-alanyl-amido-ethylcarbamoyl)-1H-indol-6-yl]-amide}, 147

To a solution of 25 mg (0.031 mmole) of 106 (Example 53) in DMF 21.5 mg (0.075 mmole) Boc-Ala-Opfp (148) and 22 μL (0.124 mmole) DIEA was added and the mixture was stirred at room temperature for 2 hrs. It was evaporated to dryness, triturated with ether and dried. The tBoc protecting group was removed by dissolving the dried solid material in TFA containing 20% anisol and reacting for 30 minutes. The crude product was precipitated with ether, washed 3 times with ether and was dried. It was purified with HPLC (Vydac 12 μm $C_{18}$ 2.2×25 cm column, 0% to 60% acetonitrile gradient over 30 minutes, flow 20 mL/min). The purified compound was converted to HCl salt by dissolving in 2 mL methanol, treating with 1 mL 4N HCl in dioxane and precipitating with ether to yield 16 mg (68%) 147. ES MS: 748.31 (calcd. for $M+H^+$:748.33).

Example 81

Synthesis of of 1H-Indole-2,5-dicarboxylic acid bis-{[2-(2-L-phenylalanyl-amido-ethylcarbamoyl)-1H-indol-6-yl]-amide}, 149

Compound 149 was synthesized as described for Compound 147 in Example 80, using Fmoc-Phe-Opfp (150), except the Fmoc protecting group was removed by treatment of the triturated and dried material with 20% piperidine in DMF for 30 minutes at room temperature. The piperidine reagent was evaporated and the remaining oil was triturated with ether. The solid crude product was purified and converted to HCl salt as described above in Example 80. Yield 19.2 mg (68%) 149; MS: 900.37 (calcd. for $M+H^+$:900.40).

Example 82

Synthesis of of 1H-Indole-2,5-dicarboxylic acid bis-{[2-(2-L-leucyl-amido-ethylcarbamoyl)-1H-indol-6-yl]-amide}, 151

Compound 151 was synthesized as described for Compound 149 in Example 81, using Fmoc-Leu-OPfp. Yield 15.4 mg (59%) 151; MS: 832.41 (calcd. for $M+H^+$:832.43).

Example 83

Synthesis of of 1H-Indole-2,5-dicarboxylic acid bis-{[2-(2-L-isoleucyl-amido-ethylcarbamoyl)-1H-indol-6-yl]-amide}, 152

Compound 152 was synthesized as described for Compound 149 in Example 81, using Fmoc-Ile-OPfp. Yield 13.2 mg (50%) 152; MS: 832.41 (calcd. for $M+H^+$:832.43).

Example 84

Synthesis of of 1H-Indole-2,5-dicarboxylic acid bis-{[2-(2-L-valyl-amido-ethylcarbamoyl)-1H-indol-6-yl]-amide}, 153

Compound 153 was synthesized as described for Compound 149 in Example 81, using Fmoc-Val-OPfp. Yield 17.1 mg (68%) 153; MS: 804.39 (calcd. for $M+H^+$:804.40).

Example 85

Synthesis of of 1H-Indole-2,5-dicarboxylic acid bis-{[2-(2-glycyl-amido-ethylcarbamoyl)-1H-indol-6-yl]-amide}, 154

Compound 154 was synthesized as described for Compound 149 in Example 81, using Fmoc-Gly-OPfp. Yield 18.5 mg (82%) 154; MS: 720.29 (calcd. for $M+H^+$:720.30).

Example 86

Synthesis of of 1H-Indole-2,5-dicarboxylic acid bis-{[2-(2-L-glutamyl-amido-ethylcarbamoyl)-1H-indol-6-yl]-amide}, 155

Compound 155 was synthesized as described for Compound 149 in Example 81, using Fmoc-Glu(OtBu)-OPfp. The OtBu protecting group was removed as described for the removing of tBoc group in Example 80. Yield 3.2 mg (11%) 155; MS: 864.37 (calcd. for $M+H^+$:864.35).

Example 87

Synthesis of of 1H-Indole-2,5-dicarboxylic acid bis-{[2-(2-L-ornithyl-amido-ethylcarbamoyl)-1H-indol-6-yl]-amide}, 156

Compound 156 was synthesized as described for Compound 155 in Example 86, using Fmoc-Orn(Boc)-OPfp. Yield 18.4 mg (71%) 156; MS: 834.42 (calcd. for $M+H^+$:834.41).

Example 88

Synthesis of of 1H-Indole-2,5-dicarboxylic acid bis-{[2-(2-(N-acetyl-gamma-L-glutamyl)-amido-ethylcarbamoyl)-1H-indol-6-yl]-amide}, 157

Compound 157 was synthesized as described for Compound 147 in Example 80, using Boc-Glu(OSu)-OBzl, except the Bzl and tBoc protecting groups were removed by treatment of the triturated and dried material with a mixture of 500 μL thioanisol, 250 μL EDT 5 mL TFA and 500 μL TFMSA for 2 hrs at room temperature. The crude product was precipitated with ether, purified and converted to HCl salt as described in 80. Yield 6.8 mg (25%) 157; MS: 472.67 (calcd. for $M+2H^+$:472.67).

Example 89

Synthesis of of 1H-Indole-2,5-dicarboxylic acid bis-{[2-(2-L-norleucyl-amido-ethylcarbamoyl)-1H-indol-6-yl]-amide}, 158

Compound 158 was synthesized as described for Compound 149 in Example 81, using Fmoc-Nle-OPfp. Yield 15.3 mg (61%) 158; MS: 832.41 (calcd. for $M+H^+$:832.43).

Example 90

Synthesis of 1H-Indole-2,5-dicarboxylic acid bis-{[2-(2-L-lysyl-amido-ethylcarbamoyl)-1H-indol-6-yl]-amide}, 159

Compound 159 was synthesized as described for Compound 147 in Example 80, using Boc-Lys(Boc)-OSu. Yield 19 mg (73%) 159; MS: 862.45 (calcd. for $M+H^+$:862.45).

Example 91

Synthesis of of 1H-Indole-2,5-dicarboxylic acid bis-{[2-(2-(L-2,3-diaminopropyl)-amido-ethylcarbamoyl)-1H-indol-5-yl]-amide}, 160

51 mg (0.093 mmole) Fmoc-Dap(Fmoc)-OH was dissolved in DMF. 22 μL (0.124 mmole) DIEA was added followed by 15 μL (0.087 mmole) TFA-Opfp and the mixture was stirred for 15 minutes at room temperature. This activated acid solution was used to synthesize 160 as described for Compound 149 in Example 81. Yield 11.9 (49%) 160; MS: 778.37 (calcd. for $M+H^+$:778.356).

Example 92

Synthesis of of 1H-Indole-2,5-dicarboxylic acid bis-{[2-(2-(L-2,4-diaminobutyryl)-amido-ethylcarbamoyl)-1H-indol-5-yl]-amide}, 161

Compound 161 was synthesized as described for Compound 160 in Example 91, using Fmoc-Dab(Fmoc)-OH. Yield 9.3 mg (38%) 161; MS: 805.39 (calcd. for M+H$^+$: 805.39).

Example 93

Synthesis of of 1H-Indole-2,5-dicarboxylic acid bis-{[2-(2-(N-methyl-L-valyl)-amido-ethylcarbamoyl)-1H-indol-5-yl]-amide}, 162

Compound 162 was synthesized as described for Compound 160 in Example 91, using Fmoc-MeVal-OH. Yield 19.1 mg (76%) 162; MS: 832.42 (calcd. for M+H$^+$:832.43).

Example 94

Synthesis of of 1H-Indole-2,5-dicarboxylic acid bis-{[2-(2-L-arginyl-amido-ethylcarbamoyl)-1H-indol-6-yl]-amide}, 163

Compound 163 was synthesized as described for Compound 157 in Example 88, using Boc-Arg(Z$_2$)-OSu. Yield 23.3 mg (84%) 163; MS: 918.45 (calcd. for M+H$^+$:918.46).

Example 95

Synthesis of of 1H-Indole-2,5-dicarboxylic acid bis-{[2-(2-(L-2,3-diaminopropyl)-amido-ethylcarbamoyl)-1H-indol-6-yl]-amide}, 164

Compound 164 was synthesized as described for Compound 160 in Example 91. Yield 12.9 mg (55%) 164; MS: 778.35 (calcd. for M+H$^+$:778.36).

Example 96

Synthesis of of 1H-Indole-2,5-dicarboxylic acid bis-{[2-(2-(L-2,4-diaminobutyryl)-amido-ethylcarbamoyl)-1H-indol-6-yl]-amide}, 165

Compound 165 was synthesized as described for Compound 161 in Example 92. Yield 11.2 mg (46%) 165; MS: 805.39 (calcd. for M+H$^+$:805.39).

Example 97

Synthesis of of 1H-Indole-2,5-dicarboxylic acid bis-{[2-(2-(N-methyl-L-valyl)-amido-ethylcarbamoyl)-1H-indol-6-yl]-amide}, 166

Compound 166 was synthesized as described for Compound 162 in Example 93. Yield 12.7 mg (50%) 166; MS: 832.42 (calcd. for M+H$^+$:832.43).

Example 98

Synthesis of of 1H-Indole-2,5-dicarboxylic acid bis-{[2-(2-L-threonyl-amido-ethylcarbamoyl)-1H-indol-5-yl]-amide}, 167

Compound 167 was synthesized as described for Compound 147 in Example 80, using Boc-Thr-OSu. Yield 20.4 mg (84%) 167; MS: 808.37 (calcd. for M+H$^+$:808.36).

Example 99

Synthesis of of 1H-Indole-2,5-dicarboxylic acid bis-{[2-(2-threonyl-amido-ethylcarbamoyl)-1H-indol-6-yl]-amide}, 168

Compound 168 was synthesized as described for Compound 147 in Example 80, using Boc-Thr-OSu. Yield 18.8 mg (77%) 168; MS: 808.37 (calcd. for M+H$^+$:808.36).

Example 100

Synthesis of of 1H-Indole-2,5-dicarboxylic acid bis-{[2-(2-glycyl-amido-ethylcarbamoyl)-1H-indol-5-yl]-amide}, 169

Compound 169 was synthesized as described for Compound 147 in Example 80, using Boc-Gly-OSu. Yield 13.2 mg (73%) 169; MS: 720.28 (calcd. for M+H$^+$:720.30).

Example 101

Synthesis of of 1H-Indole-2,5-dicarboxylic acid bis-{[2-(2-acetamino-ethylcarbamoyl)-1H-indol-5-yl]-amide}, 170

Compound 170 was synthesized as described for Compound 147 in Example 80, using acetic anhydride, except no protecting group removal was necessary. Yield 11 mg (60%) 170; MS: 690.16 (calcd. for M+H$^+$:690.28).

Example 102

Synthesis of of 1H-Indole-2,5-dicarboxylic acid bis-{[2-(2-L-glutamyl-amido-ethylcarbamoyl)-1H-indol-5-yl]-amide}, 171

Compound 171 was synthesized as described for Compound 149 in Example 81, using Fmoc-Glu(OtBu)-OPfp. The OtBu protecting group was removed as described for the removing of tBoc group in Example 80. Yield 5 mg (23%) 171; MS: 864.37 (calcd. for M+H$^+$: 864.35).

Example 103

Synthesis of of 1H-Indole-2,5-dicarboxylic acid bis-{[2-(2-L-lysyl-amido-ethylcarbamoyl)-1H-indol-5-yl]-amide}, 172

Compound 172 was synthesized as described for Compound 147 in Example 80, using Boc-Lys(Boc)-OSu. Yield 19 mg (88%) 172; MS: 862.45 (calcd. for M+H$^+$:862.45).

Example 104

Synthesis of of 1H-Indole-2,5-dicarboxylic acid bis-{[2-(2-L-valyl-amido-ethylcarbamoyl)-1H-indol-5-yl]-amide}, 173

Compound 173 was synthesized as described for Compound 149 in Example 81, using Fmoc-Val-OPfp. Yield 15.4 mg (76%) 173; MS: 804.41 (calcd. for M+H$^+$:804.40).

Example 105

Synthesis of of 1H-Indole-2,5-dicarboxylic acid bis-{[2-(2-L-aspartyl-amido-ethylcarbamoyl)-1H-indol-5-yl]-amide}, 174

Compound 174 was synthesized as described for Compound 149 in Example 81, using Fmoc-Asp(OtBu)-OPfp. The OtBu protecting group was removed as described for the removing of tBoc group in Example 80. Yield 9.3 mg (44%) 174; MS: 836.38 (calcd. for M+H$^+$:836.31).

Example 106

Synthesis of Boc-Py-HBA-AMPS (175)

Boc Py (5 mmol, 1.20 g) was dissolved in 20 mL dichloromethane and 0.774 mL (5 mmol) DIC, 100 mg (0.8 mmol) DMAP were added. This solution was added to 2.5 g of Hba-AMPS resin and agitated overnight at room temperature. After filtering the solution off, the resin was washed three times with DMF, three times with dichloromethane, 2 times with methanol and two times with diethyl ether. Each washing volume was approximately equivalent to the volume of the resin. The resin was subsequently dried under high vacuum and weighed. Yield of 175:2.9226 g corresponding to a substitution of 0.76 mmol/g.

Example 107

Synthesis of Boc-5-Ain-HBA-AMPS (176)

Boc-5-Ain (5 mmol, 1.38 g) was dissolved in 20 mL DMF and 2.21 g (2 eq.) BOP, 0.871 mL (2 eq.) DIEA were added. This solution was added to 2.5 g of Hba-AMPS resin and agitated overnight at room temperature. After filtering the solution off, the resin was washed three times with DMF, three times with dichloromethane, 2 times with methanol and two times with diethyl ether. Each washing volume was approximately equivalent to the volume of the resin. The resin was subsequently dried under high vacuum and weighed. Yield of (176): 2.9327 g corresponding to a substitution of 0.626 mmol/g.

Example 108

Exemplary Synthesis Procedure for Compound (177) (Scheme 7)

0.03 mM resin 176 was washed three times with ca. 5 mL DMF and three times with ca. 5 mL dichloromethane. The swelled resin was then washed for 1 minute with a mixture of 25% trifluoroacetic acid/2% anisole in dichloromethane and after draining treated for another 20 minutes with the same mixture. After draining, the resin was washed two times with ca. 5 mL dichloromethane and two times with ca. 5 mL DMF to give unprotected 178. Dipeptide 179 (34.4 mg, 0.09 mmol), synthesized separately in solution, was dissolved in 2 mL DMF and mixed with 32.4 mg HBTU and 30.9 μL DIEA. After 5 min this mixture was added to resin and agitated for 2 hours to give resin-bound tripeptide 180. This resin was treated for 2 hours with 2 mL neat ethylenediamine to give product 177. The resin was filtered off, the solution is evaporated in vacuo and the resulting oil was dissolved in methanol and precipitated with diethyl ether. The resulting precipitate was spun down, the ether decanted and the product dried in vacuo. This crude product was HPLC-purified (Vydac 12 μm, C18 2.2×25 cm column, 0% to 80% aqueous acetonitrile gradient over 20 min, flow rate 20 mL/min) to give purified 177 (see table 1).

Compounds 181–188 were synthesized using the same synthesis procedure as above, but with the following modifications: Compounds 181, 182, 183, 184, and 188 started their synthesis with resin 175, compounds 185, 186, and 187 used resin 176. The amines used, to cleave tripeptide precursors from the resins to form compounds 181 through 188 are listed in table 1 under "Amines Used." All amines were used neat (2 mL each), except for 1,4-diamino butane, which was dissolved in 600 μL tetrahydofuran.

TABLE 1

| Compound Number | Resin Used | Amine Used | Yield in mg | MS found (M + H⁺) | MS calculated (M + H⁺) |
| --- | --- | --- | --- | --- | --- |
| 181 | 175 | 1,4-diamino butane | 7.7 | 575.35 | 575.69 |
| 182 | 175 | Ethylene diantine | 5.4 | 547.30 | 547.64 |
| 183 | 175 | DP | 8.5 | 589.35 | 589.72 |
| 184 | 175 | DE | 9.5 | 575.33 | 575.69 |
| 185 | 176 | 1,4-diamino butane | 8.3 | 611.33 | 611.72 |
| 177 | 176 | Ethylene diamine | 8.6 | 583.30 | 583.67 |
| 186 | 176 | DP | 13.1 | 625.35 | 625.75 |
| 187 | 176 | DE | 14.7 | 611.33 | 611.72 |
| 188 | 175 | Ethanolamine | 21.1 | 548.27 | 548.62 |

Example 109

Exemplary Synthesis Procedure for compound 191 (Scheme 8)

0.03 mM resin 176 was washed three times with ca. 5 mL DMF and three times with ca. 5 mL dichloromethane. The swelled resin was then washed for 1 minute with a mixture of 25% trifluoroacetic acid/2% anisole in dichloromethane and after draining treated for another 20 minutes with the same mixture. After draining, the resin was washed two times with ca. 5 mL dichloromethane and two times with ca. 5 mL DMF to give unprotected 178. Dipeptide 189 (42.2 mg, 0.09 mmol), synthesized separately in solution, was dissolved in 2 mL DMF and mixed with 32.4 mg HBTU and 30.9 μL DIEA. After 5 min this mixture was added to resin and agitated for 2 hours to give resin-bound tripeptide 190. This resin was treated for 2 hours with 2 mL of 2M methylamine in THF to give product 191. The resin was filtered off, the solution was evaporated in vacuo and the resulting oil was dissolved 500 μL anisol and 2 mL TFA. After 30 min stirring, this solution was evaporated in vacuo, dissolved in methanol and precipitated with diethyl ether. The resulting precipitate was spun down, the ether decanted and the product dried in vacuo. This crude product was HPLC-purified (Vydac 12 μm, C18 2.2×25 cm column, 0% to 80% aqueous acetonitrile gradient over 20 min, flow rate 20 mL/min) to give purified 191 (see table 2).

Compounds 192–200 were synthesized using the same synthesis procedure as above, but with the following modifications: Compounds 192, 193, 194, 195, and 200 started their synthesis with resin 175, compounds 196, 197, 198, and 199 used resin 176. The amines used, to cleave tripeptide precursors from the resins to form compounds 192 through 200 are listed in table 2 under "Amines Used." Ethylene diamine was used neat (2 mL), all other amines were used in solution: Methyl amine (2M in THF), 1,4-diamino butane (2 mL dissolved in 600 μL tetrahydofuran), diethylenetriamine (10 eq. in 2 mL THF), N,N'-Bis(3-aminopropyl)-1,3-propanediamine (10 eq. in 2 mL THF), and Tris(2-aminoethyl)amine (10 eq. in 2 mL THF).

TABLE 2

| Compound Number | Resin Used | Amine Used | Yield in mg | MS found (M + H⁺) | MS calculated (M + H⁺) |
| --- | --- | --- | --- | --- | --- |
| 192 | 175 | Methyl amine | 14.3 | 505.25 | 505.56 |
| 193 | 175 | 1,4-diamino butane | 25.9 | 562.30 | 562.65 |
| 194 | 175 | Diethylenetriamine | 4.1 | 577.31 | 577.67 |
| 195 | 175 | N,N'-Bis(3- | 8.7 | 662.41 | 662.82 |

TABLE 2-continued

| Compound Number | Resin Used | Amine Used | Yield in mg | MS found (M + H⁺) | MS calculated (M + H⁺) |
|---|---|---|---|---|---|
| | | aminopropyl)-1,3-propanediamine | | | |
| 191 | 176 | Methyl amine | 17.5 | 541.25 | 541.59 |
| 196 | 176 | 1,4-diamino butane | 26.1 | 598.31 | 598.69 |
| 197 | 176 | Diethylenetriamine | 8.5 | 613.32 | 613.70 |
| 198 | 176 | Ethylene diamine | 27.9 | 570.28 | 570.63 |
| 199 | 176 | Tris(2-aminoethyl)amine | 13.0 | 620.37 | 620.74 |
| 200 | 175 | Tris(2-aminoethyl)amine | 24.4 | 656.36 | 656.77 |

Example 110

Exemplary Synthesis Procedure for compound 201 (Scheme 9)

0.05 mM resin 175 was washed three times with ca. 5 mL DMF and three times with ca. 5 mL dichloromethane. The swelled resin was then washed for 1 minute with a mixture of 25% trifluoroacetic acid/2% anisole in dichloromethane and after draining treated for another 20 minutes with the same mixture. After draining, the resin was washed two times with ca. 5 mL dichloromethane and two times with ca. 5 mL DMF to give unprotected 178. Dipeptide 202 (61.1 mg, 0.10 mmol), synthesized separately in solution, was dissolved in 2 mL DMF and mixed with 36.1 mg HBTU and 34.7 μL DIEA. After 5 min this mixture was added to resin and agitated for 2 hours to give resin-bound tripeptide 203. This resin was treated for 2 hours with 2 mL of neat ethylenediamine to give product 201. The resin was filtered off, the solution was evaporated in vacuo and the resulting oil was dissolved 500 μL anisol and 2 mL TFA. After 30 min stirring, this solution was evaporated in vacuo, dissolved in methanol and precipitated with diethyl ether. The resulting precipitate was spun down, the ether decanted and the product dried in vacuo. This crude product was HPLC-purified (Vydac 12 μm, C18 2.2×25 cm column, 0% to 80% aqueous acetonitrile gradient over 20 min, flow rate 20 mL/min) to give purified 201 (see table 3).

Compounds 204–210 were synthesized using the same synthesis procedure as above, but with the following modifications: Compounds 204, 205, 206, and 207 started their synthesis with resin 175, compounds 208, 209 and 210 used resin 176. The amines used, to cleave tripeptide precursors from the resins to form compounds 201 through 210 are listed in table 3 under "Amines Used." Ethylene diamine and butyl amine were used neat (2 mL), all other amines were used in solution: Methyl amine (2M in THF), octyl amine (1 mL dissolved in 1 mL tetrahydofuran), and 2-methylaminopyridine (1 mL dissolved in 1 mL tetrahydofuran).

TABLE 3

| Compound Number | Resin Used | Amine Used | Yield in mg | MS found (M + H⁺) | MS calculated (M + H⁺) |
|---|---|---|---|---|---|
| 204 | 175 | Methyl amine | 8.5 | 547.25 | 547.59 |
| 205 | 175 | butyl amine | 17.1 | 589.30 | 589.67 |
| 206 | 175 | Octylamine | 8.1 | 645.37 | 645.78 |
| 207 | 175 | Ethylene diamine | 12.6 | 576.28 | 576.63 |
| 208 | 176 | Octylamine | 20.0 | 681.36 | 681.81 |
| 209 | 176 | butyl amine | 10.4 | 625.31 | 625.70 |
| 210 | 176 | Ethylene diamine | 12 | 612.29 | 612.66 |
| 211 | 176 | 2-methyl aminopyridine | 4.8 | 660.29 | 660.71 |

Example 111

Exemplary Synthesis Procedure for compound 211 (Scheme 10)

1-Methyl-4-nitro-imidazole-2-carboxylic acid ethyl ester (4 g, 20 mmol) were put into a screw cap flask and overlayered with 20 mL ethylene diamine and then placed overnight into a 55° C. oven. The solvent was evaporated in vacuo and subsequently dried under high vacuum to give 212.

212 was dissolved in 100 mL DMF and 6.55 g di-tert-butyl dicarbonate were added portionwise to the solution. After 1 hr stirring, the reaction was concentrated to 50 mL and separated between chloroform (150 mL) and 0.5 M sodium bicarbonate (150 mL). The organic layer was washed twice with 0.1M sulfuric acid, twice with water, dried over anhydrous sodium sulfate to give a yellow oil that later solidified. Recrystallisation with hot toluene gave 3.51 g (56% overall yield) of 213. $^1$-NMR (DMSO-$d_6$) 8.74 (tr, 1H, $\delta$=5.9, NH), 8.54 (s, 1H, imidazole C—H), 6.87 (tr, 1H, $\delta$=5.2, NH), 3.99 (s, 3H, Me), 3.23–3.28 (m, 2H, CH$_2$), 3.04 (q, 2H, $\delta$=5.9, CH$_2$), 1.35 (s, 9H, tBu); m.p. 138–139° C.

213 (3.12 g, 10 mmol) was dissolved under heating in 100 mL ethyl acetate. Methanol (20 mL), followed by 1 g of 5% palladium on carbon were added, and the hydrogenation was started in a Parr shaker at 37 psi. After 30 min. the pressure stabilized and the reaction was stopped. The catalyst was filtered off and the solvent was evaporated in vacuo. Drying under high vacuum gave a yellow/brown oil 214.

214 was dissolved in 15 mL DMF, 3.59 g (9 mmol) Pfp-ester SL40, which was previously synthesized in solution, was added and the reaction flask put into a 55° C. oven. After an overnight reaction the TLC indicated an incomplete reaction. SL38 (0.7 g) were hydrogenated as described above and its reaction product (214) was dissolved in 2 mL DMF and added to the solution. After continuing the reaction for another day at 55° C. the reaction was evaporated and the resulting brown oil purified via silica gel colomn cromatography. Increasing the gradient slowly from 9:1 to 1:1 tolene/ethyl acetate 320 mg (8%) of product 215 were obtained; $^1$-NMR (DMSO-$d_6$) 12.12 (s, 1H, NH), 10.61 (s, 1H, NH), 8.38 (s, 1H, indole C4—H), 7.97 (tr, 1H, NH, $\delta$=5.4), 7.89 (d, 1H, indole C6—H, $\delta$=8.6), 7.55 (s, 1H, imidazole C5—H), 7.48 (d, 1H, indole C7—H, $\delta$=8.7), 7.35 (s, 1H, indole C3—H), 6.89 (tr, 1H, NH, $\delta$=4.8), 4.34 (q, 2H, O—CH$_2$, $\delta$=6.9), 3.94 (s, 3H, CH$_3$), 3.31 (CH$_2$ signal under H$_2$O), 3.06 (q, 2H, CH$_2$, $\delta$=6.0), 1.348 (m, 12 H, tert-Bu, CH$_3$) ESI-MS: mass calculated (M+H⁺) 499.23, found 499.22.

215 (300 mg) were dissolved in 4 mL of methanol and heated to 60° C. 1.2 mL of 1N aqueous sodium hydroxide solution were added and the reaction was stirred at 60° C. for three hours. The reaction mixture was subsequently evaporated and redissolved in 5 mL of water. Acidification with 1 N aqueous hydrochloride to pH$_3$ precipitated the product, which was spun down. Four washings with water (30 mL each) brought the pH to 4.5. The resulting crystals were lyophilized and dried under high vacuum over $P_2O_5$ to give 248.9 mg (88%) of 216.

0.05 mM resin 176 was washed three times with ca. 5 mL DMF and three times with ca. 5 mL dichloromethane. The swelled resin was then washed for 1 minute with a mixture of 25% trifluoroacetic acid/2% anisole in dichloromethane and after draining treated for another 20 minutes with the same mixture. After draining, the resin was washed two times with ca. 5 mL dichloromethane and two times with ca. 5 mL DMF to give unprotected 178. Dipeptide 216 (61.1 mg, 0.10 mmol), synthesized as described above, was dissolved in 2 mL DMF and mixed with 36.1 mg HBTU and 34.7 μL DIEA. After 5 min this mixture was added to resin and agitated for 2 hours to give resin-bound tripeptide 217. This resin was treated for 2 hours with 2 mL of neat ethylenediamine. The resin was filtered off, the solution was evaporated in vacuo and the resulting oil was dissolved 500 μL anisol and 2 mL TFA. After 30 min stirring, this solution was evaporated in vacuo, and stirred for 2 hours with 0.5 mM N,N'-Bis(tert-butoxycarbonyl)-1H-pyrazole-1-carboxamidine dissolved in 2 mL DMF. The solution was evaporated in vacuo and the resulting oil was dissolved 500 μL anisol and 2 mL TFA. After 30 min stirring, this solution was evaporated in vacuo, dissolved in methanol and precipitated with diethyl ether. The resulting precipitate was spun down, the ether decanted and the product dried in vacuo. This crude product was HPLC-purified (Vydac 12 μm, C18 2.2×25 cm column, 0% to 80% aqueous acetonitrile gradient over 20 min, flow rate 20 mL/min) to give purified 211 (see table 4).

TABLE 4

| Compound Number | Resin Used | Amine Used | Yield in mg | MS found $(M + 2H^+)/2$ | MS calculated $(M + 2H^+)/2$ |
|---|---|---|---|---|---|
| 218 | 175 | ethylene diamine | 19.1 | 310.16 | 310.34 |
| 211 | 176 | ethylene diamine | 22.1 | 328.16 | 328.35 |

Example 112

Exemplary Synthesis Procedure for compound 219 (Scheme 11)

2,2-Bis(azidomethyl)-1,3-propanediol was synthesized from 2,2-Bis(bromomethyl)-1,3-propanediol in two steps, similarly to a procedure published previously (J. Med. Chem. 1989, 32, 2015–2020).

2,2-Bis(bromomethyl)-1,3-propanediol (3 g, 11.453 mmol) was stirred with 3 g (4 eq.) of sodium azide in 100 mL DMF at 120° C. for 2 days. The reaction was cooled to room temperature, filtered, evaporated to ca 10 mL. The residue was taken up in 100 mL dichloromethane, filtered and again evaporated. The residue was checked by NMR, which contained only DMF and 2,2-bis(azidomethyl)-1,3-propanediol. product was not further evaporated, but used in the next step. $^1$-NMR (DMSO-d6) 4.73 (tr, 2H, OH), 3.28 (s, 4H, 2*$CH_2$), 3.25 (d, 4H, 4.1 Hz); $^{13}$C-NMR (DMSO-$d_6$) 60.43, 51.80, 46.20. 2,2-Bis(azidomethyl)-1,3-propanediol was dissolved in 20 mL ethanol, cooled to 0° C. and 500 mg of 5% Pd/$CaCO_3$ were added. After bubbling Ar through the mixture for 15 min, the mixture was hydrogenated for 6 hr by bubbling $H_2$ through the suspension. The brown suspension turned black after 1–2 hours. Filtration, evaporation and drying yielded greasy 1.5 g of crystals. The crude product (2,2-bis(aminomethyl)-1,3-propanediol was used without further purification. $^1$-NMR (DMSO-$d_6$) 4.22 (s, 4H, 2*$CH_2$), 2.69 (br s, 6H, 2*OH, 2*$NH_2$), 2.47 (s, 4H, 2*$CH_2$); $^{13}$C-NMR (DMSO-$d_6$) 59.41, 39.57, 39.19; ESI-MS:: mass calculated (M+H$^+$) 135.11, found 135.12.

220 was synthesized from 221 in three steps. 221 (6g, 25.7 mmol) was suspended in 125 mL methanol and heated to 55° C. 3N aq. Sodium hydroxide solution was added, whereupon all of the starting material dissolved. After stirring for 5 hours at 55° C., the solution was acidified to pH 2, and filtered. The filtrate was washed with water (50 mL) and subsequently dried over phosphorus pentoxide to give indole-2,5-dicarboxylic acid 222 in quantitative yield. $^1$-NMR (DMSO-$d_6$): 12.06 (s, 1H, NH), 8.34 (s, 1H, CH), 7.82 (d, 1H, CH, δ=8.8 Hz), 7.47 (d, 1H, CH, δ=8.8 Hz), 7.23 (s, 1H, CH); m.p. 314–315° C.

Indole-2,5-dicarboxylic acid (222) (3 g, 12.86 mmol) was dissolved in 40 mL DMF. Diisopropylethylamine (5.37 mL, 2.4 eq) and 5.3 mL (2.4 eq) of pentafluorophenol trifluoro acetate were added to the reaction mixture. The reaction mixture was stirred overnight, evaporated, and separated between 150 mL ethyl acetate and 150 mL satured aq. sodium bicarbonate solution. The aqueous layer was extracted two more times with ethyl acetate (150 mL each); the organic layers were combined and dried over anhydrous sodium sulfate. The crude material was loaded on a silica gel-filled Büchner funnel and the product was eluted with 50% hexane/toluene mixture. 2.13 g (30.8%) of product 223 was obtained.

5-Nitro indole-2-carboxylic acid ethyl ester (654 mg, 2.79 mmol) was hydrogenated using 5% Pd/C (0.5 g) as a catalyst at 30 psi pressure for 30 min. Filtration through a frit to remove the catalyst, evaporation in vacuo and drying under high vacuum yielded free amine (224). It was immediately dissolved in 3 mL DMF and 500 mg 223 were added. The reaction was kept at 55° C. overnight and then evaporated. The crude material was recrystallized from hot ethanol to give 273 mg (50.8%) of product (220) after evaporation and drying. $^1$H-NMR (DMSO-$d_6$): 11.98 (s, 1H, NH—indole), 11.86 (s, 1H, NH—indole), 11.81 (s, 1H, NH-indole), 10.25 (s, 1H, CONH), 10.11 (s, 1H, CONH), 8.39 (s, 1H, CH), 8.15 (s, 1H, CH), 7.86 (dd, 1H, CH, δ=9.2, δ=1.4), 7.53–7.62 (m, 4H, 4*CH), 7.43 (tr, 2H, δ=9.1), 7.15 (d, 2H, 2*CH, δ=7.9), 4.33 (q, 4H, 2*$CH_2$, δ=7.0), 1.34 (tr, 6H, 2*$CH_3$, δ=7.0).

30 mg of tripeptide (220) and 150 mg of diamine ((2,2-bis(aminomethyl)-1,3-propanediol) were dissolved in 1 mL DMF. The reaction was stirred for 3 days at room temperature and then 4 days at 55° C. Evaporation was followed by HPLC-purification (Vydac 12 μm, C18 2.2×25 cm column, 30% to 80% aqueous acetonitrile gradient over 20 min, flow rate 20 mL/min) to give purified product. After lyophilisation, the product was dissolved in ice-cold methanol, acidified with 200 μL 4 N HCl/dioxane and then precipitated with diethyl ether. The product was centrifuged, the ether decanted. The final product was dried in vacuo to give purified 219. In the synthesis of 225 30 mg of tripeptide (220) were dissolved in 500 μL neat 2,2-Dimethyl-1,3-propanediamine. The same reaction conditions and purification procedure were chosen as for 219.

TABLE 5

| Compound Number | Amine Used | Yield in mg | MS found (M + H⁺) | MS calculated (M + H⁺) |
|---|---|---|---|---|
| 219 | (2,2-bis(aminomethyl)-1,3-propanediol | 1.7 | 754.36 | 754.36 |
| 225 | (2,2-dimethyl)-1,3-propane diamine | 4.7 | 690.35 | 690.35 |

Example 113

Exemplary Synthesis Procedure for compound 226 (Scheme 12)

227 (30 mg) was dissolved in 2 mL DMF and brought to −20° C. in an acetone/$CO_2$ bath. Diisopropyl ethylamine (19 µL, 2.2 eq) and 4-nitrobenzylchloroformate (24 mg) were added. After stirring at −20° C. for 30 min., the reaction was stirred at room temperature overnight. Evaporation was followed by HPLC-purification (Vydac 12 µm, C18 2.2×25 cm column, 0% to 100% aqueous acetonitrile gradient over 20 min, flow rate 20 mL/min) to give purified compound. After lyophilisation, the product was dissolved in ice-cold methanol, acidified with 200 µL 4 N HCl/dioxane and then precipitated with diethyl ether. The product was centrifuged, the ether decanted. The final product was dried in vacuo to give purified 226 (see table 6). The same synthesis was performed with 4-methoxyphenyl chloroformate to give 228.

TABLE 6

| Compound Number | Chloroformate used: | Yield in mg | MS found (MH⁺) | MS calculated (MH⁺) |
|---|---|---|---|---|
| 228 | 4-nitrobenzyl chloroformate | 7.6 | 785.40 | 785.27 |
| 226 | 4-methoxyphenyl chloroformate | 9.8 | 756.41 | 756.28 |

Example 114

Synthesis Procedure for compound 229 and 230 (Scheme 13)

Benzimidazole 231(349.5 mg, 1.2 mmol) were dissolved in pure TFA(5 mL) and left standing at room temperature for 30 min. Toluene was subsequently added and the solution evaporated in vacuo. This procedure was repeated twice. The resulting amine 232 was dried under high vacuum. 232 was then dissolved in 5 mL DMF and 223 (214.9 mg, 0.4 mmol) as well as 6 eq. of diisopropylethylamine (418 µL) were added. This mixture was stirred for 1 week at room temperature. The reaction was monitored via HPLC purified (Vydac 12 µm, C18 2.2×25 cm column, 0% to 100% aqueous acetonitrile gradient over 20 min, flow rate 20 mL/min). Disappearance of a peak at 100% acetonitrile (corresponding to 223) and appearance of a major peak at ca. 75% acetonitrile. The peak was very broad and consisted predominantly of dipeptide 233 as well as a minor amount of 234. The substitution for 233 was assumed to be at the C-2 carboxy group, in accordance with several previous studies, which showed preferred substitution at this site. 30 mg of the mixture 233 and 234 were dissolved in 5 mL ethylenediamine and stirred for 1.5 days. The mixture was subsequently evaporated and HPLC-purified. Tripeptide was isolated and converted to the HCl salt, yielding 2.3 mg of final product (229).

235 (40 mg, 115 µmol) was dissolved in methanol/ethyl acetate and hydrogenated for 30 min in a Parr Shaker at ca. 30 psi. The catalyst was filtered off, the solvent evaporated and the resulting free amine (SL61) dried under high vacuum. 236 was dissolved in 3 mL DMF and 30 mg (55.1 µmol) SL57 and 20 µL (115 µmol) disopropylethyl amine were added. The reaction was stirred for 1½ days and then evaporated to give crude 237. It was immediately dissolved in 200 µL anisol and 1800 µL TFA, left standing for 300 min, precipitated with ether, centrifuged, the ether decanted and subsequently dried. The compound was purified via preparative HPLC, lyophilized, dissolved in ice-cold methanol, acidified with 4 M HCl/dioxane, precipitated with ether, centrifuged, the ether was decanted and the product 230 dried in vacuo.

TABLE 7

| Compound Number | Amine Used: | Yield in mg | MS found (MH⁺) | MS calculated (MH⁺) |
|---|---|---|---|---|
| 229 | EDA | 2.3 | 608.32 | 608.25 |
| 230 | — | 5.1 | 579.17 | 579.21 |

Example 115

Synthesis of pyridine-2,5-dicarboxylic acid bis-{[5-(2-carbamimidoyl-ethylcarbamoyl)-1-propyl-1H-pyrrol-3-yl]-amide} 231

Step A: 1-propyl-4-nitro-1H-pyrrole-2-carboxylic acid ethyl ester 232.

4-Nitro-1H-pyrrole-2-carboxylic acid ethyl ester (5 g) was dissolved in 50 ml of dry EtOH, 50 ml of 1M sodium ethylate was added followed with 10 ml of $CH_3I$. The reaction mixture was heated at 80° C. for 4 hours, cooled down to room temperature and distributed between water and chloroform. The organic phase was washed with water, dried with sodium sulfate and evaporated. The residue was recrystallized from hexane to yield 4.72 g (77%) of 1-propyl-4-nitro-1H-pyrrole-2-carboxylic acid ethyl ester 232. $H^1$-NMR (DMSO-d6): 0.79 (t, 3H, $CH_3$), 1.25 (t, 3H, $CH_3$), 1.68 (m, 2H, $CH_2$), 4.17–4.28 (m, 4H, $2CH_2$), 7.23 and 8.24 (d, 1H, pyrrole)

Step B: Synthesis of 1-(propyl)-4-nitro-1H-pyrrole-2-carboxylic acid (2-cyano-ethyl)-amide 233.

Compound 232 (5 g) was suspended in 30 ml of methanol, 2M NaOH (10 ml) was added, and the mixture was stirred at 50° C. for 2 hours. The clear solution was diluted with water (50 ml) and 1N HCl was added dropwise to get $pH_{2.5}$. The white residue was filtered, washed with water and dried to get 4.6 g (95%) of the acid 234. ES MS: 220.47 (M+Na—H⁺). The acid 234 was suspended in $SOCl_2$ (20 ml) and the mixture was refluxed for 4 hours until clear solution was obtained. The reaction mixture was evaporated and dried by co-evaporation with toluene (10 ml×3). The obtained chloroanhydride 235 was used without purification. Anhydride 235 was dissolved in toluene (10 ml) and 3-aminopropionitrille (3.9 ml, 54.3 mmol) was added. The mixture was kept for 1 hour at ambient temperature and evaporated. The white precipitate was suspended in 0.1 N HCl, filtered, washed with water and dried. Recrystallized from methanol yielded 4.4 g (81%) of 233.

ES MS: 251.87 (M+H+). H¹-NMR (DMSO-d6): 0.73–0.79 (m, 3H, CH$_3$), 1.63–1.70 (m, 2H, CH$_2$-propyl), 2.84–2.89 (m, 2H, CH$_2$—CN), 3.65–3.42 (m, 2H, CH$_2$—NH), 4.27–4.32 (m, 2H, CH$_2$—N), 7.43 and 8.15 (d, 1H, pyrrole), 8.83 (bt, 1H, NH).

Step C: Synthesis of 1-propyl-4-nitro-1H-pyrrole-2-carboxylic acid (2-carbamimidoyl-ethyl)-amidine 236.

The solution of 1-(propyl)-4-nitro-1H-pyrrole-2-carboxylic acid (2-cyano-ethyl)-amidine 233 (2.5 g, 10 mmol) in 50 ml of dry ethanol was cooled to 0–5° C. and saturated with HCl gas. The mixture was sealed and refrigerated for 20 hours. The mixture was allowed to warm to room temperature and ethanol was evaporated. The solid was dissolved in 50 ml of dry ethanol and saturated with ammonia gas. The sealed mixture was kept overnight at room temperature and evaporated. The solid was dissolved in 10 ml of methanol, and ether was added to precipitate 2.4 g (94%) of the target product 236 as a white solid. ES MS: 268.92 (M+H+). H¹-NMR (DMSO-d6): 0.79 (t, 3H, CH$_3$), 1.64–1.71 (m, 2H, CH$_2$-propyl), 2.62–2.66 (m, 2H, CH$_2$—CN), 3.49–3.55 (m, 2H, CH—NH), 4.28–4.33 (m, 2H, CH$_2$—N), 7.54 and 8.15 (d, 1H, pyrrole), 8.83 (t, 1H, NH).

Step D: Synthesis of pyridine-2,5-dicarboxylic acid bis-{[5-(2-carbamimidoyl-ethylcarbamoyl)-1-propyl-1H-pyrrol-3-yl]-amide} 231.

To stirred solution of 1-propyl-4-nitro-1H-pyrrole-2-carboxylic acid (2-carbamimidoyl-ethyl)-amidine 236 (70 mg, 0.15 mmol) in methanol (20 ml) was added 10% Pd/C (Degussa type, Aldrich) (0.1 g). The flask was evacuated and then flushed 3 times with hydrogen and finally filled with hydrogen at 25–30 psi. The resultant suspension was stirred vigorously at 23° C. for 45 min. The suspended material was filtered, the filtrate was evaporated to dryness. The resulted 1-propyl-4-amino-1H-pyrrole-2-carboxylic acid (2-carbamimidoyl-ethyl)-amidine 237 was used for the next step without purification. The solution of freshly prepared 237 in 3 ml of dry DMF was added to pyridine-2,5-dicarboxylic acid dipentafluorophenyl ester (25 mg, 0.07 mmol), the reaction mixture was stirred for 15 hours at 55° C., cooled down, and purified by HPLC (Vydac 12 µm C$_{18}$ 2.2×25 cm column, 10–70% acetonitrile gradient over 40 min, flow 10 mL/min) to give pyridine-2,5-dicarboxylic acid bis-{[5-(2-carbamimidoyl-ethylcarbamoyl)-1-propyl-1H-pyrrol-3-yl]-amide} 231 as a bis-trifluoroacetate salt: 33 mg (57%). ES MS: 606.71 (M+H+). The bis-trifluoroacetate salt of 231 was dissolved in 2 ml of methanol saturated with HCl, 35 ml of diethyl ether was added, the precipitate of 231 as HCl salt was separated and dried.

Example 116

Synthesis of N,N'-Bis-[5-(2-carbamimidoyl-ethylcarbamoyl)-1-propyl-1H-pyrrol-3-yl]-isophthalamide 238.

Compound 231 was synthesized as described for compound 231 above. Yield 52% of compound 231. ES MS: 605.72 (M+H+).

Example 117

N,N'-Bis-[5-(2-carbamimidoyl-ethylcarbamoyl)-1-(3-methyl-butyl)-1H-pyrrol-3-yl]-terephthalamide 239

Step A: Synthesis of 1-(3-methyl-butyl)-4-nitro-1H-pyrrole-2-carboxylic acid ethyl ester 240.

Compound 240 was synthesized as described in example 1, step A, using 1-bromo-3-methyl-butane as an alkylating agent. The yield is 6.5 g (94%). H¹-NMR (DMSO-d6): 0.87 (d, 6H, CH$_3$), 1.26 (t, 3H, CH$_3$), 1.49–1.62 (m, 3H, CH & CH$_2$), 1.68 (m, 2H, CH$_2$), 4.23 (q, 2H, CH$_2$), 4.33 (t, 2H, CH$_2$), 7.28 and 8.29 (d, 1H, pyrrole).

Step B: Synthesis of 1-(3-methyl-butyl)-4-nitro-1H:-pyrrole-2-carboxylic acid (2-cyano-ethyl)-amide 241.

Compound 241 was synthesized from ethyl carboxylate 240 as described in Example 115, step B. The yield is 5.1 g (83%). ES MS: 277.34 (M+H+). H¹-NMR (DMSO-d6): 0.83–0.86 (m, 6H, CH$_3$), 1.40–1.51 (m, 1H, CH), 1.51–1.61 (m, 2H, CH$_2$—CH), 2.68–2.72 (m, 2H, CH$_2$—CN), 3.35–3.42 (m, 2H, C$_2$—NH), 4.33–4.37 (m, 2H, CH$_2$—N), 7.38 and 8.15 (d, 1H, pyrrole), 8.56 (bt, 1H, NH).

Step C: Synthesis of 1-(3-methyl-butyl)-4-nitro-1H-pyrrole-2-carboxylic acid (2-cyano-ethyl)-amidine 242.

Compound 242 was synthesized from cyanoethylamide 241 as described in Example 115, step C in 10 mmol scale. The yield is 2.5 g (86%). ES MS: 295.34 (M+H+). H¹-NMR (DMSO-d6): 0.88–0.86 (d, 6H, CH$_3$), 1.43–1.61 (m, 3H, CH & CH$_2$—CH), 2.61–2.65 (m, 2H, CH$_2$—CN), 3.49–3.55 (m, 2H, CH$_2$—NH), 4.33–4.38 (m, 2H, CH$_2$—N), 7.51 and 8.18 (d, 1H, pyrrole), 8.73 (t, 1H, NH).

Step D: Synthesis of N,N'-Bis-[5-(2-carbamimidoyl-ethylcarbamoyl)-1-(3-methyl-butyl)-1H-pyrrol-3-yl]-terephthalamide 239

Compound 242 was condensed with dipentafluorophenyl ester of terephtalic acid as described in example 115, step D. Yield 47% of compound 239. ES MS: 661.84 (M+H+).

Example 118

Synthesis of Hexanedioic acid bis-{[5-(2-carbamimidoyl-ethylcarbamoyl)-1-(3-methyl-butyl)-1H-pyrrol-3-yl]-amide} 243

Compound 243 was synthesized as described for compound 239 above (Example 117). Yield 52% of compound 243. ES MS: 640.82 (M+H+).

Example 119

Cyclohexane-1,4-dicarboxylic acid bis-{[5-(2-carbamimidoyl-ethylcarbamoyl)-1-(3-methyl-butyl)-1H-pyrrol-3-yl]-amide} 244

Compound 244 was synthesized as described for compound 239 above (Example 117). Yield 48% of compound 244. ES MS: 667.87 (M+H+).

Example 120

Biphenyl-4,4'-dicarboxylic acid bis-{[5-(2-carbamimidoyl-ethylcarbamoyl)-1-(3-methyl-butyl)-1H-pyrrol-3-yl]-amide} 245

Compound 245 was synthesized as described for compound 239 above (example 117). Yield 56% of compound 245. ES MS: 737.98. (M+H+).

Example 121

Thiophene-2,5-dicarboxylic acid bis-{[5-(2-carbamimidoyl-ethylcarbamoyl)-1-(3-methyl-butyl)-1H-pyrrol-3-yl]-amide} 246

Compound 246 was synthesized as described for compound 239 above (example 117). Yield 42% of compound 246. ES MS: 666.81. (M+H+).

Example 122

N,N-Bis-[5-(2-carbamimidoyl-ethylcarbamoyl)-1-cyclopropylmethyl-1H-pyrrol-3-yl]-terephthalamide 247

Step A: Synthesis of 1-cyclopropylmethyl-4-nitro-1H-pyrrole-2-carboxylic acid ethyl ester 248.

Compound 248 was synthesized as described in example 1, step A, using bromomethyl-cyclopropane as an alkylating agent. The yield is 4.8 g (74%). H$^1$-NMR (DMSO-d6): 0.37–0.42 & 0.65–0.72 (m, 2H, CH$_2$), 1.22–1.28 (m, 1H, CH), 1.37 (t, 3H, CH$_3$), 4.23 (d, 2H, CH$_2$), 4.32 (q, 2H, CH$_2$), 7.44 and 7.81 (d, 1H, pyrrole).

Step B: Synthesis of 1-(cyclopropylmethyl)-4-nitro-1H-pyrrole-2-carboxylic acid (2-cyanoethyl)-amide 249.

Compound 249 was synthesized from ethyl carboxylate 248 as described in Example 115, step B. The yield is 4.3 g (78%). ES MS: 263.97 (M+H$^+$). H$^1$-NMR (DMSO-d6): 0.02–0.04 & 0.09–0.12 (m, 2H, CH$_2$), 0.89–1.00 (m, 1H, CH), 2.37–2.41(t, 2H, CH—CN), 3.06–3.11 (dd, 2H, C$_2$—NH), 3.86–3.88 (d, 2H, CH—N), 7.09 and 7.87 (d, 1H, pyrrole), 8.45 (t, 1H, NH).

Step C: Synthesis of 1-(cyclopropylmethyl)-4-nitro-1H-pyrrole-2-carboxylic acid (2-cyanoethyl)-amidine 250.

Compound 250 was synthesized from cyanoethylamide 249 as described in Example 115, step C in 10 mmol scale. The yield is 2.1 g (75%). ES MS: 280.01 (M+H$^+$).

Step D: N,N'-Bis-[5-(2-carbamimidoyl-ethylcarbamoyl)-1-cyclopropylmethyl-1H-pyrrol-3-yl]-terephthalamide 247.

Compound 247 was synthesized as described for compound 231 in Example 115, step D. ES MS: 628.74 (M+H$^+$).

Example 123

Pyridine-2,5-dicarboxylic acid bis-{[5-(2-carbamimidoyl-ethylcarbamoyl)-1-cyclopropylmethyl-1H-pyrrol-3-yl]-amide} 251

Compound 251 was synthesized as described for compound 247 above (Example 122). Yield 56% of compound 251. ES MS: 630.73. (M+H$^+$).

Example 124

N$^1$,N$^1$-Bis-[5-(2-carbamimidoyl-ethylcarbamoyl)-1-cyclopropylmethyl-1H-pyrrol-3-yl]-2-nitro-terephthalamide 252

Compound 252 was synthesized as described for compound 247 above (Example 122). Yield 54% of compound 252. ES MS: 674.73. (M+H$^+$).

Example 125

Thiophene-2,5-dicarboxylic acid bis-{[5-(2-carbamimidoyl-ethylcarbamoyl)-1-cyclopropylmethyl-1H-pyrrol-3-yl]-amide} 253

Compound 253 was synthesized as described for compound 247 above (Example 122). Yield 41% of compound 253. ES MS: 679.81. (M+H$^+$).

Example 126

Pyrazine-2,5-dicarboxylic acid bis-{[5-(2-carbamimidoyl-ethylcarbamoyl)-1-cyclopropylmethyl-1H-pyrrol-3-yl]-amide≡ 254

Compound 254 was synthesized as described for compound 247 above (Example 122). Yield 48% of compound 254. ES MS: 630.71. (M+H$^+$).

Example 127

Cyclohexa-1,3-diene-1,4-dicarboxylic acid bis-{[5-(2-carbamimidoyl-ethylcarbamoyl)-1-(3-methyl-butyl)-1H-pyrrol-3-yl]-amide} 255

Compound 255 was synthesized as described for compound 239 above (Example 117). Yield 48% of compound 255. ES MS: 663.85. (M+H$^+$).

Example 128

1H-Pyrazole-3,5-dicarboxylic acid bis-([5-(2-carbamimidoyl-ethylcarbamoyl)-1-cyclopropylmethyl-1H-pyrrol-3-yl]-amide} 256

Compound 256 was synthesized as described for compound 247 above (Example 122). Yield 48% of compound 256. ES MS: 618.76. (M+H$^+$).

Example 129

Cyclopropane-1,1-dicarboxylic acid bis-{[5-(2-carbamimidoyl-ethylcarbamoyl)-1-(3-methyl-butyl)-1H-pyrrol-3-yl]-amide} D21

Compound 257 was synthesized as described for compound 239 above (Example 117). Yield 51% of compound 257. ES MS: 625.79. (M+H$^+$).

Example 130

N,N'-Bis-{1-(3-methyl-butyl)5-[2-(N-methylcarbamimidoyl)-ethylcarbamoyl]-1H-pyrrol-3-yl]-terephthalamide 258

Step A: Synthesis of 1-(3-Methyl-butyl)-4-nitro-1H-pyrrole-2-carboxylic acid [2-(N-methylcarbamimidoyl)-ethyl]-amide 259.

The solution of 1-(3-methyl-butyl)-4-nitro-1H-pyrrole-2-carboxylic acid (2-cyanoethyl)-amidine 242 (0.5 g) in 50 ml of dry ethanol was cooled to 0–5° C. and saturated with HCl gas. The mixture was sealed and refrigerated for 20 hours. The mixture was allowed to warm to room temperature and ethanol was evaporated. The solid was dissolved in 10 ml of dry ethanol and 1 M solution of methylamine (3 ml) in methanol was added. The sealed mixture was kept overnight at 15° C. and evaporated. The solid was dissolved in 10 ml of methanol, and ether was added to precipitate 2.4 g (94%) of 1-(3-Methyl-butyl)-4-nitro-1H-pyrrole-2-carboxylic acid [2-(N-methylcarbamimidoyl)-ethyl]-amide 259 as a white solid. ES MS: 310.94 (M+H$^+$). H$^1$-NMR (DMSO-d6): 0.86–0.88 (d, 6H, CH$_3$-isopentyl), 1.43–1.61 (m, 3H, CH & CH$_2$—CH), 2.60–2.65 (t, 2H, CH$_2$CH)-amidine), 3,37 (s, 3H, C$_3$—NH), 3.49–3.55 (m, 2H, CH$_2$—NHCO), 4.33–4.38 (t, 2H, CH$_2$—N), 7.51 and 8.18 (d, 1H, pyrrole), 8.73 (t, 1H, NHCO).

Step B: N,N'-Bis-[5-(2-carbamimidoyl-ethylcarbamoyl)-1-(3-methyl-butyl)-1H-pyrrol-3-yl]-terephthalamide 258

Compound 258 was synthesized from 259 as described in Example 115, step D. ES MS: 689.88. (M+H$^+$).

Example 131

Pyridine-2,5-dicarboxylic acid bis-{[5-[2-(N-ethylcarbamimidoyl)-ethylcarbamoyl]-1-(3-methyl-butyl)-1H-pyrrol-3-yl]-amide} 260

Step A: Synthesis of 1-(3-Methyl-butyl)-4-nitro-1H-pyrrole-2-carboxylic acid [2-(N-ethylcarbamimidoyl)-ethyl]-amide 261.

Compound 261 was synthesized from cyanoethylamide 242 as described in Example 130, step A, using ethylamine (3 ml). ES MS: 324.79 (M+H$^+$). H$^1$-NMR (DMSO-d6): 0.88–0.86 (d, 6H, CH$_3$-isopentyl), 1.07–1.12 (t, 3H, CH$_3$-ethyl), 1.43–1.61 (m, 3H, CH & CH$_2$—CH), 2.52–2.56 (t, 2H, CH$_2$CH$_2$-amidine), 3.12–3.21 (m, 2H, CH$_2$-ethyl), 3.49–3.55 (m, 2H, CH$_2$CH$_2$-amidine), 4.33–4.38 (t, 2H, CH$_2$—N), 7.39 and 8.20 (d, 1H, pyrrole), 8.54–8.60 (NH-amidine), 9.38 (t, 1H, NHCO).

Step B: Pyridine-2,5-dicarboxylic acid bis-{[5-[2-(N-ethylcarbamimidoyl)-ethylcarbamoyl]-1-(3-methyl-butyl)-1H-pyrrol-3-yl]-amide} 262

Compound 262 was synthesized as described in Example 115, step D. Yield 40% of compound 262. ES MS: 718.92. (M+H$^+$).

Example 132

N,N'Bis-[5-[2-(N-isopropyl-carbamimidoyl)-ethylcarbamoyl]-1-(3-methyl-butyl)-1H-pyrrol-3-yl]-terephthalamide Step A: Synthesis of 1-(3-Methyl-butyl)-4-nitro-1H-pyrrole-2-carboxylic acid [2-(N-isopropylcarbamimidoyl)-ethyl]-amide 263.

Compound 263 was synthesized from cyanoethylamide 242 as described in Example 130, step A, using isopropylamine (3 ml). ES MS: 338.67 (M+H$^+$). H$^1$-NMR (DMSO-d6): 0.85–0.87 (d, 6H, CH$_3$-isopentyl), 1.09–1.11 (t, 3H, CH$_3$-isopropyl), 1.43–1.61 (m, 3H, CH & CH$_2$—CH), 2.59–2.64 (t, 2H, CH$_2$CH$_2$-amidine), 3.50–3.55 (m, 2H, CH$_2$ CH-amidine), 3.73–3.80 (m, 1H, CH-isopropyl), 4.33–4.38 (t, 2H, CH$_2$—N), 7.55 and 8.18 (d, 1H, pyrrole), 8.70 (t, 1H, NHCO).

Step B: N,N'-Bis-[5-[2-(N-isopropyl-carbamimidoyl)-ethylcarbamoyl]-1-(3-methyl-butyl)-1H-pyrrol-3-yl]-terephthalamide 264

Compound 264 was synthesized as described in Example 115, step D. ES MS: 745.98. (M+H$^+$).

Example 133

Thiophene-2,5-dicarboxylic acid bis-[(1-(3-methyl-butyl)-5-{2-[N-(3-methyl-butyl)-carbamimidoyl]-ethylcarbamoyl}-1H-pyrrol-3-yl)-amide] 265

Step A: Synthesis of 1-(3-Methyl-butyl)-4-nitro-1H-pyrrole-2-carboxylic acid {2-[N-(3-methyl-butyl)isopropylcarbamimidoyl]-ethyl}-amide 266.

Compound 266 was synthesized from cyanoethylamide 242 as described in Example 130, step A, using 3-methyl-butylamine (3 ml). ES MS: 365.27 (M+H$^+$). H$^1$-NMR (DMSO-d6): 0.79–0.81 (d, 6H, CH$_3$-isopentyl of pyrrole), 0.86–0.88 (d, 6H, CH$_3$-isopentyl of amidine), 1.31–1.60 (m, 6H, CH & CH$_2$—CH), 2.64–2.68 (t, 2H, CH$_2$CH$_2$-amidine), 3.12–3.17 (t, 2H, NH—CH$_2$ isopentyl of amidine), 3.50–3.55 (m, 2H, CH$_2$CH$_2$-amidine), 4.33–4.38 (t, 2H, CH$_2$—N), 7.55 and 8.18 (d, 1H, pyrrole), 8.72 (t, 1H, NHCO).

Step B: Thiophene-2,5-dicarboxylic acid bis-[(1-(3-methyl-butyl)-5-{2-[N-(3-methyl-butyl)-carbamimidoyl]-ethylcarbamoyl}-1H-pyrrol-3-yl)-amide]

Compound 265 was synthesized as described in Example 115, step D. Yield 54% of compound 265. ES MS: 808.12. (M+H$^+$).

Example 134

1H-Pyrazole-3,5-dicarboxylic acid bis-{[5-[2-(N-cyclopentylcarbamimidoyl)-ethylcarbamoyl]-1-(3-methyl-butyl)-1H-pyrrol-3-yl]-amide} 267

Step A: Synthesis of 1-(3-Methyl-butyl)-4-nitro-1H-pyrrole-2-carboxylic acid [2-(N-cyclopentylcarbamimidoyl)-ethyl]-amide 268

Compound 268 was synthesized from cyanoethylamide 242 as described in Example 115, step D, using cyclopentylamine (3 ml). ES MS: 364.37 (M+H$^+$). H$^1$-NMR (DMSO-d6): 0.85–0.87 (d, 6H, CH$_3$), 1.43–1.61 (m, 10H, CH & CH$_2$—CH of pyrrole and CH$_2$ of cyclppentyl), 1.82–1.88 (m, 2H, CH), 2.63–2.67 (t, 2H, CH$_2$ CH$_2$-amidine), 3.47–3.56 (m, 2H, CH$_2$CH$_2$-amidine), 4.33–4.38 (t, 2H, CH$_2$—N), 7.56 and 8.18 (d, 1H, pyrrole), 8.71 (t, 1H, NHCO).

Step B: 1H-Pyrazole-3,5-dicarboxylic acid bis-{[5-[2-(N-cyclopentylcarbamimidoyl)-ethylcarbamoyl]-1-(3-methyl-butyl)-1H-pyrrol-3-yl]-amide} 267

Compound 265 was synthesized as described in example 115, step D. Yield 54% of compound 267. ES MS: 788.03. (M+H$^+$).

Example 135

N,N'-Bis-[5-[2-(N,N'-dimethyl-carbamimidoyl)-ethylcarbamoyl]-1-(3-methyl-butyl)-1H-pyrrol-3-yl]-terephthalamide 269

Step A: Synthesis of 1-(3-Methyl-butyl)-4-nitro-1H-pyrrole-2-carboxylic acid [2-(N,N'-dimethylcarbamimidoyl)-ethyl]-amide 270.

The solution of 1-(3-methyl-butyl)-4-nitro-1H-pyrrole-2-carboxylic acid (2-cyano-ethyl)-amidine 242 (0.5 g) in 50 ml of dry ethanol was cooled to 0–5° C. and saturated with HCl gas. The mixture was sealed and refrigerated for 20 hours. The mixture was allowed to warm to room temperature and ethanol was evaporated. The solid was dissolved in 10 ml of dry ethanol and 1M solution of methylamine (6 ml) in methanol was added. The sealed mixture was kept overnight at 55° C. and evaporated. The solid was dissoved in 10 ml of methanol, and ether was added to precipitate 2.4 g (94%) of the target product as a white solid. ES MS: 324.74 (M+H$^+$). H$^1$-NMR (DMSO-d6): 0.85–0.87 (d, 6H, CH$_3$-isopentyl), 1.43–1.61 (m, 3H, CH & CH$_2$—CH), 2.76–2.79 (m, 5H, CH$_2$ CH$_9$-amidine and CH$_3$—NH), 2.96–2.98 (d, 3H, CH$_3$—NH), 3.46–3.55 (m, 2H, CH$_2$—NHCO), 4.34–4.39 (t, 2H, CH$_2$—N), 7.51 and 8.18 (d, 1H, pyrrole), 9.76 (t, 1H, NHCO).

Step B: N,N'-Bis-[5-[2-(N,N'-dimethyl-carbamimidoyl)-ethylcarbamoyl]-1-(3-methyl-butyl)-1H-pyrrol-3-yl]-terephthalamide 269

Compound 269 was synthesized as described in Example 115, step D. ES MS: 717.93 (M+H$^+$).

Example 136

Pyridine-2,5-dicarboxylic acid bis-{[5-[2-(N,N'-diethyl-carbamimidoyl)-ethylcarbamoyl]-1-(3-methyl-butyl)-1H-pyrrol-3-yl]-amide}271

Step A: Synthesis of 1-(3-Methyl-butyl)-4-nitro-1H-pyrrole-2-carboxylic acid [2-(N,N'-diethylcarbamimidoyl)-ethyl]-amide 272.

Compound 272 was synthesized from cyanoethylamide 242 as described above for compound 270 using ethylamine (3 ml). ES MS: 351.53. (M+H$^+$). H$_1$-NMR (DMSO-d6): 0.86–0.88 (d, 6H, CH$_3$-isopentyl), 1.07–1.17 (t, 6H, CH$_3$-ethyl), 1.42–1.60 (m, 3H, CH & CH$_2$—CH), 2.67–2.72 (t, 2H, CH$_2$ CH$_2$-amidine), 3.12–3.21 (m, 2H, CH$_2$-ethyl), 3.36–3.50 (m, 4H, CH$_2$—NHCO and CH$_2$-ethyl), 4.33–4.38 (t, 2H, CH$_3$—N), 7.39 and 8.20 (d, 1H, pyrrole), 8.63–8.71 (NH-amidine), 9.30 (t, 1H, NHCO).

Step B: Pyridine-2,5-dicarboxylic acid bis-{[5-[2-(N,N'-diethyl-carbamimidoyl)ethylcarbamoyl]-1-(3-methyl-butyl)-1H-pyrrol-3-yl]-amide} 271

Compound 271 was synthesized as described in Example 115, step D. Yield 51% of compound 271. ES MS: 775.03 (M+H$^+$).

Example 137

N,N'-Bis-{-(3-methyl-butyl)-5-[2-(1,4,5,6-tetrahydro-pyrimidin-2-yl)-ethylcarbamoyl]-1H-pyrrol-3-yl}-terephthalamide 273

Step A: Synthesis of 1-(3-Methyl-butyl)-4-nitro-1H-pyrrole-2-carboxylic acid [2-(1,4,5,6-tetrahydropyrimidin-2-yl)-ethyl]-amide 274.

Compound 274 was synthesized from cyanoethylamide 242 as described above for compound 270 using 1,3-propylamine (6 ml). ES MS: 364.37 (M+H$^+$). H$_1$-NMR (DMSO-d6): 0.85–0.87 (d, 6H, CH$_3$), 1.42–1.61 (m, 3H, CH & CH$_2$—CH of pyrrole), 1.79–1.84 (m, 2H, CH$_2$CH$_2$ CH$_2$), 2.55–2.60 (t, 2H, CH$_2$ CH$_2$-amidine), 3.25 (m, 4H, CH$_2$ CH$_2$ CH$_2$), 3.40–3.52 (m, 2H, CH$_2$—NHCO), 4.33–4.38 (t, 2H, CH$_2$-N), 7.48 and 8.18 (d, 1H, pyrrole), 8.15 and 9.78 (bs, 1H, NH-amidine), 8.89 (t, 1H, NHCO).

Step B: Synthesis of 1-(3-Methyl-butyl)-4-nitro-1H-pyrrole-2-carboxylic acid [2-(1,4,5,6-tetrahydropyrimidin-2-yl)-ethyl]-amide 273

Compound 273 was synthesized as described in Example 115, step D. ES MS: 741.96 (M+H$^+$).

Example 138

N,N'-Bis-[5-(2-amino-ethylcarbamoyl)-1-(3-methyl-butyl)-1H-pyrrol-3-yl]-terephthalamide 274

Step A: [2-({1-[1-(3-Methyl-butyl)-4-nitro-1H-pyrrol-2-yl]-methanoyl}-amino)-ethyl]-carbamic acid tert-butyl ester 275

Compound 240 (1.3 g, 5 mmol) was dissolved in diethylamine (20 ml). This solution was kept for 50 hours at 60° C. and evaporated. The residue was dissolved in DMF (20 ml) and diBoc-carbonate (2.18 g, 10 mmol) was added. The reaction was kept 1 h at ambient temperature and evaporated. The residue was dissolved in chloroform (30 ml), washed with 0.1 M HCl (10×2 ml), 5% NaHCO$_3$ (10×2 ml), water, dried over sodium sulfate, and evaporated. The crude compound D33 was crystallized from toluene/hexane (4:1 v/v) to give white crystalls. The yield is 69% (1.27 g). H$^1$-NMR (DMSO-d6): 0.85–0.87 (d, 6H, CH$_3$), 1.34 (s, 9H, Boc), 1.42–1.61 (m, 3H, CH & CH$_2$—CH of pyrrole), 3.03–3.08 and 3.18–3.22 (each m, 2H, NHCH$_2$ CH$_2$NH), 4.33–4.38 (t, 2H, CH$_2$—N), 6.85 (t, 1H, NHBoc), 7.48 and 8.18 (d, 1H, pyrrole), 8.36 (t, 1H, NHCO).

Step B: N,N'-Bis-[5-(2-amino-ethylcarbamoyl)-1-(3-methyl-butyl)-1H-pyrrol-3-yl]-terephthalamide 274

To stirred solution of compound 275 (70 mg, 0.15 mmol) in methanol (20 ml) was added 10% Pd/C (Degussa type, Aldrich) (0.1 g). the flask was evacuated and then flushed 3 times with hydrogen and finally filled with hydrogen at 25–30 psi. The resultant suspention was stirred vigorously at 23° C. for 45 min. The suspended material was filtered, the filtrate was evaporated to dryness. The resulted aminopyrrole was dissolved in 3 ml of dry DMF was added to phthalic acid dipentafluorophenyl ester (25 mg, 0.07 mmol), The reaction mixture was stirred for 15 hours at 55° C., DMF was evaporated. The Boc-protected derivative 276 was dissolved in methanol (3 ml) and 3 ml of 4N HCl in dioxane was added. In 30 min the solvent was evaporated and the solid was purified by HPLC as described in example 1, step D. Yield 40% of compound 274. ES MS: 607.78 (M+H$^+$).

Example 139

N,N'-Bis-[5-(2-guanidino-ethylcarbamoyl)-1-(3-methyl-butyl)-1H-pyrrol-3-yl]-terephthalamide 277

A solution of compound 274 (30 mg, 0.05 mmol) and pyrazole-1-carboxamidine hydrochloride (0.1 mmol, 9 mg) in 5 ml of DMF were kept at ambient temperature overnight, evaporated. The residue was purified by HPLC as as described in example 1, step D. Yield 68% of N,N'-Bis-[5-(2-guanidino-ethylcarbamoyl)-1-(3-methyl-butyl)-1H-pyrrol-3-yl]-terephthalamide 277. ES MS: 691.81 (M+H$^+$).

Formulation Examples

The following are representative pharmaceutical formulations containing a compound of Formula (I).

Example 1

Tablet Formulation

The following ingredients are mixed intimately and pressed into single scored tablets.

| Quantity per Ingredient | tablet, mg |
| --- | --- |
| compound of this invention | 400 |
| cornstarch | 50 |
| croscarmellose sodium | 25 |
| lactose | 120 |
| magnesium stearate | 5 |

Example 2

Capsule Formulation

The following ingredients are mixed intimately and loaded into a hard-shell gelatin capsule.

| Quantity per | Ingredient capsule, mg |
| --- | --- |
| compound of this invention | 200 |
| lactose, spray-dried | 148 |
| magnesium stearate | 2 |

Example 3

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 ml |
| colorings | 0.5 mg |
| distilled water | q.s. to 100 ml |

Example 4

Injectable Formulation

The following ingredients are mixed to form an injectable formulation.

| Ingredient | Amount |
|---|---|
| compound of this invention | 0.2 mg–20 mg |
| sodium acetate buffer solution, 0.4 M | 2.0 ml |
| HCl (1 N) or NaOH (1 N) | q.s. to suitable pH |
| water (distilled, sterile) | q.s. to 20 ml |

Example 5

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| | |
|---|---|
| compound of the invention | 500 mg |
| Witepsol ® H-15 | balance |

Biological Examples

Example 1

Minimum Inhibitory Concentration (MIC) Assays:

The assays described below were used to measure the minimum inhibitory concentration (MIC) of a compound necessary to completely inhibit visible growth of the organism tested. These assays are adapted from NCCLS protocols M7-A4 and M27-A (NCCLS vol 17:9 and vol 17:2) as modified by Sandven, S. *Clin. Micro.* (1999) 37:12, p.3856–3859. MIC values for *Aspergillus fumigatus* were determined using NCCLS protocol M38-P.

Inoculum preparation incubation and reading results

All compounds were dissolved in 100% DMSO to a stock concentration of 10 mM and use fresh or stored at −80° C. Stock compounds were kept frozen until needed and used freshly with no more then one freeze-thaw cycle. When used for test purposes, compounds were diluted in the appropriate media depending on the organism being tested.

For yeast and aspergillus species, seven 1:2 serial dilutions of compound in appropriate media buffered with MOPS at pH 7.0 were prepared such that the final starting test compound concentrations were 50.0 uM for yeast and 50 uM aspergillus species. For bacteria, dilutions were made in growth media used for the particular bacteria being tested.

Yeast

Five well-separated colonies from a 24 hr Sabouraud Dextrose plate incubated at 35C were picked and resuspended into 5.0 ml of normal saline. The $O.D._{530}$ was read and the culture was adjusted to 0.5 McFarland units with normal saline. A 1:2000 dilution was made with RPMI 1640 media buffered with MOPS at pH 7.0 and 100 µL of this inoculum preparation was added to an equal volume of test compound-containing media. 25 µL of the redox indicator Alamar Blue (Biosource International) was added to each well and the plates were incubated for 48 h at 35 C. Wells having yeast growth changed color from blue to pink. Accordingly, the MIC was calculated based on the well with the lowest concentration which did not change color from blue to pink, e.g., growth was inhibited.

Bacteria

Inoculums are made in the same manner as yeast except all dilutions are made in normal saline, with a final dilution of 1:200 and an inoculum of 10 µL. Solid and liquid media, as well as plate incubation times for the various organisms tested, are listed in Table 1 below.

TABLE 1

| Organism | Liquid media | Solid media (agar) | 96 well plate incubation time | Definition |
|---|---|---|---|---|
| VRE-UCD3 | BHI | BHIA | No vancomycin-16 h 25 µg/mL Vancomycin-24 h | BHI-Brain Heart Infusion |
| VRE-CSUC4 | BHI | BHIA | No vancomycin-16 h 25 µg/mL Vancomycin-24 h | BHI-Brain Heart Infusion |
| VRE-UL17 | BHI | BHIA | No vancomycin-16 h 25 µg/mL Vancomycin-24 h | BHI-Brain Heart Infusion |
| VRE-BM4147 | BHI | BHIA | No vancomycin-16 h 25 µg/mL Vancomycin-24 h | BHI-Brain Heart Infusion |
| *Moraxella catarrhalis* | BHI | BHIA | 16 h | BHI-Brain Heart Infusion |
| *Bacillus cereus* | CAMHB | BHIA | 16 h | BHI-Brain Heart Infusion |
| *Pseudomonas aeruginosa* | CAMHB | BHIA | 16 h | BHI-Brain Heart Infusion |
| *Staphylococcus aureus* | CAMHB | BHIA | 16 h | CAMHB-Cation adjusted Muller Hinton broth |
| *Haemophilus influenzae* | HTM | Chocolate Agar | 24 h | Chocolate Agar-Nutrient agar + 5% heat lysed Sheep blood |
| *Streptococcus pneumoniae* | CAMHB + 5% LHB | MHA + 5% SB | 24 h | LHB-Lysed Horse Blood |
| *Candida albicans* | RPMI | SABDEX | 48 h | SABDEX-Sabouraud Dextrose Agar |

Filamentous fungi

Inoculums are made by incubating *Aspergillus fumigatus* for 7 days at 35 C on potato dextrose agar slants. Slants are then covered with 1.0 ml of 0.85% saline, one drop of Tween 20 is added and colonies are teased with a sterile transfer loop to create a suspension which is allowed to sit for 5 min so heavier particles can drop out. The upper suspension is separated and adjusted to an optical density of 0.09 to 0.11. The resulting suspension is diluted 1:50 which yields 2× the final inoculum needed. Micro dilution trays are prepared as with yeast and incubated for 48 h at 35 C. For our purposes the MIC is defined as the lowest compound concentration at which no visible growth is observed after 48 h.

Compounds of this invention were tested in assays described above and were found to be active. Examples of compounds that exhibited antibacterial activity (MIC<45.5 μM) are shown in FIG. 5. Examples of compounds that exhibited antifungal activity (MIC<45.5 μM) are shown in FIG. 6.

Topoisomerase Inhibition Assays

*Candida albicans* topoisomerases I and II (cTop1 and cTop2) were isolated according to Fostel et al. (1992) and Shen et al. (1992). Human topoisomerases I and II (hTop1 and hTop2) were purchased from Topogen (Columbus, Ohio).

Inhibition of topoisomerase I

Effects of GL compounds on DNA relaxation by topoisomerase I were studied using gel electrophoresis. Negatively supercoiled plasmid DNA (pARG, 8 kb) was used as the substrate. The reaction for *C. albicans* topoisomerase I was performed in 25 mM TrisHCl, pH 7.5, 50 mM NaCl, 2.5 mM MgCl2, 0.5 mM EDTA and 50 ug/m-L BSA at 35° C. The reaction was stopped at any given time by adding SDS to a final concentration of 0.5%. Subsequently, proteinase K was added to 250 ug/mL and the mixture was incubated at 60° C. for 30 min. The reaction mixture was further extracted with phenol followed by pbenol:isoamyl alcohol::chloroform (25:1:24). Samples were loaded on 0.8% agarose gel and subject to electrophoresis using 1×TBE. Different DNA intercalators were used for better gel resolution. Ethidium bromide was sometimes added to both the gel and the running buffer to 0.25 ug/mL. In other cases, chloroquine was added to 0.25 ug/mL to separate the DNA topoisomers.

Inhibition of topoisomerase II

Effects of GL compounds on topoisomerase II were investigated by monitoring decatenation reactions using entangled kinetoplast DNA (Topogen). The decatenation reaction was performed in 10 mM TrisHCl, pH 7.5, 50 mM NaCl, 50 mM KCl, 5 mM MgCl$_2$, 0.1 mM EDTA and 0.5 mM ATP. The reaction was stopped at any given time by adding SDS to a final concentration of 1%. Subsequently, proteinase K was added to 250 ug/mL and the mixture was incubated at 60° C. for 30 min. The reaction mixture was further extracted with phenol followed by phenol:isoamyl alcohol:chloroform (25:1:24). Samples were loaded on 0.8% agarose gel and subject to electrophoresis using 1×TBE. Ethidium bromide was added to both the gel and the running buffer to 0.25 ug/mL.

DNA Binding Properties of Compounds of this Invention

Fluorescence Studies

When compounds prefer to bind to the minor groove of dsDNA, they induce DNA duplex formation. Hybridization of complementary fluorescently labeled strands brings the two labels, fluorescein and dabcyl, in close proximity, thus quenching the fluorescence of fluorescein. Therefore, this hybridization stabilization assay ("HSA") can be used to measure ligand binding to double-stranded DNA.

The DNA binding properties of several compounds of this invention were investigated by fluorescence spectroscopy. The 11-bp oligo CGA$_8$G ("FQ11") having fluorescein at the 5' end on one strand and dabcyl at the 3' end on the complementary strand was used as the AT-rich ligand binding target. At room temperature, FQ11 remains largely single-stranded in the HEN buffer (10 mM HEPES, pH 7.2, 0.1 mM EDTA and 10 mM NaCl).

Fluorescence was measured at the excitation wavelength of 485 nm and the emission wavelength of 530 nm using a 96-well plate fluoreader (PE CytoFluork Series 4000). The FQ11 concentration was kept at 5 nM (for duplex concentration) for the binding experiments and varying concentrations of ligands were added. All experiments were performed in duplicate in the HEN buffer at room temperature unless otherwise stated. Standard deviations were calculated based on the duplicate experiments. The fluorescence signal was normalized against the fluorescence in the absence of compounds. Decreasing fluorescence signals with increasing ligand concentrations indicated binding of the ligand to dsDNA. Through this least-square fitting procedure, apparent dissociation constants ($K_{d,app}$) for each compound tested were calculated. The studies demonstrated that compounds of this invention bind to DNA very tightly, with apparent $K_{d,app}$ values below 100 nM for most compounds tested.

Circular Dichroism Studies

Because of the electronic interactions between ligand and DNA, ligand binding can often induce circular dichroism ("CD") signals that are absent when DNA or ligand is alone in solution. DNA binding of compounds of this invention were determined using CD spectroscopy.

All solution conditions were the same as described above. PolydA-polydT was used at 50 μM. CD signal was monitored using a JASCO J-600 CD polarimeter at room temperature. The results showed binding properties that indicated a 2:1 complex. The dramatic CD change in the DNA absorbing region (260–300 nm) upon binding of these compounds demonstrated that compounds of this invention induced DNA conformational changes.

DNA Thermal Melting Studies

Interactions between DNA and compounds of this invention were investigated using thermal melting techniques monitored at UV wavelength 260 nm. All investigated compounds showed a stabilization effect on DNA duplex formation.

During melting experiments, 3 uM GCGA3T3CGC (A3T3) oligo duplex was mixed with 6 uM of compound in HEN buffer in a total volume of 200 uL. The UV absorbance was monitored at 260 nm with a Beckman UV spectrophotometer with temperature control. The melting temperature (Tm) where half of the duplex dissociates was determined at relative absorbance of 0.5. The free A3T3 has a Tm of approximately 42° C. With the presence of ligands, the Tm increases. The results indicated compounds of this invention tend to stabilize duplex DNA by binding to the minor groove. Increases in Tm have also been observed for duplex oligo CGATTATTAAGC in the presence of the compound.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the fall scope of equivalents to which such claims are entitled.

All patents, patent applications and publications cited in this application are hereby incorporated by reference in their entirety for all purposes to the same extent as if each individual patent, patent application or publication were so individually denoted.

What is claimed:

1. A compound of Formula (I):

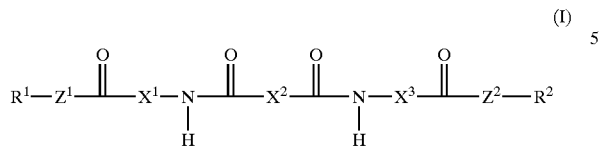

wherein;

Z$^1$ and Z$^2$ are independently —NR$^3$— or —O—;

R$^1$ and R$^2$ are independently substituted alkyl, substituted aryl, heteroaryl, or substituted heteroaryl provided that at least one of R$^1$ and R$^2$ is a group that can form a pharmaceutically acceptable acid addition salt;

R$^3$ is hydrogen, alkyl or R$^3$ and R$^1$ or R$^2$ together with the atoms to which they are attached form a heterocyclic ring;

X$^2$ is a fused bicyclic or tricyclic heteroaryl group:

X$^2$ and X$^3$ are independently aryl, substituted aryl, heteroaryl, substituted heteroaryl, or —CHR$^4$, wherein R$^4$ is natural or unnatural amino acid side chain;

or a pharmaceutically acceptable acid addition salt thereof.

2. The compound of claim 1, wherein Z$^1$ and Z$^2$ are —NH—.

3. The compound of claim 2, wherein R$^1$ and R$^2$ are independently substituted alkyl groups.

4. The compound of claim 2, wherein X$^2$ is selected from a group consisting of the following moieties:

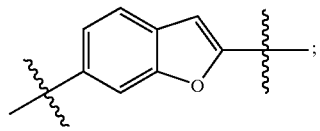

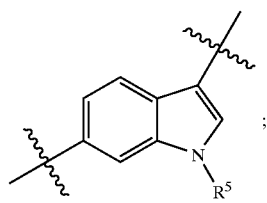

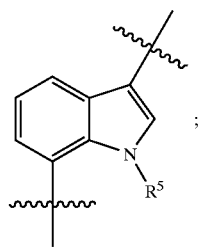

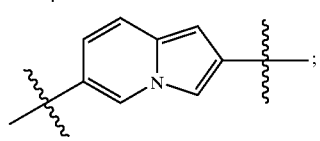

-continued

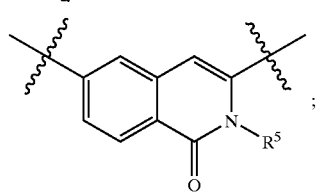

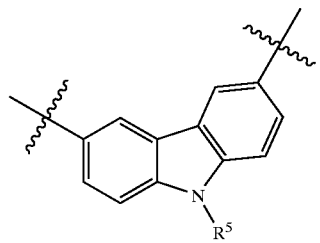

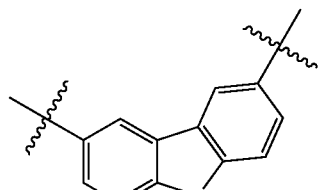

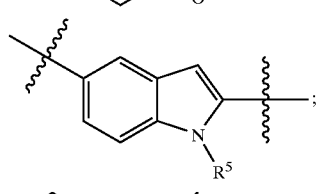

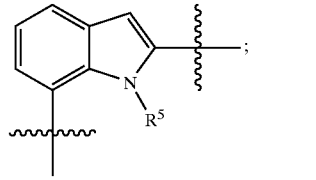

-continued

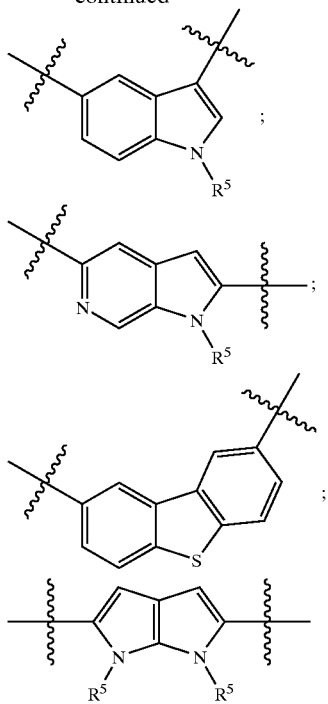

wherein,
R[5] is hydrogen, alkyl or substituted alkyl;
R[6] is hydrogen, alkyl, halo or alkoxy; and
R[7] is hydrogen, alkyl or halo.

5. The compound of claim 2, wherein $X^1$ and $X^3$ are heteroaryl or substituted heteroaryl moieties independently selected from a group consisting of the following moieties:

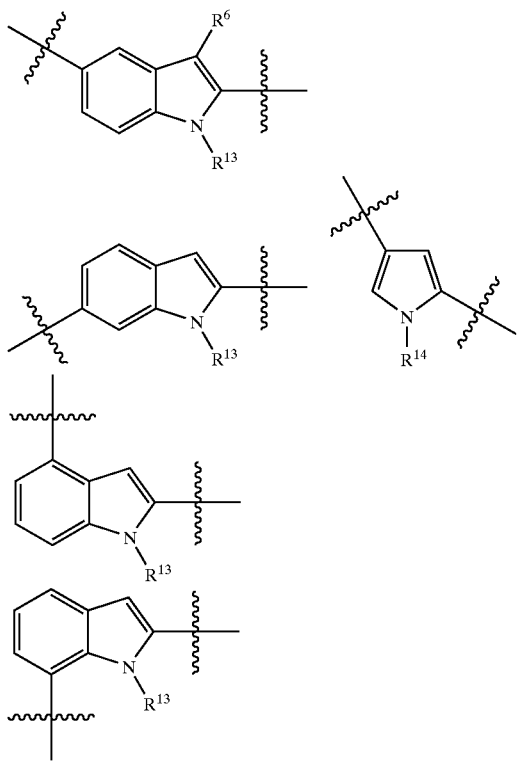

-continued

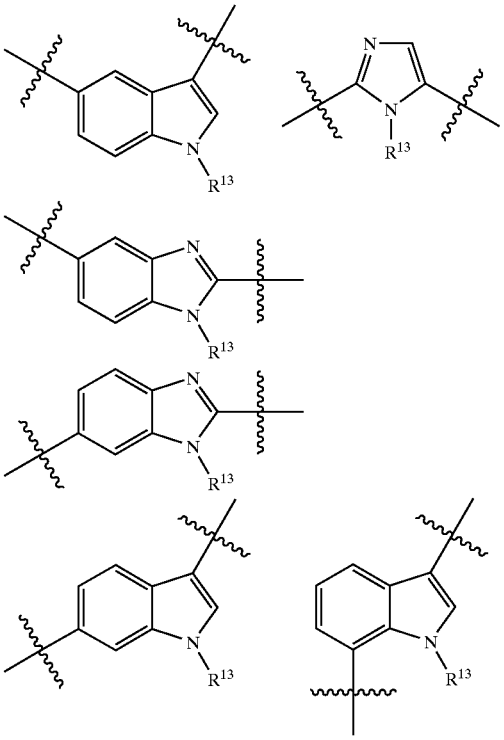

wherein
R[13] is hydrogen or alkyl; and,
R[14] is hydrogen, alkyl or substituted alkyl.

6. The compound of claim 3, wherein $R^1$ and $R^2$ are substituted alkyl moieties independently selected from a group consisting of the following moieties:

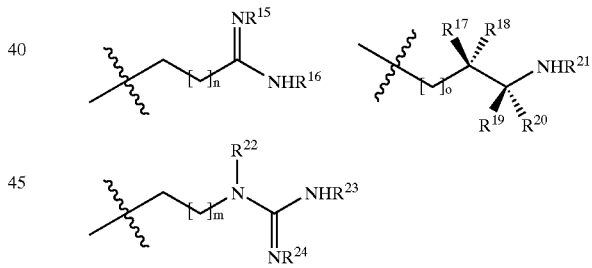

wherein
R[15] is hydrogen, hydroxyl, alkoxyl, alkyl, cycloalkyl or R[15] and R[16] together with the atoms to which they are attached form a heterocyclic ring;
R[16] is hydrogen, hydroxyl, alkyl or cycloalkyl;
R[17], R[18], R[19] and R[20] are independently hydrogen or alkyl;
R[21] is hydrogen alkyl, substituted alkyl, cycloalkyl or acyl;
R[22] is hydrogen or alkyl, or R[22] and R[23] together with the atoms to which they are attached form a heterocyclic ring, or R[22] and R[24] together with the atoms to which they are attached form a heterocyclic ring.
R[23] is hydrogen, hydroxyl, alkyl, cycloalkyl or R[23] and R[24] together with the atoms to which they are attached form a heterocyclic ring;

$R^{24}$ is hydrogen, hydroxyl or alkyl;

m is 1, 2 or 3;

n is 1, 2 or 3; and, o is 0, 1, 2 or 3.

7. The compound of claim 5, wherein $R^{14}$ is an alkyl or substituted alkyl moiety, and wherein the moiety is selected from a group consisting of the following moieties:

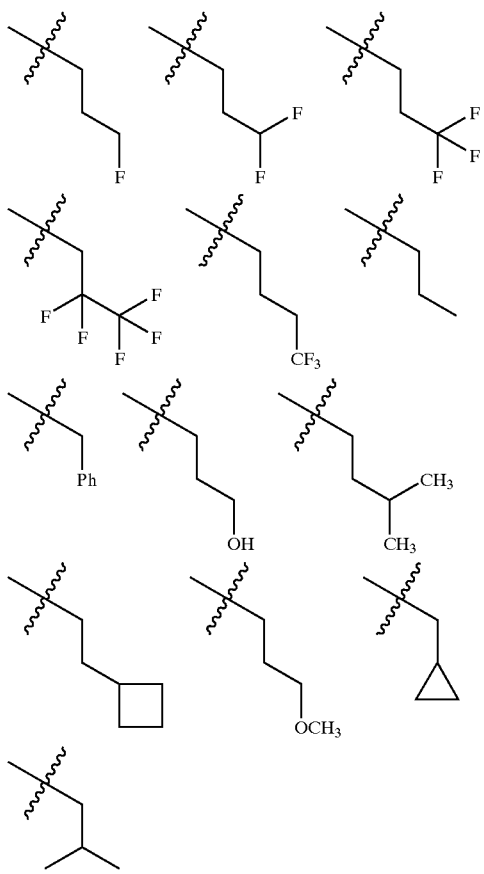

8. The compound of claim 4, wherein $X^1$ and $X^3$ are heteroaryl or substituted heteroaryl moieties independently selected from a group consisting of the following moieties:

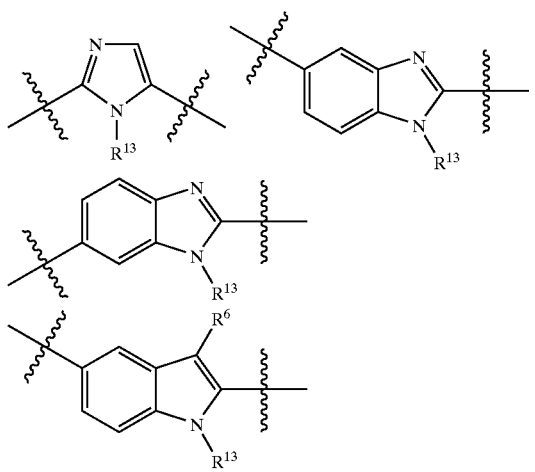

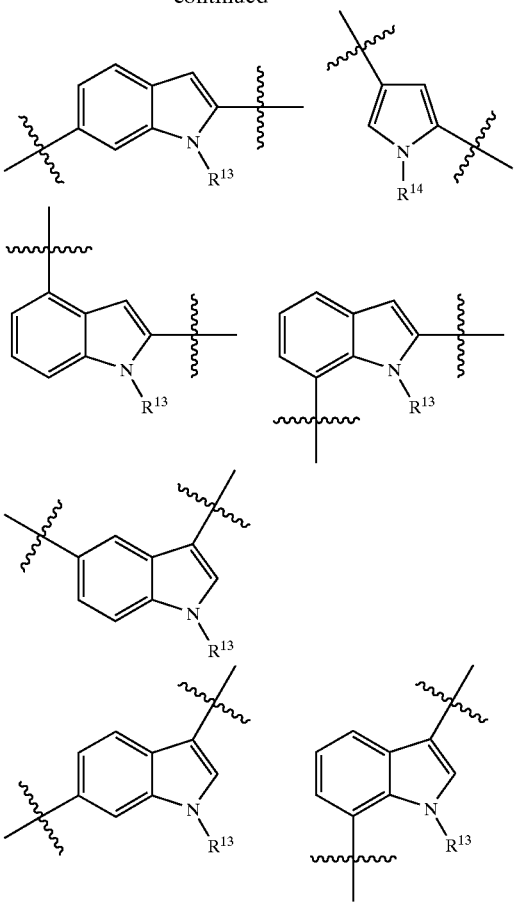

wherein
$R^{13}$ is hydrogen or alkyl;
$R^{14}$ is hydrogen, alkyl or substituted alkyl;
and wherein $R^1$ and $R^2$ are substituted alkyl moieties independently selected from a group consisting of the following moieties:

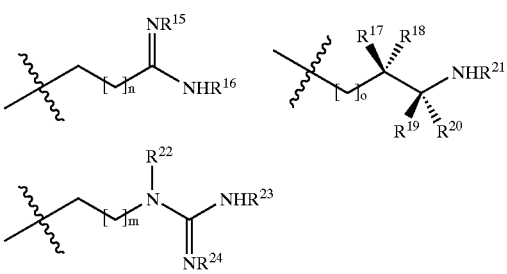

wherein
$R^{15}$ is hydrogen, hydroxyl, alkoxyl, alkyl, cycloalkyl or $R^{15}$ and $R^{16}$ together with the atoms to which they are attached form a heterocyclic ring;
$R^{16}$ is hydrogen, hydroxyl, alkyl or cycloalkyl;
$R^{17}$, $R^{18}$, $R^{19}$ and $R^{20}$ are independently hydrogen or alkyl;
$R^{21}$ is hydrogen alkyl, substituted alkyl, cycloalkyl or acyl;
$R^{22}$ is hydrogen or alkyl, or $R^{22}$ and $R^{23}$ together with the atoms to which they are attached form a heterocyclic ring, or $R^{22}$ and $R^{24}$ together with the atoms to which they are attached form a heterocyclic ring;

$R^{23}$ is hydrogen, hydroxyl, alkyl, cycloalkyl or $R^{23}$ and $R^{24}$ together with the atoms to which they are attached form a heterocyclic ring;

$R^{24}$ is hydrogen, hydroxyl or alkyl;

m is 1, 2 or 3;

n is 1, 2 or 3; and, o is 0, 1, 2 or 3.

9. The compound of claim 8, wherein $X^2$ is

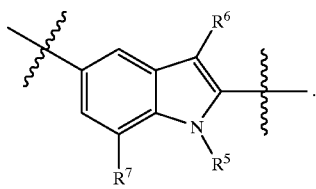

10. The compound of claim 8, wherein $X^1$ and $X^3$ are both

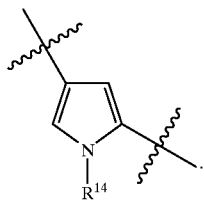

11. The compound of claim 9, wherein $R^1$ and $R^2$ are of the following structure:

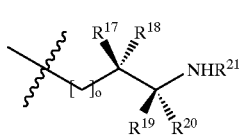

wherein o is 0;

$R^{17}$ and $R^{18}$ are hydrogen; and, $R^{21}$ is hydrogen, alkyl or acyl.

12. The compound of claim 10, wherein $R^1$ and $R^2$ are of the following structure:

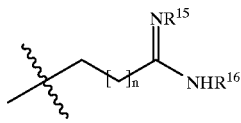

wherein $R^{15}$ and $R^{16}$ are hydrogen; and, n is 1 or 2.

13. The compound of claim 11, wherein $R^{19}$ and $R^{20}$ are hydrogen, and wherein $R^{21}$ is an alkyl group selected from a group consisting of methyl, ethyl and propyl, or an acyl moiety of the structure —C(O)C($R^{25}$)$R^{26}$)H, wherein $R^{25}$ is a substituent selected from a group consisting of the following substituents:

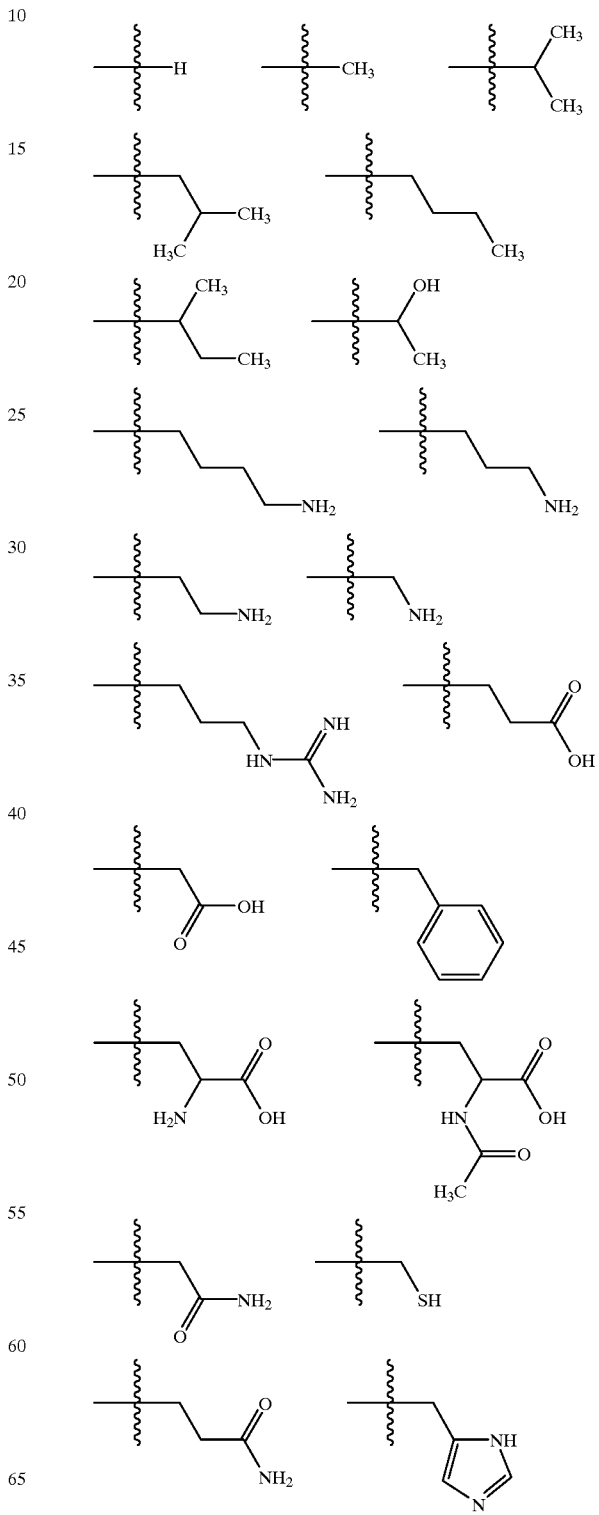

-continued

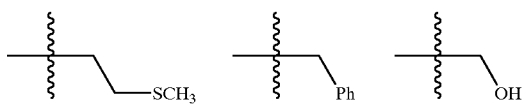

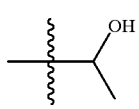

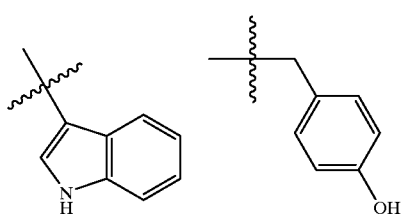

or R$^{25}$ and R$^{26}$ together with the atom to which they are attached form a heterocyclic ring of the following structure:

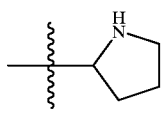

and wherein R$^{26}$ is a substituent selected from a group consisting of the following substituents: —H, —NH$_2$ and —NHCH$_3$.

14. The compound of claim 11, wherein R$^1$ and R$^2$ are independently of one of the following structures:

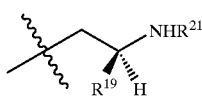 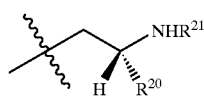

wherein

R$^{19}$ and R$^{20}$ are independently hydrogen or alkyl; and,

R$^{21}$ is hydrogen, alkyl or acyl.

15. The compound of claim 12, wherein R$^{14}$ is an alkyl or substituted alkyl moiety, and wherein the moiety is selected from a group consisting of the following moieties:

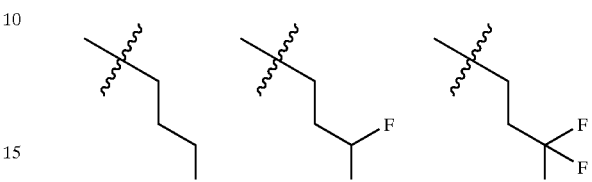

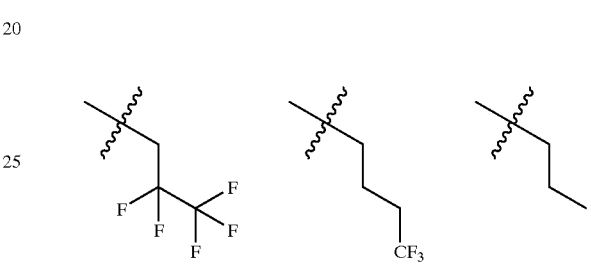

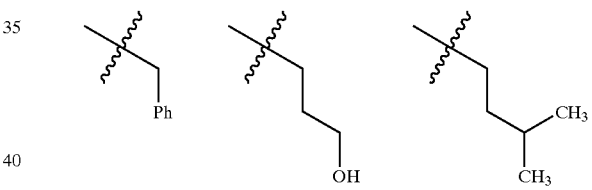

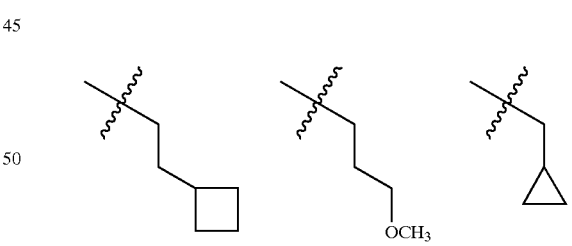

16. The compound according to claim 13, wherein the compound is of the following structure:

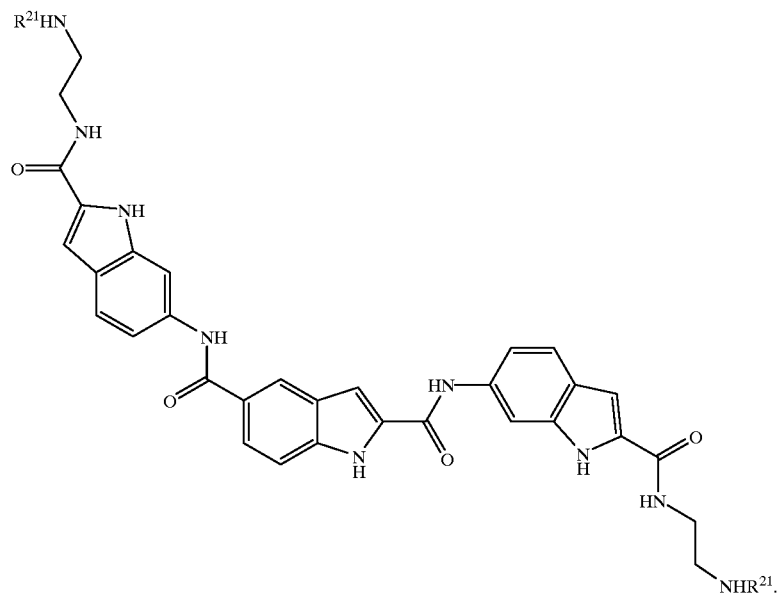
17. A pharmaceutical formulation comprising a pharmaceutically acceptable excipient and a anti-bacterially or anti-fungally effective amount of a compound of any one of claims 1, 2, or 3–16.
* * * * *